United States Patent
Borras et al.

(10) Patent No.: US 12,344,663 B2
(45) Date of Patent: Jul. 1, 2025

(54) ANTI-C3 ANTIBODIES AND ANTIGEN-BINDING FRAGMENTS THEREOF AND THEIR USES FOR TREATING EYE OR OCULAR DISEASES

(71) Applicants: CDR-Life AG, Schlieren (CH); Boehringer Ingelheim International GmbH, Ingelheim am Rhein (DE)

(72) Inventors: Leonardo Borras, Birmensdorf (CH); Pankaj Gupta, Scarsdale, NY (US); Stephanie Jungmichel, Oerlikon-Zuerich (CH); Christian Leisner, Thalwil (CH); Philipp Robert Richle, Zurich (CH); Fabian Scheifele, Maegenwil-Aargau (CH); Anna Sobieraj, Schlieren (CH)

(73) Assignees: CDR-Life AG, Schlieren (CH); Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 18/069,712

(22) Filed: Dec. 21, 2022

(65) Prior Publication Data

US 2023/0257455 A1 Aug. 17, 2023

Related U.S. Application Data

(60) Provisional application No. 63/292,513, filed on Dec. 22, 2021.

(51) Int. Cl.
| | | |
|---|---|---|
| *C07K 16/18* | (2006.01) | |
| *G01N 33/68* | (2006.01) | |
| *A61K 39/00* | (2006.01) | |

(52) U.S. Cl.
CPC ......... *C07K 16/18* (2013.01); *G01N 33/6893* (2013.01); *A61K 2039/505* (2013.01); *A61K 2039/54* (2013.01); *C07K 2317/24* (2013.01); *C07K 2317/622* (2013.01); *C07K 2317/92* (2013.01); *C07K 2317/94* (2013.01); *G01N 2333/4716* (2013.01)

(58) Field of Classification Search
CPC ............................ C07K 16/18; G01N 33/6893
USPC ..................................................... 424/135.1
See application file for complete search history.

(56) References Cited

U.S. PATENT DOCUMENTS

| | | | |
|---|---|---|---|
| 4,179,337 A | 12/1979 | Davis et al. | |
| 4,301,144 A | 11/1981 | Iwashita et al. | |
| 4,419,446 A | 12/1983 | Howley et al. | |
| 4,496,689 A | 1/1985 | Mitra | |
| 4,560,655 A | 12/1985 | Baker | |
| 4,601,978 A | 7/1986 | Karin | |
| 4,640,835 A | 2/1987 | Shimizu et al. | |
| 4,657,866 A | 4/1987 | Kumar | |
| 4,670,417 A | 6/1987 | Iwasaki et al. | |
| 4,767,704 A | 8/1988 | Cleveland et al. | |
| 4,791,192 A | 12/1988 | Nakagawa et al. | |
| 4,816,567 A | 3/1989 | Cabilly et al. | |
| 4,927,762 A | 5/1990 | Darfler | |
| 4,965,199 A | 10/1990 | Capon et al. | |
| 5,122,469 A | 6/1992 | Mather et al. | |
| 5,225,539 A | 7/1993 | Winter | |
| 5,631,144 A | 5/1997 | Lemoine et al. | |
| 5,888,809 A | 3/1999 | Allison | |
| 6,037,454 A | 3/2000 | Jardieu et al. | |
| 6,054,297 A | 4/2000 | Carter et al. | |
| 6,193,980 B1 | 2/2001 | Efstathiou et al. | |
| 2010/0291106 A1 | 11/2010 | Etemad-Gilbertson et al. | |
| 2019/0322730 A1* | 10/2019 | Duey ..................... | C07K 16/18 |
| 2020/0282012 A1 | 9/2020 | Francois | |
| 2022/0259296 A1 | 8/2022 | Borras et al. | |

FOREIGN PATENT DOCUMENTS

| | | |
|---|---|---|
| DE | 266710 A3 | 6/1983 |
| EP | 0183070 A2 | 6/1986 |
| EP | 0244234 A2 | 11/1987 |
| EP | 0402226 A1 | 12/1990 |
| WO | 8700195 A1 | 1/1987 |
| WO | 9003430 A1 | 4/1990 |
| WO | 90/07861 A1 | 7/1990 |
| WO | 9013646 A1 | 11/1990 |
| WO | 1994011026 A2 | 5/1994 |
| WO | 1996032478 A1 | 10/1996 |
| WO | 2004/031240 A1 | 4/2004 |
| WO | 2008/110348 A1 | 9/2008 |
| WO | 2009/000098 A2 | 12/2008 |
| WO | 2009/000099 A2 | 12/2008 |
| WO | 2008154251 A2 | 12/2008 |
| WO | 2009/056631 A2 | 5/2009 |
| WO | 2009/155725 A1 | 12/2009 |
| WO | 2009/155726 A2 | 12/2009 |
| WO | 2014/206561 A1 | 12/2014 |

(Continued)

OTHER PUBLICATIONS

Komenaka et Al., Clinics in Dermatology, 2004, vol. 22, p. 251-265 (Year: 2004).*
Evans et Al. (Q. J. Med 1999: 92: 299-307) (Year: 1999).*
Schiffman et Al., The New England Journal of Medicine, Vo. 353, No. 20, p. 2101-2104, 2005 (Year: 2005).*
Cuzick et Al. (The Lancet, vol. 361, p. 296-300, 2003) (Year: 2003).*
Hernandez-Ledesma (Peptides, vol. 30, p. 426-430, 2009) (Year: 2009).*

(Continued)

*Primary Examiner* — Yan Xiao
(74) *Attorney, Agent, or Firm* — Morgan, Lewis & Bockius LLP

(57) ABSTRACT

The present invention relates to antibodies and fragments thereof that target the complement C3. More specifically, anti-C3 antibodies and methods of use for the treatment of various diseases or disorders are disclosed.

94 Claims, 4 Drawing Sheets
Specification includes a Sequence Listing.

(56) References Cited

FOREIGN PATENT DOCUMENTS

| WO | 2016/040635 A1 | 3/2016 |
|---|---|---|
| WO | 2019/057787 A1 | 3/2019 |
| WO | 2019195136 A1 | 10/2019 |
| WO | 2019/238674 A1 | 12/2019 |
| WO | 2021159946 A1 | 8/2021 |
| WO | 2021226442 A2 | 11/2021 |
| WO | 2022/171771 A1 | 8/2022 |
| WO | 2023/118312 A1 | 6/2023 |

OTHER PUBLICATIONS

Paul, Fundamental Immunology, 3rd Edition, 1993, pp. 292-295 (Year: 1993).*
Bendig M. M. (Methods: A Companion to Methods in Enzymology, 1995; 8:83-93) (Year: 1995).*
Rudikoff et al. (Proc Natl Acad Sci USA 79: 1979-1983, 1982) (Year: 1982).*
Houdebine (Comparative Immunology, Microbiology, and Infectious Diseases, vol. 32, p. 107-121, 2009) (Year: 2009).*
Wall et Al., Theriogenology, vol. 45, p. 57-68, 1996 (Year: 1996).*
Houdebine et Al., Journal of Biotechnology, vol. 34, p. 269-287, 1994 (Year: 1994).*
Kappell et Al., Current Opinions in Biotechnology, vol. 3, p. 548-553, 1992 (Year: 1992).*
Pearson, W. et al., "Improved tools for biological sequence comparison." Proceedings of the National Academy of Sciences of the United States of America vol. 85,8 (1988): 2444-8.
Pedersen, H. et al., "A C3-specific nanobody that blocks all three activation pathways in the human and murine complement system." The Journal of biological chemistry vol. 295,26 (2020): 8746-8758.
Ricklin, D. et al., "Compstatin: a complement inhibitor on its way to clinical application." Advances in experimental medicine and biology vol. 632 (2008): 273-92.
Roovers, R. et al., "In vitro characterisation of a monovalent and bivalent form of a fully human anti Ep-CAM phage antibody." Cancer immunology, immunotherapy : CII vol. 50, 1 (2001): 51-9.
Stinchcomb, D. et al., "Isolation and characterisation of a yeast chromosomal replicator." Nature vol. 282,5734 (1979): 39-43.
Thotakura, N. et al., "Enzymatic deglycosylation of glycoproteins." Methods in enzymology vol. 138 (1987): 350-9.
Torelli, A. et al., "Advance and Adam: two algorithms for the analysis of global similarity between homologous informational sequences." Computer applications in the biosciences : CABIOS vol. 10,1 (1994): 3-5.
Extended European Search Report for European Patent Application No. 21216720.9 mailed Jun. 7, 2022, 30 pages.
Kabat, et al., "Sequences of Proteins of Immunological Interest." Public Health Service, National Institutes of Health, Bethesda, MD, 5th Ed., vol. 1 (Oct. 29, 1991).
Pluckthun, A. et al., "Antibodies from *Escherichia coli*." The Pharmacology of Monoclonal Antibodies (Springer-Verlag), vol. 113 (1994): 269-315.
Zapata, G. et al., "Engineering linear F(ab')2 fragments for efficient production in *Escherichia coli* and enhanced antiproliferative activity." Protein engineering vol. 8, 10 (1995): 1057-62.
Lefranc, M-P. et al., "The Immunoglobulin Facts Book." Academic Press (2001).
Myers, E. W. et al., "Approximate matching of regular expressions." Bulletin of mathematical biology vol. 51,1 (1989): 5-37.
Hakimuddin, T.S. et al., "A chemical method for the deglycosylation of proteins." Archives of Biochem. and Biophys., vol. 259 (Nov. 15, 1987): 52-57.
Hariprasad, S. "Suprachoroidal administration for retinal drug delivery: a promising targeted approach to treat posterior-segment ophthalmic disease." Retinal Physician. vol. 13 (Apr. 2016): 20-23.
Goldstein, D., "Achieving drug delivery via the suprachoroidal space." Retina Today 9(5) (2014): 82-87.

Van Den Berg, J.A. et al., "Kluyveromyces as a host for heterologous gene expression: expression and secretion of prochymosin." Bio-technology (Nature Publishing Company) vol. 8,2 (1990): 135-9.
Reyes, G. R. et al., "Expression of human beta-interferon cDNA under the control of a thymidine kinase promoter from herpes simplex virus." Nature vol. 297,5867 (1982): 598-601.
Yaniv, M., "Enhancing elements for activation of eukaryotic promoters." Nature vol. 297,5861 (1982): 17-8.
Urlaub, G. et al., "Isolation of Chinese hamster cell mutants deficient in dihydrofolate reductase activity." Proceedings of the National Academy of Sciences of the United States of America vol. 77,7 (1980): 4216-20.
Loktev, A. et al., "NGM621 is a potent inhibitory anti-complement C3 antibody in development for treatment of geographic atrophy." ARVO 2020 Meeting, Poster B0267.
Alfthan, K. et al., "Properties of a single-chain antibody containing different linker peptides." Protein engineering vol. 8,7 (1995): 725-31.
Almagro, J. et al., "Antibody modeling assessment." Proteins vol. 79,11 (2011): 3050-66.
Altschul, S. et al., "Basic local alignment search tool." Journal of molecular biology vol. 215,3 (1990): 403-10.
Altschul, S. et al., "Gapped BLAST and PSI-BLAST: a new generation of protein database search programs." Nucleic acids research vol. 25, 17 (1997): 3389-402.
Barnes, D. et al., "Methods for growth of cultured cells in serum-free medium." Analytical biochemistry vol. 102,2 (1980): 255-70.
Brennan, M. et al., "Preparation of bispecific antibodies by chemical recombination of monoclonal immunoglobulin G1 fragments." Science (New York, N.Y.) vol. 229,4708 (1985): 81-3.
Carter, P. et al., "High level *Escherichia coli* expression and production of a bivalent humanized antibody fragment." Bio/technology (Nature Publishing Company) vol. 10,2 (1992): 163-7.
Choi, I. et al., "Recombinant chimeric OKT3 scFv IgM antibodies mediate immune suppression while reducing T cell activation in vitro." European journal of immunology vol. 31,1 (2001): 94-106.
Chothia, C. et al., "Domain association in immunoglobulin molecules. The packing of variable domains." Journal of molecular biology vol. 186,3 (1985): 651-63.
Chothia, C. et al., "Canonical structures for the hypervariable regions of immunoglobulins." Journal of molecular biology vol. 196,4 (1987): 901-17.
Clackson, T. et al., "Making antibody fragments using phage display libraries." Nature vol. 352,6336 (1991): 624-8.
De Groot, A. et al., "Activation of natural regulatory T cells by IgG Fc-derived peptide "Tregitopes"." Blood vol. 112,8 (2008): 3303-11.
De Groot, A. et al., "Reducing risk, improving outcomes: bioengineering less immunogenic protein therapeutics." Clinical immunology (Orlando, Fla.) vol. 131,2 (2009): 189-201.
Dilillo, D. et al., "Selective and efficient inhibition of the alternative pathway of complement by a mAb that recognizes C3b/iC3b." Molecular immunology vol. 43,7 (2006): 1010-9.
Edge, A. et al., "Deglycosylation of glycoproteins by trifluoromethanesulfonic acid." Analytical biochemistry vol. 118,1 (1981): 131-7.
Fleer, R. et al., "Stable multicopy vectors for high-level secretion of recombinant human serum albumin by Kluyveromyces yeasts." Bio/technology (Nature Publishing Company) vol. 9,10 (1991): 968-75.
Gaudreault, J. et al., "Preclinical pharmacokinetics of Ranibizumab (rhuFabV2) after a single intravitreal administration." Investigative ophthalmology & visual science vol. 46,2 (2005): 726-33.
Graham, F. et al., "Characteristics of a human cell line transformed by DNA from human adenovirus type 5." The Journal of general virology vol. 36,1 (1977): 59-74.
Guss, B. et al., "Structure of the IgG-binding regions of streptococcal protein G." The EMBO journal vol. 5,7 (1986): 1567-75.
Sojar, H. et al., "A chemical method for the deglycosylation of proteins." Archives of biochemistry and biophysics vol. 259, 1 (1987): 52-7.

(56) References Cited

OTHER PUBLICATIONS

Ham, R. et al., "Media and growth requirements." Methods in enzymology vol. 58 (1979): 44-93. doi: 10.1016/s0076-6879(79)58126-9.
Heeley, R. et al., "Mutations flanking the polyglutamine repeat in the modulatory domain of rat glucocorticoid receptor lead to an increase in affinity for hormone." Endocrine research vol. 28,3 (2002): 217-29.
Higgins, D. et al., "Using Clustal for multiple sequence alignments." Methods in enzymology vol. 266 (1996): 383-402.
Holliger, P. et al., ""Diabodies": small bivalent and bispecific antibody fragments." Proceedings of the National Academy of Sciences of the United States of America vol. 90,14 (1993): 6444-8.
Honegger, A. et al., "Yet another numbering scheme for immunoglobulin variable domains: an automatic modeling and analysis tool." Journal of molecular biology vol. 309,3 (2001): 657-70.
Hu, S. et al., "Minibody: A novel engineered anti-carcinoembryonic antigen antibody fragment (single-chain Fv-CH3) which exhibits rapid, high-level targeting of xenografts." Cancer research vol. 56,13 (1996): 3055-61.
Jackson, T. et al., "Human retinal molecular weight exclusion limit and estimate of species variation." Investigative ophthalmology & visual science vol. 44,5 (2003): 2141-6.
Jensen, R. et al., "A potent complement factor C3-specific nanobody inhibiting multiple functions in the alternative pathway of human and murine complement." The Journal of biological chemistry vol. 293, 17 (2018): 6269-6281.
Jones, E W., "Proteinase mutants of *Saccharomyces* cerevisiae." Genetics vol. 85,1 (1977): 23-33.
Karlin, S. et al., "Methods for assessing the statistical significance of molecular sequence features by using general scoring schemes." Proceedings of the National Academy of Sciences of the United States of America vol. 87,6 (1990): 2264-8.
Karlin, S. et al., "Applications and statistics for multiple high-scoring segments in molecular sequences." Proceedings of the National Academy of Sciences of the United States of America vol. 90,12 (1993): 5873-7.
Katschke, K. et al., "Structural and functional analysis of a C3b-specific antibody that selectively inhibits the alternative pathway of complement." The Journal of biological chemistry vol. 284, 16 (2009): 10473-9.
Katschke, K. et al., "Classical and alternative complement activation on photoreceptor outer segments drives monocyte-dependent retinal atrophy." Scientific reports vol. 8,1 7348. May 9, 2018.
Kipriyanov, S. et al., "Bispecific tandem diabody for tumor therapy with improved antigen binding and pharmacokinetics." Journal of molecular biology vol. 293, 1 (1999): 41-56.
Köhler, G. et al., "Continuous cultures of fused cells secreting antibody of predefined specificity." Nature vol. 256,5517 (1975): 495-7.
Lefranc, M. et al., "IMGT unique numbering for immunoglobulin and T cell receptor variable domains and Ig superfamily V-like domains." Developmental and comparative immunology vol. 27,1 (2003): 55-77.
Liljeblad, M. et al., "Analysis of agalacto-IgG in rheumatoid arthritis using surface plasmon resonance." Glycoconjugate journal vol. 17,5 (2000): 323-9.
Lindmark, R. et al., "Binding of immunoglobulins to protein A and immunoglobulin levels in mammalian sera." Journal of immunological methods vol. 62, 1 (1983): 1-13.
Maier, J. et al., "Assessment of fully automated antibody homology modeling protocols in molecular operating environment." Proteins vol. 82,8 (2014): 1599-610.
Marks, J. et al., "By-passing immunization. Human antibodies from V-gene libraries displayed on phage." Journal of molecular biology vol. 222,3 (1991): 581-97.
Mastellos, Dimitrios C et al. "Compstatin: a C3-targeted complement inhibitor reaching its prime for bedside intervention." European journal of clinical investigation vol. 45,4 (2015): 423-40.
Mastellos, D. et al., "Clinical promise of next-generation complement therapeutics." Nature reviews. Drug discovery vol. 18,9 (2019): 707-729.
Mather, J., "Establishment and characterization of two distinct mouse testicular epithelial cell lines." Biology of reproduction vol. 23, 1 (1980): 243-52.
Mather, J. et al., "Culture of testicular cells in hormone-supplemented serum-free medium." Annals of the New York Academy of Sciences vol. 383 (1982): 44-68.
Morimoto, K. et al., "Single-step purification of F(ab')2 fragments of mouse monoclonal antibodies (immunoglobulins G1) by hydrophobic interaction high performance liquid chromatography using TSKgel Phenyl-5PW." Journal of biochemical and biophysical methods vol. 24, 1-2 (1992): 107-17.
Morrison, S. et al., "Chimeric human antibody molecules: mouse antigen-binding domains with human constant region domains." Proceedings of the National Academy of Sciences of the United States of America vol. 81,21 (1984): 6851-5.
Morrison, P. et al., "Advances in ophthalmic drug delivery." Therapeutic delivery vol. 5,12 (2014): 1297-315.
Noris, M. et al., "Overview of complement activation and regulation." Seminars in nephrology vol. 33,6 (2013): 479-92.
Paixão-Cavalcante, D. et al., "A humanized antibody that regulates the alternative pathway convertase: potential for therapy of renal disease associated with nephritic factors." Journal of immunology (Baltimore, Md. : 1950) vol. 192,10 (2014): 4844-51.
Patel, A et al., "Ocular drug delivery systems: An overview." World journal of pharmacology vol. 2,2 (2013): 47-64.
Al-Lazikani et al., "Standard Conformations for the Canonical Structures of Immunoglobulins," J. Mol. Biol., 273 (4), pp. 927-948 (Nov. 7, 1997).
Bendig, "Humanization of Rodent Monoclonal Antibodies by CDR Grafting," Methods: A Companion to Methods in Enzymology, 8 (2), pp. 83-93 (1995).
Clark et al., "Type 1 Diabetes: A Chronic Anti-Self-Inflammatory Response," Frontiers in Immunology, 8 (1898), pp. 1-10 (Dec. 22, 2017).
Cuzick et al., "Overview of the main outcomes in breast-cancer prevention trials," The Lancet, 361, pp. 296-300 (Jan. 25, 2003).
Evans et al., "Vaccine therapy for cancer—fact or fiction?" Q J Med, 92, pp. 299-307 (1999).
Fennell et al., "CDR-restricted engineering of native human scFvs creates highly stable and soluble bifunctional antibodies for subcutaneous delivery," mAbs, 5 (6), pp. 882-895 (Nov./Dec. 2013).
Hariprasad, "Suprachoroidal Administration for Retinal Drug Delivery," Retinal Physician, 13, pp. 20-23 (Apr. 2016).
Hernandez-Ledesma et al., "Lunasin, a novel seed peptide for cancer prevention," Peptides, 30 (2), pp. 426-430 (Feb. 2009).
Hirvonen et al., "Hydrodynamic Radii of Ranibizumab, Aflibercept and Bevacizumab Measured by Time-Resolved Phosphorescence Anisotropy," Pharm Res, 33, pp. 2025-2032 (May 25, 2016).
Houdebine, "Production of pharmaceutical proteins by transgenic animals," Comparative Immunology, Microbiology and Infectious Diseases, 32 (2), pp. 107-121 (Mar. 2009).
Houdebine, "Production of pharmaceutical proteins from transgenic animals," Journal of Biotechnology, 34 (3), pp. 269-287 (May 31, 1994).
Jaskowski et al., "Comparison of Three Different Methods for Measuring Classical Pathway Complement Activity," Clinical and Diagnostic Laboratory Immunology, 6 (1), pp. 137-139 (Jan. 1999).
Jiang et al., "Nanotechnology in retinal drug delivery," Int J Opthalmol, 11 (6), pp. 1038-1044 (Jun. 18, 2018).
Kappel et al., "Regulating gene expression in transgenic animals," Current Opinion in Biotechnology, 3 (5), pp. 548-553 (Oct. 1992).
Kingsman et al., "Replication in Saccharomyces cerevisiae of plasmid pBR313 carrying DNA from the yeast trpl region," Gene, 7 (2), pp. 141-152 (Oct. 1979).
Komenaka et al., "Immunotherapy for Melanoma," Clinics in Dermatology, 22 (3), pp. 251-265 (May-Jun. 2004).
Kulmanov et al., "DeepGO: predicting protein functions from sequence and interactions using a deep ontology-aware classifier," Bioinformatics, 34 (4), pp. 660-668 (Feb. 2018).

(56) References Cited

OTHER PUBLICATIONS

Liao et al., "Complement C3 Inhibitor Pegcetacoplan for Geographic Atrophy Secondary to Age-Related Macular Degeneration," Opthalmology, 127 (2), pp. 186-195 (Feb. 2020).
Mufarrege et al., "De-immunized and Functional Therapeutic (DeFT) versions of a long lasting recombinant alpha interferon for antiviral therapy," Clinical Immunology, 176, pp. 31-41 (Mar. 2017).
Okroj et al., "Functional Analyses of Complement Convertases Using C3 and C5-Depleted Sera," PLoS One, 7 (10), e47245, 14 pp. (Oct. 2012).
Paul, "Structure and Function of Immunoglobulins," Fundamental Immunology, Third Edition, Chapter 9, pp. 292-295 (1993).
Pitkanen et al., "Permeability of Retinal Pigment Epithelium: Effects of Permeant Molecular Weight and Lipophilicity," IOVS, 46 (2), pp. 641-646 (Feb. 2005).
Ridgway, "Mammalian Expression Vectors," Biotechnology, pp. 467-492 (1987).
Rudikoff et al., "Single amino acid substitution altering antigen-binding specificity," Proc Natl Acad Sci USA, 79, pp. 1979-1983 (Mar. 1982).
Schiffman et al., "The Promise of Global Cervical-Cancer Prevention," N Engl J Med, 353 (20), pp. 2101-2104 (Nov. 17, 2005).
Tomar et al., "Molecular basis of high viscosity in concentrated antibody solutions: Strategies for high concentration drug product development," mAbs, 8 (2), pp. 216-228 (Feb. 8, 2016).
Tomlinson et al., "Human alternative complement pathway-mediated lysis of rabbit erythrocytes is enhanced by natural anti-Galalpha1-3Gal antibodies," J Immunol, 159 (11), pp. 5605-5609 (Dec. 1, 1997).
Tschumper et al., "Sequence of a yeast DNA fragment containing a chromosomal replicator and the TRP1 gene," Gene, 10 (2), pp. 157-166 (Jul. 1980).
UniProtKB P01024, 28 pp. (Jul. 24, 2024).
Wall, "Transgenic Livestock: Progress and Prospects for the Future," Theriogenology, 45 (1), pp. 57-68 (Jan. 1996).
Bork, "Powers and Pitfalls in Sequence Analysis: The 70% Hurdle," Genome Research, 10 (4), pp. 398-400 (Apr. 1, 2000).
Bowie et al., "Deciphering the Message in Protein Sequences: Tolerance to Amino Acid Substitutions," Science, 247 (4948), pp. 1306-1310 (Mar. 16, 1990).
Burgess et al., "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue," The Journal of Cell Biology, 111 (5), pp. 2129-2138 (Nov. 1990).
Casset et al., "A peptide mimetic of an anti-CD4 monoclonal antibody by rational design," Biochemical and Biophysical Research Communications, 307 (1), pp. 198-205 (Jul. 18, 2003).
Greenspan et al., "Defining epitopes: It's not as easy as it seems," Nature Biotechnology, 17, pp. 936-937 (Oct. 1999).
Lazar et al., "Transforming Growth Factor a: Mutation of Aspartic Acid 47 and Leucine 48 Results in Different Biological Activities," Molecular and Cellular Biology, 8 (3), pp. 1247-1252 (Mar. 1988).
Maccallum et al., "Antibody-antigen Interactions: Contact Analysis and Binding Site Topography," Journal of Molecular Biology, 262 (5), pp. 732-745 (Oct. 11, 1996).
Sela-Culang et al., "The structural basis of antibody-antigen recognition," Frontiers in Immunology, 4 (302), pp. 1-13 (Oct. 2013).
Vajdos et al., "Comprehensive Functional Maps of the Antigen-binding Site of an Anti-ErbB2 Antibody Obtained with Shotgun Scanning Mutagenesis," Journal of Molecular Biology, 320 (2), pp. 415-428 (Jul. 5, 2002).

\* cited by examiner

```
         360        370        380        390        400
SPYQIHFTKT PKYFKPGMPF DLMVFVTNPD GSPAYRVPVA VQGEDTVQSL 410        420        430        440        450
TQGDGVAKLS INTHPSQKPL SITVRTKKQE LSEAEQATRT MQALPYSTVG 460        470        480        490        500
NSNNYLHLSV LRTELRPGET LNVNFLLRMD RAHEAKIRYY TYLIMNKGRL
```

ANTI-C3 ANTIBODIES AND ANTIGEN-BINDING FRAGMENTS THEREOF AND THEIR USES FOR TREATING EYE OR OCULAR DISEASES

CROSS-REFERENCE TO RELATED APPLICATION

This application claims the benefit of and priority to U.S. Provisional Patent Application No. 63/292,513 filed on Dec. 22, 2021, which is incorporated herein by reference in its entirety.

SEQUENCE LISTING

The instant application contains a Sequence Listing which has been submitted electronically in XML format and is hereby incorporated by reference in its entirety. Said sequence listing, created on Nov. 11, 2022, is named "105218-03-5012-US_ST26_Sequence_Listing.xml" and is approximately 83 kilobytes in size.

FIELD OF THE INVENTION

This invention generally relates to antibodies and fragments thereof that target complement C3. More specifically, anti-C3 antibodies and antigen-binding fragments thereof and methods of use for the treatment of various diseases or disorders are disclosed. Pharmaceutical compositions comprising the anti-C3 antibody are also disclosed.

BACKGROUND OF THE INVENTION

Age-related macular degeneration (AMD) is generally divided into two main classes, dry AMD and wet AMD. Dry AMD, also known as nonexudative AMD, is characterized by the presence of drusen (yellow deposits) in the macular region. Wet AMD, also known as exudative AMD or neovascular AMD, is characterized by the growth of abnormal blood vessels from the choroid underneath the macula. This process is also called choroidal neovascularization and the new blood vessels may leak fluid, such as blood, into and around the retina.

Geographic atrophy (GA) also known as atrophic AMD or advanced dry AMD, is an advanced form of AMD characterized by loss of the retinal pigment epithelium (RPE) and photoreceptors in the macula. Irreversible visual acuity loss occurs once GA involves the central fovea. Patients with earlier stages of GA typically experience visual function deficits even before visual acuity is affected.

The underlying pathophysiology of geographic atrophy is not completely understood; however, dysregulation of complement activity is thought to be a contributing factor. Several complement activation products, including C3a, C5a, C5b-9 and complement factor H (CFH) have shown elevated levels in vitreous samples, Bruch's membrane, and other parts of the choroid of GA patients compared with controls. In addition, complement inhibitors like CD59 (a membrane-bound inhibitor of membrane attack complex (MAC) formation) and membrane cofactor protein (MCP) (a membrane-bound complement regulator that has cofactor activity for complement factor I (CFI)) have been reported at reduced levels in GA.

One major challenge in the treatment of GA is that the observed dysregulation of complement activity occurs in the deeper layers of the retina. At present, there are no appropriate treatments for GA, with acceptable efficacy and patient acceptance and compliance.

There is thus still an unfulfilled need for new and improved therapeutic approaches for efficiently treating eye or ocular disease such as geographic atrophy and restoring or preventing loss of vision in patients suffering from such disease.

SUMMARY OF THE INVENTION

The innate human system is composed of the complement pathway. The complement pathway serves to defend against pyogenic bacterial infection bridging innate and adaptive immunity; and disposing of products of immune complexes and inflammatory injury. The complement is a system of more than 30 proteins involved in cascade reactions in plasma and cell surfaces. The complement system and its complement components are involved in various immune processes. For example, complement C5b-9 complex, also termed the terminal complex or the membrane attack complex (MAC), plays an important role in cell death by inducing membrane permeability damages.

There are three known complement activation pathways: the classical, lectin, and alternative pathways. All three pathways lead to the cleavage of C3 by C3 convertase and subsequent cleavage of C5 by the C5 convertase, releasing C3a, C3b, C5a, and C5b.

Complement C3 is a large protein composed of 13 different domains and a molecular size of 185 kilodaltons. During complement activation, C3 undergoes proteolytic cleavage and structural modifications at different sites. The C3 derived fragments exert different effector functions and form convertases that fuel amplification loops to the three complement pathways. For avoidance of doubt, and unless otherwise indicated, C3 as used herein refers to human of complement component 3 of UniProt P01024 and the nucleic acid sequence encoding that protein. The sequence of the human complement C3 is depicted in SEQ ID NO: 47 and is available online under the UniProt P01024.

C3b is derived from native C3 and is the larger of two elements formed by the cleavage of C3.

The Classical pathway and Lectin pathway C3 convertase, C4bC2a, cleaves full length C3 into C3b and the anaphylatoxin C3a. The Alternative pathway also generates C3b and C3a, but utilizes the Alternative pathway C3 convertase, C3bBb. Furthermore, additional C3 degradation products may be generated in the complement pathways. Complement Factor I (CFI) is a plasma serine protease that is able to permanently inactivate C3b to iC3b. iC3b then is cleaved into further fragments (C3dg and C3c) by CFI. An additional C3 proteolytic product, C3d, binds complement receptor 2 (CR2) and may play an important role in the cell-cycle control of B cells. Along with the C3-derived protein products, the complement pathways include, but are not limited to, C1, C2, C4, C4b, C4a, C5, C5b, C5a, C6, C7, C8, C9, C1q, C1r, C1s, Factor B, Factor D, Factor P, Factor H, Factor I, CD46 (MCP), CD55 (DAF), CD59 (MAC-IP), CR1 (CD35), CR2 (CD21), CR3, CR4, C3aR, C5aR1, C5aR2, CRIg, C4BP α-chain, C4BP β-chain, ficolin-1, mannose-binding lectin (MBL), MBL-associated serine protease-1 (MASP-1), and MBL-associated serine protease-2 (MASP-2). The complement pathway and various complement pathway components are described in further detail in Noris et al. Semin Nephrol. 2013; 33(6): 479-492.

Recent work has demonstrated that complement components C3 and C5 are principal constituents of drusen in patients with AMD. Their presence as well as that of the membrane attack complex (MAC) C5b-9 and other acute phase reactant proteins in RPE cells overlying drusen has been speculated to be involved in the process that can trigger complement activation and formation of MAC.

It has been shown that in patients suffering from GA, an increased and uncontrolled activation of the complement system in the choroid and retina results in the destruction of the choriocapillaris, damage and loss of both RPE cells and photoreceptors. The inventors have hypothesized and illustrated that neutralization of C3 in the retina blocks the amplification loop of the alternative complement pathway and thereby reduces the generation of the cell toxic membrane attack complex and the generation of the proinflammatory complement components (C3a, C3b, iC3b, C5a), improving the clinical outcome of patients suffering from GA.

It is however particularly challenging to treat eye or ocular diseases as delivery of therapeutic agents to the eye is limited due to several barriers, including, but not limited to, blood-retinal-barriers, such as the RPE. The ability to penetrate the RPE and enter the choroid of the eye would enhance the therapeutic potential of drugs.

To address this clinical situation, the inventors developed new antibodies and fragments thereof capable of penetrating the RPE and Bruch's membrane of the choroid region of the eye, thereby targeting complement C3 in the choroid region. The antibodies and fragments thereof of present invention show enhanced features to improve the clinical outcome of patients suffering from eye or ocular diseases.

In one aspect, the present invention provides an anti-C3 antibody or an antigen-binding fragment thereof comprising a variable heavy chain (VH), and a variable light chain (VL),
wherein the VH comprises a CDR-H1 sequence of SEQ ID NO: 1, a CDR-H2 sequence selected from the group consisting of SEQ ID NO: 2 and 15, a CDR-H3 sequence of SEQ ID NO: 3; and
wherein the VL comprises a CDR-L1 sequence of SEQ ID NO: 4, a CDR-L2 sequence selected from the group consisting of SEQ ID NO: 5 and 18, and a CDR-L3 sequence of SEQ ID NO: 6.

In one embodiment, the present invention provides an anti-C3 antibody or an antigen-binding fragment thereof comprising:
a heavy chain variable region comprising an amino acid sequence at least 80%, at least 90%, at least 95%, at least 98%, or at least 99% identical to the amino acid sequence of SEQ ID NO: 20, 22 or 24; and
a light chain variable region comprising an amino acid sequence at least 80%, at least 90%, at least 95%, at least 98%, or at least 99% identical to the amino acid sequence of SEQ ID NO: 21, 23 or 25.

In another embodiment, the present invention provides an anti-C3 antibody or an antigen-binding fragment thereof comprising:
a heavy chain variable region comprising an amino acid sequence at least 80%, at least 90%, at least 95%, at least 98%, or at least 99% identical to the amino acid sequence of SEQ ID NO: 20, 22 or 24; and
a light chain variable region comprising an amino acid sequence at least 80%, at least 90%, at least 95%, at least 98%, or at least 99% identical to the amino acid sequence of SEQ ID NO: 21, 23 or 25;
wherein:
the VH comprises a CDR-H1 sequence of SEQ ID NO: 1, a CDR-H2 sequence selected from the group consisting of SEQ ID NO: 2 and 15, a CDR-H3 sequence of SEQ ID NO: 3; and
the VL comprises a CDR-L1 sequence of SEQ ID NO: 4, a CDR-L2 sequence selected from the group consisting of SEQ ID NO: 5 and 18, and a CDR-L3 sequence of SEQ ID NO: 6.

In another embodiment, the present invention provides an anti-C3 antibody or an antigen-binding fragment thereof comprising:
a heavy chain variable region comprising an amino acid sequence at least 80%, at least 90%, at least 95%, at least 98%, or at least 99% identical to the amino acid sequence of SEQ ID NO: 20; and
a light chain variable region comprising an amino acid sequence at least 80%, at least 90%, at least 95%, at least 98%, or at least 99% identical to the amino acid sequence of SEQ ID NO: 21;
wherein:
the VH comprises a CDR-H1 sequence of SEQ ID NO: 1, a CDR-H2 sequence of SEQ ID NO: 2, and a CDR-H3 sequence of SEQ ID NO: 3; and
the VL comprises a CDR-L1 sequence of SEQ ID NO: 4, a CDR-L2 sequence of SEQ ID NO: 5, and a CDR-L3 sequence of SEQ ID NO: 6.

In another embodiment, the present invention provides an anti-C3 antibody or an antigen-binding fragment thereof comprising:
a heavy chain variable region comprising an amino acid sequence at least 80%, at least 90%, at least 95%, at least 98%, or at least 99% identical to the amino acid sequence of SEQ ID NO: 22; and
a light chain variable region comprising an amino acid sequence at least 80%, at least 90%, at least 95%, at least 98%, or at least 99% identical to the amino acid sequence of SEQ ID NO: 23;
wherein:
the VH comprises a CDR-H1 sequence of SEQ ID NO: 1, a CDR-H2 sequence of SEQ ID NO: 15, and a CDR-H3 sequence of SEQ ID NO: 3; and the VL comprises a CDR-L1 sequence of SEQ ID NO: 4, a CDR-L2 sequence of SEQ ID NO: 5, and a CDR-L3 sequence of SEQ ID NO: 6.

In another embodiment, the present invention provides an anti-C3 antibody or an antigen-binding fragment thereof comprising:
a heavy chain variable region comprising an amino acid sequence at least 80%, at least 90%, at least 95%, at least 98%, or at least 99% identical to the amino acid sequence of SEQ ID NO: 24; and
a light chain variable region comprising an amino acid sequence at least 80%, at least 90%, at least 95%, at least 98%, or at least 99% identical to the amino acid sequence of SEQ ID NO: 25;
wherein:
the VH comprises a CDR-H1 sequence of SEQ ID NO: 1, a CDR-H2 sequence of SEQ ID NO: 15, and a CDR-H3 sequence of SEQ ID NO: 3; and the VL comprises a CDR-L1 sequence of SEQ ID NO: 4, a CDR-L2 sequence of SEQ ID NO: 18, and a CDR-L3 sequence of SEQ ID NO: 6.

In one embodiment, the invention provides an anti-C3 antibody or an antigen-binding fragment thereof comprising: a heavy chain variable region comprising the amino acid sequences of SEQ ID NO: 20, 22 or 24; and a light chain variable region comprising the amino acid sequence of SEQ ID NO: 21, 23 or 25.

In a further embodiment, the invention provides an anti-C3 antibody or an antigen-binding fragment thereof comprising:

a. a variable heavy chain and a variable light chain comprising the amino acid sequences of SEQ ID NO: 20 and SEQ ID NO: 21, respectively;
b. a variable heavy chain and a variable light chain comprising the amino acid sequences of SEQ ID NO: 22 and SEQ ID NO: 23, respectively; or
c. a variable heavy chain and a variable light chain comprising the amino acid sequences of SEQ ID NO: 24 and SEQ ID NO: 25, respectively.

In one embodiment, the anti-C3 antibody or the antigen-binding fragment thereof according to the invention is selected from the group consisting of a single chain variable fragment (scFv), a Fab fragment, a Fab' fragment, a Fv fragment, a diabody, a small antibody mimetic.

In one embodiment, the anti-C3 antibody or the antigen-binding fragment thereof according to the invention is a single chain variable fragment (scFv) comprising, or consisting of, a variable heavy chain and a variable light chain that are linked by a polypeptide linker. The scFv may comprise, or consist of, from N- to C-terminus, the variable light chain, linker, and variable heavy chain. The scFv may comprise, or consist of, from N- to C-terminus, the variable heavy chain, linker, and variable light chain. The linker may comprise a polypeptide selected SEQ ID NOs: 43-46 and 56-65, preferably SEQ ID NO: 46.

In an alternative embodiment the anti-C3 antibody or the antigen-binding fragment thereof is selected from the groups consisting of a single domain antibody, such as a sdAb, a sdFv, a nanobody, a V-Nar and a VHH. In this particular embodiment, said anti-C3 antibody or the antigen-binding fragment thereof comprises a variable heavy chain. In one embodiment, said variable heavy chain comprises a CDR-H1 sequence of SEQ ID NO: 1, a CDR-H2 sequence selected from the group consisting of SEQ ID NO: 2 and 15, a CDR-H3 sequence of SEQ ID NO: 3. In another embodiment, said variable heavy chain comprises the amino acid sequences of SEQ ID NO: 20, 22 or 24.

In one embodiment, said antigen binding fragment is a single chain variable fragment (scFv), more preferably a humanized scFv.

In a further embodiment, the anti-C3 antibody or the antigen-binding fragment thereof according to the invention is a single chain variable fragment comprising a polypeptide having at least 80%, at least 90%, at least 95%, at least 98%, or at least 99% identity to a sequence selected from the group consisting of SEQ ID NO: 26, 27, 28, 29, 30 and 31.

In a further embodiment, the anti-C3 antibody or the antigen-binding fragment thereof according to the invention is a single chain variable fragment comprising one sequence selected from the group consisting of SEQ ID NO: 26, 27, 28, 29, 30 and 31.

In a further embodiment, the anti-C3 antibody or the antigen-binding fragment thereof according to the invention is a single chain variable fragment consisting of one sequence selected from the group consisting of SEQ ID NO: 26, 27, 28, 29, 30 and 31.

In one embodiment, the anti-C3 antibody or the antigen-binding fragment thereof according to the invention is capable of inhibiting the pathways of complement activation, including the Classical pathway (CP), the Lectin pathway (LP), and the Alternative pathway (AP). In certain embodiments, the anti-C3 antibody or the antigen-binding fragment thereof according to the invention is capable of approximately equivalent inhibition of the activity of the CP, LP and AP complement pathways. For example, but in no way limiting, the anti-C3 antibody or the antigen-binding fragment thereof is capable of inhibiting the activity of the CP pathway by at least 80%, capable of inhibiting the activity of the LP by at least 80%, and capable of inhibiting the activity of the AP by at least 80%. In certain embodiments, the inhibition of the activity of the CP, LP and AP complement pathways is at least 80%, at least 85%, at least about 90%, or at least about 95%.

In one embodiment, the anti-C3 antibody or the antigen-binding fragment thereof according to the invention is capable of binding complement C3 and C3b.

In one embodiment, the anti-C3 antibody or the antigen-binding fragment thereof according to the invention is capable of preventing the formation of C3 convertase.

In one embodiment, the anti-C3 antibody or the antigen-binding fragment thereof according to the invention is capable of penetrating Bruch's membrane.

In a particular embodiment, the anti-C3 antibody or the antigen-binding fragment thereof according to the invention binds to human C3 at a $K_D<50$ nM, preferably at a $K_D<15$ nM, preferably at a $K_D<10$ nM, preferably at a $K_D<7$ nM, preferably at a $K_D<1$ nM, preferably at a $K_D<0.5$ nM, preferably at a $K_D<0.2$ nM, preferably at a $K_D<0.15$ nM, preferably at a $K_D<0.10$ nM, preferably at a $K_D<0.05$ nM, preferably at a $K_D<0.04$ nM, more preferably at a $K_D<0.03$ nM.

In another embodiment, the anti-C3 antibody or the antigen-binding fragment thereof according to the invention binds to human C3b at a $K_D<50$ nM, preferably at a $K_D<15$ nM, preferably at a $K_D<10$ nM, preferably at a $K_D<7$ nM, preferably at a $K_D<1$ nM, preferably at a $K_D<0.5$ nM, preferably at a $K_D<0.2$ nM, preferably at a $K_D<0.15$ nM, preferably at a $K_D<0.10$ nM, more preferably at a $K_D<0.05$ nM.

In one embodiment, the anti-C3 antibody or the antigen-binding fragment thereof according to the invention has approximately equivalent binding affinity for C3 and C3b.

In one embodiment, the anti-C3 antibody or the antigen-binding fragment thereof according to the invention has a binding affinity for C3a, iC3b, C4, C4b, C5, and/or C5b of about $10^{-4}$ M or lower (i.e., weaker).

In a further embodiment, the anti-C3 antibody or the antigen-binding fragment thereof according to the invention has weaker binding affinity for C3a, iC3b, C4, C4b, C5, and/or C5b compared to the binding affinity for C3 and C3b.

In a particular embodiment, the anti-C3 antibody or the antigen-binding fragment thereof according to the invention has no binding affinity for C3a, iC3b, C4, C4b, C5, and/or C5b. As used herein, "no binding affinity" refers to no detectable binding affinity relative to background with one or more binding affinity assays known in the art, such as, but not limited to, an ELISA assay.

In certain embodiments, the antibody of the invention is capable of binding complement C3 in a manner to prevent the formation of C3 convertase. In a particular embodiment, the antibody of the invention inhibits the activity of C3 convertase. In a particular embodiment, the antibody of the invention is capable of inhibiting the C3 convertase amplification loop.

In one embodiment, the anti-C3 antibody or the antigen-binding fragment thereof according to the invention is capable of inhibiting choroidal C3 activity.

In certain embodiments, the anti-C3 antibody of the invention are expected to have better efficacy and safety in treating GA or other eye or ocular disease compared to other therapies due to the following properties recited below.

In a preferred embodiment, the anti-C3 antibody or the antigen-binding fragment thereof according to the invention is capable of binding an epitope on complement C3, wherein such binding prevents the formation of C3 convertase.

In one embodiment, the present invention provides an anti-C3 antibody or an antigen-binding fragment thereof that binds to at least one amino acid residue within amino acid regions as set forth in SEQ ID NO: 47. In a preferred embodiment, the present invention provides an anti-C3 antibody or an antigen-binding fragment thereof that binds the amino acid regions as set forth in SEQ ID NO: 48.

In one aspect, the invention provides an anti-C3 antibody or an antigen-binding fragment thereof that binds to at least one amino acid residue within residues from amino acid 366 to amino acid 478 of the human Complement C3 as set forth in SEQ ID NO: 47.

In one embodiment, the invention provides an anti-C3 antibody or an antigen-binding fragment thereof that binds to at least one amino acid residue selected from the group consisting of residues 366, 392-396, 413-421, 425, 427, 442, 453 and 478 of the human Complement C3 as set forth in SEQ ID NO: 47.

In one embodiment, the invention provides an anti-C3 antibody or an antigen-binding fragment thereof that binds to all of the amino acid residues 366, 392-396, 413-421, 425, 427, 442, 453 and 478 of the human Complement C3 as set forth in SEQ ID NO: 47.

In one aspect, the present invention provides an anti-C3 antibody or an antigen-binding fragment thereof for use as a medicament.

In one embodiment, the present invention provides an anti-C3 antibody or an antigen-binding fragment thereof for use in the treatment or prevention of a retinal or eye disease. Preferably, said retinal or eye disease is a complement C3-mediated disease or disorder. More preferably, said disease refers to any disorder in which the onset, progression or the persistence of the symptoms or disease requires the participation of C3.

In another embodiment, the present invention relates to a method for treating one or more retinal or eye diseases, comprising administering a pharmaceutically effective amount of an antibody or an antigen-binding fragment according to a patient in need thereof.

In one aspect, the present invention provides use of said anti-C3 antibody or said antigen-binding fragment thereof for the manufacture of a medicament for treating or preventing an eye or ocular disease.

In one aspect, the present invention provides an anti-C3 antibody or an antigen-binding fragment thereof for use in the treatment or prevention of a disease is selected from the group consisting of selected from the group consisting of retinopathy, proliferative retinopathy (PR) such as retinopathy of prematurity, ischemic retinopathy, diabetic retinopathy (DR) including proliferative diabetic retinopathy (PDR) and non-proliferative diabetic retinopathy, diabetic macular edema (DME), diabetic macular ischemia (DMI), age-related macular degeneration (AMD) including dry AMD and wet AMD, geographic atrophy (GA), retinitis pigmentosa, inherited retinal dystrophy, myopic degeneration, retinal vein occlusions, retinal artery occlusions, endophthalmitis, uveitis, cystoid macular edema, choroidal neovascular membrane secondary to any retinal diseases, optic neuropathies, glaucoma, retinal detachment, toxic retinopathy, radiation retinopathy, traumatic retinopathy, drug-induced retinal vasculopathy, retinal neovascularisation, polypoidal choroidal vasculopathy, retinal vasculitis, retinal microaneurysm, retrolental fibroplasia, chorioretinitis, Fuch's dystrophy, macular telangiectasia, usher syndrome, Paroxysmal nocturnal hemoglobinuria (PNH) and Stargardt disease.

In another embodiment, the present invention provides an anti-C3 antibody or an antigen-binding fragment thereof for use in the treatment or prevention of a disease selected from the group consisting of age-related macular degeneration, geographic atrophy, neovascular glaucoma, and diabetic retinopathy. In yet a preferred embodiment, the present invention provides an anti-C3 antibody or an antigen-binding fragment thereof for use in the treatment or prevention of geographic atrophy.

In one aspect, the antibody of the invention inhibits the activity of the complement Classical pathway (CP), Lectin pathway (LP), and Alternative pathway (AP). Thus, the present invention provides an anti-C3 antibody or an antigen-binding fragment thereof for use in a method of treating an or eye or ocular disease by inhibiting the activity of the complement Classical pathway (CP), Lectin pathway (LP), and Alternative pathway (AP). The present invention also provides an antigen binding protein or fragment thereof as described above for use in a method of treating a complement C3-mediated disease or disorder, by inhibiting the activity of choroidal-localized complement C3.

In one embodiment, the present invention provides a method of diagnosing disorders associated with Complement C3 in a biological sample using the anti-C3 antibody or the antigen-binding fragment thereof according to present invention.

In one aspect, the present invention provides a pharmaceutical composition comprising an anti-C3 antibody or an antigen-binding fragment thereof and a pharmaceutically acceptable carrier.

In one embodiment, the present invention provides an anti-C3 antibody or an antigen-binding fragment thereof or a pharmaceutical composition comprising an anti-C3 antibody or an antigen-binding fragment thereof, wherein said antibody or an antigen-binding fragment thereof is administered by a parenteral route, intravenous route, intravitreal (IVT) route or subcutaneous route of administration, preferably by intravitreal route.

In one embodiment, the present invention provides a pharmaceutical composition comprising a polynucleotide or polynucleotides encoding an antibody or an antigen-binding fragment according to present invention and a pharmaceutically acceptable carrier.

In one embodiment, the present invention provides an isolated polynucleotide or polynucleotides encoding an antibody or an antigen-binding fragment according to the invention.

In one aspect, the present invention provides an isolated polynucleotide or polynucleotides comprising:
- a sequence encoding a heavy chain variable region set forth in SEQ ID NO: 20, SEQ ID NO: 22, or SEQ ID NO: 24, and/or
- a sequence encoding a light chain variable region set forth in SEQ ID NO: 21, SEQ ID NO: 23 or SEQ ID NO: 25.

In one aspect, the present invention provides an isolated polynucleotide comprising a sequence encoding an scFv set forth in SEQ ID NO: 26, SEQ ID NO: 27, SEQ ID NO: 28, SEQ ID NO: 29, SEQ ID NO: 30, or SEQ ID NO: 31.

In one embodiment, the present invention provides an expression vector comprising an isolated polynucleotide or polynucleotides comprising a sequence encoding a sequence encoding a heavy chain variable region set forth in SEQ ID NO: 20, SEQ ID NO: 22, or SEQ ID NO: 24, and/or a sequence encoding a light chain variable region set forth in SEQ ID NO: 21, SEQ ID NO: 23 or SEQ ID NO: 25.

In one embodiment, the present invention provides an expression vector comprising an isolated polynucleotide comprising a sequence encoding a sequence encoding an scFv set forth in SEQ ID NO: 26, SEQ ID NO: 27, SEQ ID NO: 28, SEQ ID NO: 29, SEQ ID NO: 30, or SEQ ID NO: 31.

In one embodiment, the present invention provides a viral vector comprising an isolated polynucleotide or polynucleotides comprising a sequence encoding a heavy chain variable region set forth in SEQ ID NO: 20, SEQ ID NO: 22, or SEQ ID NO: 24, and/or a sequence encoding a light chain variable region set forth in SEQ ID NO: 21, SEQ ID NO: 23 or SEQ ID NO: 25.

In one embodiment, the present invention provides a viral vector comprising an isolated polynucleotide comprising a sequence encoding an scFv set forth in SEQ ID NO: 26, SEQ ID NO: 27, SEQ ID NO: 28, SEQ ID NO: 29, SEQ ID NO: 30, or SEQ ID NO: 31.

In one embodiment, the present invention provides a host cell comprising an expression vector or an isolated polynucleotide or polynucleotides comprising a sequence encoding a heavy chain variable region set forth in SEQ ID NO: 20, SEQ ID NO: 22, or SEQ ID NO: 24, and/or a sequence encoding a light chain variable region set forth in SEQ ID NO: 21, SEQ ID NO: 23 or SEQ ID NO: 25.

In one embodiment, the present invention provides a host cell comprising an expression vector or an isolated polynucleotide comprising a sequence encoding an scFv set forth in SEQ ID NO: 26, SEQ ID NO: 27, SEQ ID NO: 28, SEQ ID NO: 29, SEQ ID NO: 30, or SEQ ID NO: 31.

In one embodiment, the present invention provides a method for producing an anti-C3 antibody or an antigen-binding fragment thereof comprising obtaining a host cell comprising an expression vector or an isolated polynucleotide or polynucleotides comprising a sequence encoding a heavy chain variable region as set forth in SEQ ID NO: 20, SEQ ID NO: 22, or SEQ ID NO: 24, and/or a sequence encoding a light chain variable region as set forth in SEQ ID NO: 21, SEQ ID NO: 23 or SEQ ID NO: 25; and cultivating the host cell.

In one embodiment, the present invention provides a method for producing an anti-C3 antibody or antigen-binding fragment thereof comprising obtaining a host cell comprising an expression vector or an isolated polynucleotide comprising a sequence encoding an scFv set forth in SEQ ID NO: 26, SEQ ID NO: 27, SEQ ID NO: 28, SEQ ID NO: 29, SEQ ID NO: 30, or SEQ ID NO: 31.

In one embodiment, the method for producing an anti-C3 antibody or an antigen-binding fragment thereof further comprises recovering and purifying the anti-C3 antibody or the antigen-binding fragment thereof.

BRIEF DESCRIPTION OF THE DRAWINGS

FIG. 1: Better retinal penetration with scFv after equimolar IVT injection in Cynomolgus monkey.

FIG. 2: This figure illustrates the binding of Clone I to human Complement C3.

DETAILED DESCRIPTION OF THE INVENTION

Definitions

Figure 1A:
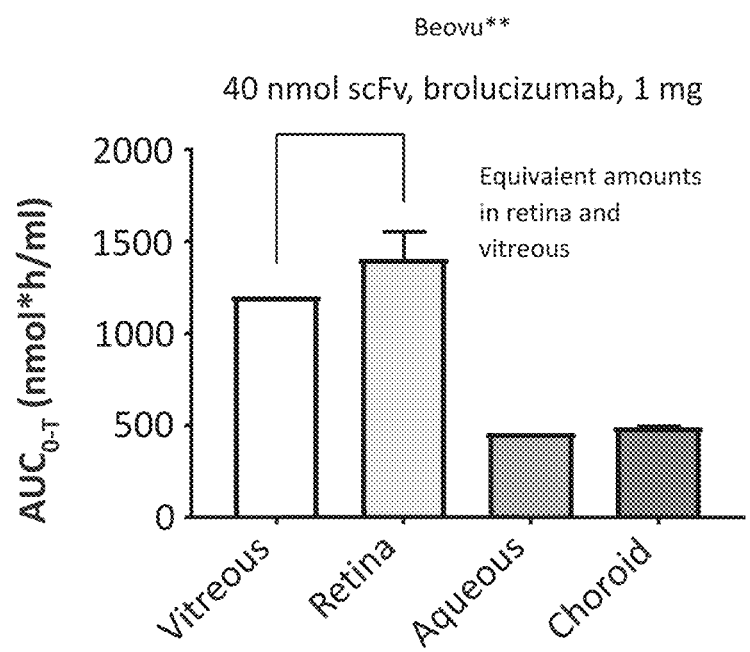
FIG. 1A depicts the retinal exposure level of a scFv intravitreal injection (40 nmol scFv, brolucizumab, 1 mg). The data are adapted from Brolucizumab BLA.

The generalized structure of antibodies or immunoglobulin is well known to those of skill in the art, these molecules are heterotetrameric glycoproteins, typically of about 150,000 daltons, composed of two identical light (L) chains and two identical heavy (H) chains. Each light chain is covalently linked to a heavy chain by one disulfide bond to form a heterodimer, and the heterotrimeric molecule is formed through a covalent disulfide linkage between the two identical heavy chains of the heterodimers. Although the light and heavy chains are linked together by one disulfide bond, the number of disulfide linkages between the two heavy chains varies by immunoglobulin isotype. Each heavy and light chain also has regularly spaced intrachain disulfide bridges. Each heavy chain has at the amino-terminus a variable domain ($V_H$=variable heavy chain), followed by three or four constant domains ($C_{H1}$, $C_{H2}$, $C_{H3}$, and $C_{H4}$), as well as a hinge region between $C_{H1}$ and $C_{H2}$. Each light chain has two domains, an amino-terminal variable domain ($V_L$=variable light chain) and a carboxy-terminal constant domain ($C_L$). The $V_L$ domain associates non-covalently with the $V_H$ domain, whereas the CL domain is commonly covalently linked to the $C_{H1}$ domain via a disulfide bond. Particular amino acid residues are believed to form an interface between the light and heavy chain variable domains (Chothia et al., 1985, J. Mol. Biol. 186:651-663.)

Certain domains within the variable domains differ extensively between different antibodies, i.e., are "hypervariable." These hypervariable domains contain residues that are directly involved in the binding and specificity of each particular antibody for its specific antigenic determinant. Hypervariability, both in the light chain and the heavy chain variable domains, is concentrated in three segments known as complementarity determining regions (CDRs) or hypervariable loops (HVLs). CDRs are defined by sequence comparison in Kabat et al., 1991, In: Sequences of Proteins of Immunological Interest, 5th Ed. Public Health Service, National Institutes of Health, Bethesda, Md., whereas HVLs are structurally defined according to the three-dimensional structure of the variable domain, as described by Chothia and Lesk, 1987, J. Mol. Biol. 196: 901-917.

The precise amino acid sequence boundaries of a given CDR or FR can be further determined using additional nomenclature such as AHo numbering scheme as described in Honegger A and Pluckthun A, "Yet another numbering scheme for immunoglobulin variable domains: an automatic modeling and analysis tool," J Mol Biol, 2001 Jun. 8; 309(3):657-70, or "IMGT" numbering scheme) as described in Lefranc M P et al., "IMGT unique numbering for immunoglobulin and T cell receptor variable domains and Ig superfamily V-like domains," Dev Comp Immunol, 2003 January; 27(1):55-77.

The three CDRs within each of the heavy and light chains are separated by framework regions (FR), which contain sequences that tend to be less variable. From the amino terminus to the carboxy terminus of the heavy and light chain variable domains, the FRs and CDRs are arranged in the order: FR1, CDR1, FR2, CDR2, FR3, CDR3, and FR4. The largely β-sheet configuration of the FRs brings the CDRs within each of the chains into close proximity to each other as well as to the CDRs from the other chain. The resulting conformation contributes to the antigen binding site (see Kabat et al., 1991, NIH Publ. No. 91-3242, Vol. I, pages 647-669), although not all CDR residues are necessarily directly involved in antigen binding.

FR residues and Ig constant domains may contribute to antigen binding and/or mediate antibody effector function. Some FR residues are thought to have a significant effect on antigen binding in at least three ways: by noncovalently binding directly to an epitope, by interacting with one or more CDR residues, and by affecting the interface between the heavy and light chains. The constant domains are not directly involved in antigen binding but mediate various Ig effector functions, such as participation of the antibody in antibody-dependent cellular cytotoxicity (ADCC), complement-dependent cytotoxicity (CDC) and antibody-dependent cellular phagocytosis (ADCP).

The light chains of vertebrate immunoglobulins are assigned to one of two clearly distinct classes, kappa (κ) and lambda (λ), based on the amino acid sequence of the constant domain. By comparison, the heavy chains of mammalian immunoglobulins are assigned to one of five major classes, according to the sequence of the constant domains: IgA, IgD, IgE, IgG, and IgM. IgG and IgA are further divided into subclasses (isotypes), e.g., $IgG_1$, $IgG_2$, $IgG_3$, $IgG_4$, $IgA_1$, and $IgA_2$, respectively. The heavy chain constant domains that correspond to the different classes of immunoglobulins are called α, δ, ε, γ, and μ, respectively. The subunit structures and three-dimensional configurations of the classes of native immunoglobulins are well known.

The terms, "antibody", "anti-C3 antibody", "humanized anti-C3 antibody", and "variant humanized anti-C3 antibody" are used herein in the broadest sense and specifically encompass monoclonal antibodies (including full length monoclonal antibodies), multispecific antibodies (e.g., bispecific antibodies), and antibody fragments such as variable domains and other portions of antibodies that exhibit a desired biological activity, e.g., binding to C3.

The term "monoclonal antibody" (mAb) refers to an antibody of a population of substantially homogeneous antibodies; that is, the individual antibodies in that population are identical except for naturally occurring mutations that may be present in minor amounts. Monoclonal antibodies are highly specific, being directed against a single antigenic determinant, an "epitope". Therefore, the modifier "monoclonal" is indicative of a substantially homogeneous population of antibodies directed to the identical epitope and is not to be construed as requiring production of the antibody by any particular method. It should be understood that monoclonal antibodies can be made by any technique or methodology known in the art; including e.g., the hybridoma method (Kohler et al., 1975, Nature 256:495), or recombinant DNA methods known in the art (see, e.g., U.S. Pat. No. 4,816,567), or methods of isolation of monoclonal recombinantly produced using phage antibody libraries, using techniques described in Clackson et al., 1991, Nature 352: 624-628, and Marks et al., 1991, J. Mol. Biol. 222: 581-597.

Chimeric antibodies consist of the heavy and light chain variable regions of an antibody from one species (e.g., a non-human mammal such as a mouse) and the heavy and light chain constant regions of another species (e.g., human) antibody and can be obtained by linking the DNA sequences encoding the variable regions of the antibody from the first species (e.g., mouse) to the DNA sequences for the constant regions of the antibody from the second (e.g. human) species and transforming a host with an expression vector containing the linked sequences to allow it to produce a chimeric antibody. Alternatively, the chimeric antibody also could be one in which one or more regions or domains of the heavy and/or light chain is identical with, homologous to, or a variant of the corresponding sequence in a monoclonal antibody from another immunoglobulin class or isotype, or from a consensus or germline sequence. Chimeric antibodies can include fragments of such antibodies, provided that the antibody fragment exhibits the desired biological activity of its parent antibody, for example binding to the same epitope (see, e.g., U.S. Pat. No. 4,816,567; and Morrison et al., 1984, Proc. Natl. Acad. Sci. USA 81: 6851-6855).

The terms, "antibody fragment", "antigen-binding fragment", "anti-C3 antibody fragment", "humanized anti-C3 antibody fragment", "variant humanized anti-C3 antibody fragment" refer to a portion of a full length anti-C3 antibody, in which a variable region or a functional capability is retained, for example, specific C3 epitope binding. Examples of antibody fragments or antigen-binding fragments include, but are not limited to, a Fab, Fab', $F(ab')_2$, Fd, Fv, scFv and scFv-Fc fragment, a diabody, a linear antibody, a single-chain antibody, a minibody, a diabody formed from antibody fragments, single domain antibodies (e.g., sdAb, sdFv, nanobody, VHH) fragments and multispecific antibodies formed from antibody fragments.

Full length antibodies can be treated with enzymes such as papain or pepsin to generate useful antibody fragments. Papain digestion is used to produce two identical antigen-binding antibody fragments called "Fab" fragments, each with a single antigen-binding site, and a residual "Fc" fragment. The Fab fragment also contains the constant domain of the light chain and the $C_{H1}$ domain of the heavy chain. Pepsin treatment yields a $F(ab')_2$ fragment that has two antigen-binding sites and is still capable of cross-linking antigen.

Fab' fragments differ from Fab fragments by the presence of additional residues including one or more cysteines from the antibody hinge region at the C-terminus of the $C_{H1}$ domain. $F(ab')_2$ antibody fragments are pairs of Fab' fragments linked by cysteine residues in the hinge region. Other chemical couplings of antibody fragments are also known.

"Fv" fragment contains a complete antigen-recognition and binding site consisting of a dimer of one heavy and one light chain variable domain in tight, non-covalent association. In this configuration, the three CDRs of each variable domain interact to define an antigen-biding site on the surface of the $V_H$-$V_L$ dimer. Collectively, the six CDRs confer antigen-binding specificity to the antibody.

A "single-chain Fv" or "scFv" antibody fragment is a single chain Fv variant comprising the $V_H$ and $V_L$ domains of an antibody where the domains are present in a single polypeptide chain. The single chain Fv is capable of recognizing and binding antigen. The scFv polypeptide may optionally also contain a polypeptide linker positioned between the $V_H$ and $V_L$ domains in order to facilitate formation of a desired three-dimensional structure for antigen binding by the scFv (see, e.g., Pluckthun, 1994, In: The Pharmacology of monoclonal Antibodies, Vol. 113, Rosenburg and Moore eds., Springer-Verlag, New York, pp. 269-315). Such linkers include, but are not limited to, repeated GGGGS amino acid sequences (SEQ ID NO: 43) or variants thereof. Such scFv molecules can have the general structures: NH2-VL-linker-VH—COOH or NH2-VH-linker-VL-COOH. The scFv is generally free of antibody constant domain regions, although an scFv of the invention may be linked or attached to antibody constant domain regions (e.g., antibody Fc domain) to alter various properties of the scFv, including, but not limited to, increased serum or tissue half-life. An scFv generally has a molecular weight of about 25 kDa and a hydrodynamic radius of about 2.5 nm.

In one embodiment, antibodies and antibody fragments of the present invention are single chain antibodies (scFv) or Fab fragments. In the case of scFv antibodies, a selected VL domain can be linked to a selected VH domain in either orientation by a flexible linker. Flexible linkers, as envisaged herein, are peptide or polypeptide linkers of at least 1 amino acid in length. Preferably, the linkers are 1 to 100 amino acids in length. More preferably, the linkers are 5 to 50 amino acids in length, more preferably 10 to 40 amino acids in length, and even more preferably, the linkers are 15 to 30 amino acids in length. Non-limiting examples of often used small linkers include sequences of glycine and serine amino acids, termed GS mini-linker. Preferred examples of linker sequences are Gly/Ser linkers of different length such as $(gly_x ser_y)_z$ linkers, including $(gly_4 ser)_3$ (SEQ ID NO: 45), $(gly_4 ser)_4$ (SEQ ID NO: 46), $(gly_4 ser)$ (SEQ ID NO: 44), $(gly_4 ser)$ (SEQ ID NO: 56), $gly_3$, and $(gly_3 ser_2)_3$ (SEQ ID NO: 65). The number of amino acids in these linkers can vary, for example, they can be 4 (e.g., GGGS) (SEQ ID NO: 56), 6 (e.g., GGSGGS) (SEQ ID NO: 57), 7 (e.g., GGGSGGS) (SEQ ID NO: 58), or multiples thereof, such as e.g. two or three or more repeats of these four, six, or seven amino acids. In one embodiment, the antibody of the invention comprise a linker selected from the group consisting of sequences set forth in SEQ ID NO: 43 (GGGGS), SEQ ID NO: 44 (GGGGSGGGGS), SEQ ID NO: 45 (GGGGSGGGGSGGGGS) and SEQ ID NO: 46 (GGGGSGGGGSGGGGSGGGGS). In a particular embodiment, said linker is SEQ ID NO: 46. Said linker can be also a variant as described in Holliger et al. (1993), Proc. Natl. Acad. Sci. USA 90:6444-6448. Other linkers that can be used for the present invention are described by Alfthan et al. (1995), Protein Eng. 8:725-731, Choi et al. (2001), Eur. J. Immunol. 31:94-106, Hu et al. (1996), Cancer Res. 56:3055-3061, Kipriyanov et al. (1999), J. Mol. Biol. 293:41-56 and Roovers et al. (2001), Cancer Immunol. Immunother. 50:51-59. Further examples of linkers include the following: 7GS linker: SGGSGGS (SEQ ID NO: 59); 8GS linker: 9GS linker: GGGGSGGGS (SEQ ID NO: 60); 18GS linker: GGGGSGGGGSGGGGGGGS (SEQ ID NO: 61); 25GS linker: GGGGSGGGGSGGGGSGGGGSGGGGS (SEQ ID NO: 62); 30GS linker: GGGGSGGGGSGGGGSGGGGSGGGGSGGGGS (SEQ ID NO: 63); and 35GS linker: GGGGSGGGGSGGGGSGGGGSGGGGSGGGGSGGGGS (SEQ ID NO: 64).

In an scFv according to the present disclosure, the VL and VH arrangement can be either VL-linker-VH or VH-linker-VL, with the former orientation being the preferred one.

However, single VH or VL domain antibodies are also contemplated. In the case of Fab fragments, selected light chain variable domains VL are fused to the constant region of a human Ig kappa chain, while the suitable heavy chain variable domains VH are fused to the first (N-terminal) constant domain CH1 of a human IgG. At the C-terminus of the constant domain or at other sites of the variable or constant domain, an inter-chain disulfide bridge may be formed.

As used herein, a "VHH", "nanobody", or "heavy-chain only antibody" is an antigen binding protein comprising a single heavy chain variable domain derived from the species of the Camelidae family, which includes camels, llama, alpaca. A VHH generally has a molecular weight of about 15 kDa.

Other recognized antibody fragments include those that comprise a pair of tandem Fd segments ($V_H$-$C_{H1}$-$V_H$-$C_{H1}$) to form a pair of antigen binding regions. These "linear antibodies" can be bispecific or monospecific as described in, for example, Zapata et al. 1995, Protein Eng. 8(10):1057-1062.

A humanized antibody or a humanized antibody fragment is a specific type of chimeric antibody which includes an immunoglobulin amino acid sequence variant, or fragment thereof, which is capable of binding to a predetermined antigen and which, comprises one or more FRs having substantially the amino acid sequence of a human immunoglobulin and one or more CDRs having substantially the amino acid sequence of a non-human immunoglobulin. This non-human amino acid sequence often referred to as an "import" sequence is typically taken from an "import" antibody domain, particularly a variable domain. In general, a humanized antibody includes at least the CDRs or HVLs of a non-human antibody, inserted between the FRs of a human heavy or light chain variable domain.

The present invention describes specific humanized anti-C3 antibodies which contain CDRs derived from a murine, rabbit, llama or chimeric antibody inserted between the FRs of human germline sequence heavy and light chain variable domains. It will be understood that certain non-human FR residues (for example from murine, rabbit, llama or chimeric antibodies, etc.) may be important to the function of the humanized antibodies and therefore certain of the human germline sequence heavy and light chain variable domains residues are modified to be the same as those of the corresponding non-human sequence.

As used herein, the expressions "antibody of the invention" and the "anti-C3 antibody of the invention" refer to an antibody directed against C3, or an antigen-binding fragment thereof described herein. In one embodiment, said antibody of the invention is a scFv. In a specific embodiment, the antibody of the invention comprises a variable heavy chain (VH), and a variable light chain (VL), wherein the VH comprises a CDR-H1 sequence of SEQ ID NO: 1, a CDR-H2 sequence selected from the group consisting of SEQ ID NO: 2 and 15, a CDR-H3 sequence of SEQ ID NO: 3; and wherein the VL comprises a CDR-L1 sequence of SEQ ID NO: 4, a CDR-L2 sequence selected from the group consisting of SEQ ID NO: 5 and 18, and a CDR-L3 sequence of SEQ ID NO: 6.

In one embodiment, the invention relates to a humanized anti-C3 antibody or fragment thereof. Humanized antibodies comprise substantially of at least one, and typically two, variable domains (such as contained, for example, in Fab, Fab', F(ab')2, Fabc, and Fv fragments) in which all, or substantially all, of the CDRs correspond to those of a non-human immunoglobulin, and specifically herein, the CDRs are of rabbit origin, and the FRs are those of a human immunoglobulin consensus or germline sequence. In another aspect, a humanized anti-C3 antibody also includes at least a portion of an immunoglobulin Fc region, typically that of a human immunoglobulin. Ordinarily, the antibody will contain both the light chain as well as at least the variable domain of a heavy chain. The antibody also may include one or more of the $C_{H1}$, hinge, $C_{H2}$, $C_{H3}$, and/or $C_{H4}$ regions of the heavy chain, as appropriate.

A humanized anti-C3 antibody can be selected from any class of immunoglobulins, including IgM, IgG, IgD, IgA and IgE, and any isotype, including $IgG_1$, $IgG_2$, $IgG_3$, $IgG_4$, $IgA_1$ and $IgA_2$. For example, the constant domain can be a complement fixing constant domain where it is desired that the humanized antibody exhibits cytotoxic activity, and the isotype is typically $IgG_1$. Where such cytotoxic activity is not desirable, the constant domain may be of another isotype, e.g., $IgG_2$ or be a modified $IgG_1$ sequence lacking cytotoxic activity, e.g., containing the mutation N297A, or L234A together with L235A. An alternative humanized anti-C3 antibody can comprise sequences from more than one immunoglobulin class or isotype, and selecting particular constant domains to optimize desired effector functions is within the ordinary skill in the art. In specific embodiments, the present invention provides antibodies that are IgG1 antibodies and more particularly IgG1 antibodies characterized by a reduced effector function.

The FRs and CDRs, or HVLs, of a humanized anti-C3 antibody or fragments thereof including scFvs do not need to correspond precisely to the parental sequences. For example, one or more residues in the import CDR, or HVL, or the consensus or germline FR sequence may be altered (e.g., mutagenized) by substitution, insertion or deletion such that the resulting amino acid residue is no longer identical to the original residue in the corresponding position in either parental sequence but the antibody nevertheless retains the function of binding to C3. Such alteration typically will not be extensive and will be conservative alterations. Usually, at least 75% of the humanized antibody residues will correspond to those of the parental consensus or germline FR and import CDR sequences, more often at least 90%, and most frequently greater than 95%, or greater than 98% or greater than 99%.

The terms "consensus sequence" and "consensus antibody" refer to an amino acid sequence which comprises the most frequently occurring amino acid residue at each location in all immunoglobulins of any particular class, isotype, or subunit structure, e.g., a human immunoglobulin variable domain. The consensus sequence may be based on immunoglobulins of a particular species or of many species. A "consensus" sequence, structure, or antibody is understood to encompass a consensus human sequence as described in certain embodiments, and to refer to an amino acid sequence which comprises the most frequently occurring amino acid residues at each location in all human immunoglobulins of any particular class, isotype, or subunit structure. Thus, the consensus sequence contains an amino acid sequence having at each position an amino acid that is present in one or more known immunoglobulins, but which may not exactly duplicate the entire amino acid sequence of any single immunoglobulin. The variable region consensus sequence is not obtained from any naturally produced antibody or immunoglobulin. Kabat et al., 1991, Sequences of Proteins of Immunological Interest, 5th Ed. Public Health Service, National Institutes of Health, Bethesda, Md., and variants thereof. The FRs of heavy and light chain consensus sequences, and variants thereof, provide useful sequences for the preparation of humanized anti-C3 antibodies. See, for example, U.S. Pat. Nos. 6,037,454 and 6,054,297.

Human germline sequences are found naturally in human population. The human germline sequences correspond to antibody protein molecules encoded by the variable (V), diversity (D), and joining (J) gene segments, which are rearranged, and form recombined genes. VDJ recombination leads to generation of a large but ultimately finite number of unmutated antibody proteins, known as the germline repertoire. A combination of those germline genes generates antibody diversity. Germ line antibody sequences for the light chain of the antibody come from conserved human germline kappa or lambda v-genes and j-genes. Similarly, the heavy chain sequences come from germline v-, d- and j-genes (LeFranc, M-P, and LeFranc, G, "The Immunoglobulin Facts Book" Academic Press, 2001).

An "isolated" antibody is one that has been identified and separated and/or recovered from a component of its natural environment. Contaminant components of the antibody's natural environment are those materials that may interfere with diagnostic or therapeutic uses of the antibody, and can be enzymes, hormones, or other proteinaceous or nonproteinaceous solutes. In one aspect, the antibody will be purified to at least greater than 95% isolation by weight of antibody.

The term "antibody performance" refers to factors/properties that contribute to antibody recognition of antigen or the effectiveness of an antibody in vivo. In a preferred embodiment, it refers to the ability of the antibody to prevent cytoskeletal collapse in retinal cells. Changes in the amino acid sequence of an antibody can affect antibody properties such as folding, and can influence physical factors such as initial rate of antibody binding to antigen ($k_a$), dissociation constant of the antibody from antigen ($k_d$), affinity constant of the antibody for the antigen (Kd), conformation of the antibody, protein stability, and half-life of the antibody. As used herein, the term "affinity" refers to the strength of the interaction between an antibody's antigen binding site and the epitope to which it binds. As readily understood by those skilled in the art, an antibody or antigen binding protein affinity may be reported as a dissociation constant ($K_D$) in molarity (M). The ability of an antigen binding domain to bind to a specific antigenic determinant can be measured either through an enzyme-linked immunosorbent assay (ELISA) or other techniques familiar to one of skill in the art, e.g., surface plasmon resonance (SPR) technique (analyzed on a BIAcore instrument), e.g., conducted at 25° C. (Liljeblad et al., Glyco J 17, 323-329 (2000)), and traditional binding assays (Heeley, Endocr Res 28, 217-229 (2002)).

As used herein, the terms "identical" or "percent identity," in the context of two or more nucleic acids or polypeptide sequences, refer to two or more sequences or subsequences that are the same or have a specified percentage of nucleotides or amino acid residues that are the same, when compared and aligned for maximum correspondence. To determine the percent identity, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=# of identical positions/total # of positions (e.g., overlapping positions)×100). In some embodiments, the two sequences that are compared are the same length, optionally after gaps are introduced within the sequences, as appropriate (e.g., excluding additional sequence extending beyond the sequences being compared). For example, when variable region sequences are compared, the leader and/or constant domain sequences are not considered. For sequence comparisons between two sequences, a "corresponding" CDR refers to a CDR in the same location in both sequences (e.g., CDR-H1 of each sequence).

The determination of percent identity or percent similarity between two sequences can be accomplished using a mathematical algorithm. A preferred, non-limiting example of a mathematical algorithm utilized for the comparison of two sequences is the algorithm of Karlin and Altschul, 1990, Proc. Natl. Acad. Sci. USA 87:2264-2268, modified as in Karlin and Altschul, 1993, Proc. Natl. Acad. Sci. USA 90:5873-5877. Such an algorithm is incorporated into the NBLAST and XBLAST programs of Altschul et al., 1990, J. Mol. Biol. 215:403-410. BLAST nucleotide searches can be performed with the NBLAST program, score=100, wordlength=12, to obtain nucleotide sequences homologous to a nucleic acid encoding a protein of interest. BLAST protein searches can be performed with the XBLAST program, score=50, wordlength=3, to obtain amino acid sequences homologous to protein of interest. To obtain gapped alignments for comparison purposes, Gapped BLAST can be utilized as described in Altschul et al., 1997, Nucleic Acids Res. 25:3389-3402. Alternatively, PSI-Blast can be used to perform an iterated search which detects distant relationships between molecules (Id.). When utilizing BLAST, Gapped BLAST, and PSI-Blast programs, the default parameters of the respective programs (e.g., XBLAST and NBLAST) can be used. Another preferred non-limiting example of a mathematical algorithm utilized for the comparison of sequences is the algorithm of Myers and Miller, CABIOS (1989). Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. Additional algorithms for sequence analysis are known in the art and include ADVANCE and ADAM as described in Torellis and Robotti, 1994, Comput. Appl. Biosci. 10:3-5; and FASTA described in Pearson and Lipman, 1988, Proc. Natl. Acad. Sci. USA 85:2444-8. Within FASTA, ktup is a control option that sets the sensitivity and speed of the search. If ktup=2, similar regions in the two sequences being compared are found by looking at pairs of aligned residues; if ktup=1, single aligned amino acids are examined. ktup can be set to 2 or 1 for protein sequences, or from 1 to 6 for DNA sequences. The default if ktup is not specified is 2 for proteins and 6 for DNA. Alternatively, protein sequence alignment may be carried out using the CLUSTAL W algorithm, as described by Higgins et al., 1996, Methods Enzymol. 266:383-402.

As used herein, the expressions "cell", "cell line", and "cell culture" are used interchangeably and all such designations include the progeny thereof. Thus, "transformants" and "transformed cells" include the primary subject cell and cultures derived therefrom without regard for the number of transfers.

The term "mammal" for purposes of treatment refers to any animal classified as a mammal, including humans, domesticated and farm animals, and zoo, sports, or pet animals, such as dogs, horses, cats, cows, and the like. Preferably, the mammal is human.

A "disease" or "disorder", as used herein, is any condition that would benefit from treatment with a humanized anti-C3 antibody described herein. This includes chronic and acute disorders or diseases including those pathological conditions that predispose the mammal to the disorder in question.

The term "intravitreal injection" has its normal meaning in the art and refers to introduction of an anti-C3 antibody or an antigen-binding fragment thereof into the vitreous of a patient.

The term "subcutaneous administration" refers to introduction of an anti-C3 antibody or an antigen-binding fragment thereof under the skin of an animal or human patient, preferable within a pocket between the skin and underlying tissue, by relatively slow, sustained delivery from a drug receptacle. Pinching or drawing the skin up and away from underlying tissue may create the pocket.

The term "subcutaneous infusion" refers to introduction of a drug under the skin of an animal or human patient, preferably within a pocket between the skin and underlying tissue, by relatively slow, sustained delivery from a drug receptacle for a period of time including, but not limited to, 30 minutes or less, or 90 minutes or less. Optionally, the infusion may be made by subcutaneous implantation of a drug delivery pump implanted under the skin of the animal or human patient, wherein the pump delivers a predetermined amount of drug for a predetermined period of time, such as 30 minutes, 90 minutes, or a time period spanning the length of the treatment regimen.

The term "subcutaneous bolus" refers to drug administration beneath the skin of an animal or human patient, where bolus drug delivery is less than approximately 15 minutes; in another aspect, less than 5 minutes, and in still another aspect, less than 60 seconds. In yet even another aspect, administration is within a pocket between the skin and underlying tissue, where the pocket may be created by pinching or drawing the skin up and away from underlying tissue.

The term "therapeutically effective amount" is used to refer to an amount of an anti-C3 antibody or an antigen-binding fragment thereof that relieves or ameliorates one or more of the symptoms of the disorder being treated. In doing so it is that amount that has a beneficial patient outcome. Efficacy can be measured in conventional ways, depending on the condition to be treated. For example, in eye or ocular diseases characterized by cells expressing C3, efficacy can be measured by determining the response rates, e.g., restoration of vision or by assessing the time of delay until disease progression.

The terms "treatment" and "therapy" and the like, as used herein, are meant to include therapeutic as well as prophylactic, or suppressive measures for a disease or disorder leading to any clinically desirable or beneficial effect, including but not limited to alleviation or relief of one or more symptoms, regression, slowing or cessation of progression of the disease or disorder. Thus, for example, the term treatment includes the administration of an anti-C3 antibody or an antigen-binding fragment thereof prior to or following the onset of a symptom of a disease or disorder thereby preventing or removing one or more signs of the disease or disorder. As another example, the term includes the administration of an anti-C3 antibody or an antigen-binding fragment thereof after clinical manifestation of the disease to combat the symptoms of the disease. Further, administration of an anti-C3 antibody or an antigen-binding fragment thereof after onset and after clinical symptoms have developed where administration affects clinical parameters of the disease or disorder, whether or not the treatment leads to amelioration of the disease, comprises "treatment" or "therapy" as used herein. Moreover, as long as the compositions of the invention either alone or in combination with another therapeutic agent alleviate or ameliorate at least one symptom of a disorder being treated as compared to that symptom in the absence of use of the anti-C3 antibody composition or an antigen-binding fragment thereof, the result should be considered an effective treatment of the underlying disorder regardless of whether all the symptoms of the disorder are alleviated or not.

The term "package insert" is used to refer to instructions customarily included in commercial packages of therapeutic products, that contain information about the indications, usage, administration, contraindications and/or warnings concerning the use of such therapeutic products.

Antibody of the Invention

In one embodiment, the invention relates to an anti-C3 antibody or an antigen binding fragment thereof. In a particular embodiment, is the invention provides a humanized anti-C3 antibody or antigen-binding fragment thereof. In a further embodiment, the invention provides a humanized monoclonal anti-C3 antibody or antigen-binding fragment thereof.

In an initial characterization, a library of antibodies targeting C3, in particular scFvs targeting C3, was generated. The inventors have humanized and optimized these scFvs, as illustrated in Example 4. They additionally proceeded to further engineering of the CDRs and the FRs with different alterations, in order to improve the affinity and optimize the rare occurring amino acid in human antibody. Through diverse and thorough optimization steps, the inventors developed highly promising therapeutic molecules, in particular humanized scFvs directed against C3 with enhanced properties as disclosed herein.

The sequences of the CDRs of the antibodies of the invention are shown in the table 1 below. Table 1 depicts the CDRs according to the Kabat nomenclature.

TABLE 1

| Name | Amino acid sequence | SEQ ID NO: |
|---|---|---|
| CDR-H1 | NYAMN | 1 |
| CDR-H2 | VISYDGSNKYYADSVKG | 2 |
| CDR-H2 | IINVGGGTNYADSVKG | 15 |
| CDR-H3 | AVGYHHARLDP | 3 |
| CDR-L1 | TLSSAHKTYTID | 4 |
| CDR-L2 | LKSDGSYTKGS | 5 |
| CDR-L2 | LKSEGSYTKGS | 18 |
| CDR-L3 | GTEGVGGYV | 6 |

In one embodiment, the present invention provides an anti-C3 antibody or an antigen-binding fragment thereof comprising a variable heavy chain (VH), and a variable light chain (VL),
wherein the VH comprises a CDR-H1 sequence of SEQ ID NO: 1, a CDR-H2 sequence selected from the group consisting of SEQ ID NO: 2 and 15, a CDR-H3 sequence of SEQ ID NO: 3; and
wherein the VL comprises a CDR-L1 sequence of SEQ ID NO: 4, a CDR-L2 sequence selected from the group consisting of SEQ ID NO: 5 and 18, and a CDR-L3 sequence of SEQ ID NO: 6.

In a particular embodiment, the present invention provides an anti-C3 antibody or an antigen-binding fragment thereof comprising a variable heavy chain (VH), and a variable light chain (VL), wherein the VH comprises: a CDR-H1 sequence of SEQ ID NO: 1 or an amino acid sequence being at least 80%, at least 90% or at least 95% identical to the amino acid sequence of SEQ ID NO: 1, a CDR-H2 sequence of SEQ ID NO: 2 or 15 or an amino acid sequence being at least 80%, at least 90% or at least 95% identical to the amino acid sequence SEQ ID NO: 2 or 15, and/or a CDR-H3 sequence of SEQ ID NO: 3 or an amino acid sequence being at least 80% or at least 90% identical to the amino acid sequence of SEQ ID NO: 3; and/or wherein the VL comprises: a CDR-L1 sequence of SEQ ID NO: 4 or an amino acid sequence being at least 80%, at least 90% or at least 95% identical to the amino acid sequence of SEQ ID NO: 4, a CDR-L2 sequence of SEQ ID NO: 5 or 18 or an amino acid sequence being least 80%, at least 90% or at least 95% identical to the amino acid sequence of SEQ ID NO: 5 or 18, and/or a CDR-L3 sequence of SEQ ID NO: 6 or an amino acid sequence being at least 80% or at least 85% identical to the amino acid sequence of SEQ ID NO: 6.

In a particular embodiment, the present invention provides an anti-C3 antibody or an antigen-binding fragment thereof
wherein the VH comprises a CDR-H1 sequence of SEQ ID NO: 1, a CDR-H2 sequence of SEQ ID NO: 2, and a CDR-H3 sequence of SEQ ID NO: 3; and the VL comprises a CDR-L1 sequence of SEQ ID NO: 4, a CDR-L2 sequence of SEQ ID NO: 5, and a CDR-L3 sequence of SEQ ID NO: 6, or
wherein the VH comprises a CDR-H1 sequence of SEQ ID NO: 1, a CDR-H2 sequence of SEQ ID NO: 15, and a CDR-H3 sequence of SEQ ID NO: 3; and the VL comprises a CDR-L1 sequence of SEQ ID NO: 4, a CDR-L2 sequence of SEQ ID NO: 5, and a CDR-L3 sequence of SEQ ID NO: 6,
wherein the VH comprises a CDR-H1 sequence of SEQ ID NO: 1, a CDR-H2 sequence of SEQ ID NO: 15, and a CDR-H3 sequence of SEQ ID NO: 3; and the VL comprises a CDR-L1 sequence of SEQ ID NO: 4, a CDR-L2 sequence of SEQ ID NO: 18, and a CDR-L3 sequence of SEQ ID NO: 6, or
wherein the VH comprises a CDR-H1 sequence of SEQ ID NO: 1, a CDR-H2 sequence of SEQ ID NO: 2, and a CDR-H3 sequence of SEQ ID NO: 3 and the VL comprises a CDR-L1 sequence of SEQ ID NO: 4, a CDR-L2 sequence of SEQ ID NO: 18, and a CDR-L3 sequence of SEQ ID NO: 6.

In another embodiment, the present invention provides an anti-C3 antibody or an antigen-binding fragment thereof comprising:
a heavy chain variable region comprising an amino acid sequence at least 80%, at least 90%, at least 95%, at least 98%, or at least 99% identical to the amino acid sequence of SEQ ID NO: 20, 22 or 24; and/or
a light chain variable region comprising an amino acid sequence at least 80%, at least 90%, at least 95%, at least 98%, or at least 99% identical to the amino acid sequence of SEQ ID NO: 21, 23 or 25.

In yet another embodiment, the present invention provides an anti-C3 antibody or an antigen-binding fragment thereof comprising:

a heavy chain variable region comprising an amino acid sequence at least 80%, at least 90%, at least 95%, at least 98%, or at least 99% identical to the amino acid sequence of SEQ ID NO: 20, 22 or 24; and a light chain variable region comprising an amino acid sequence at least 80%, at least 90%, at least 95%, at least 98%, or at least 99% identical to the amino acid sequence of SEQ ID NO: 21, 23 or 25;

wherein:
the VH comprises a CDR-H1 sequence of SEQ ID NO: 1, a CDR-H2 sequence selected from the group consisting of SEQ ID NO: 2 and 15, a CDR-H3 sequence of SEQ ID NO: 3; and
the VL comprises a CDR-L1 sequence of SEQ ID NO: 4, a CDR-L2 sequence selected from the group consisting of SEQ ID NO: 5 and 18, and a CDR-L3 sequence of SEQ ID NO: 6.

In another embodiment, the present invention provides an anti-C3 antibody or an antigen-binding fragment thereof comprising:

a heavy chain variable region comprising an amino acid sequence at least 80%, at least 90%, at least 95%, at least 98%, or at least 99% identical to the amino acid sequence of SEQ ID NO: 20; and a light chain variable region comprising an amino acid sequence at least 80%, at least 90%, at least 95%, at least 98%, or at least 99% identical to the amino acid sequence of SEQ ID NO: 21;

wherein:
the VH comprises a CDR-H1 sequence of SEQ ID NO: 1, a CDR-H2 sequence of SEQ ID NO: 2, and a CDR-H3 sequence of SEQ ID NO: 3; and the VL comprises a CDR-L1 sequence of SEQ ID NO: 4, a CDR-L2 sequence of SEQ ID NO: 5, and a CDR-L3 sequence of SEQ ID NO: 6.

In another embodiment, the present invention provides an anti-C3 antibody or an antigen-binding fragment thereof comprising:

a heavy chain variable region comprising an amino acid sequence at least 80%, at least 90%, at least 95%, at least 98%, or at least 99% identical to the amino acid sequence of SEQ ID NO: 22; and a light chain variable region comprising an amino acid sequence at least 80%, at least 90%, at least 95%, at least 98%, or at least 99% identical to the amino acid sequence of SEQ ID NO: 23;

wherein:
the VH comprises a CDR-H1 sequence of SEQ ID NO: 1, a CDR-H2 sequence of SEQ ID NO: 15, and a CDR-H3 sequence of SEQ ID NO: 3; and the VL comprises a CDR-L1 sequence of SEQ ID NO: 4, a CDR-L2 sequence of SEQ ID NO: 5, and a CDR-L3 sequence of SEQ ID NO: 6.

In another embodiment, the present invention provides an anti-C3 antibody or an antigen-binding fragment thereof comprising:

a heavy chain variable region comprising an amino acid sequence at least 80%, at least 90%, at least 95%, at least 98%, or at least 99% identical to the amino acid sequence of SEQ ID NO: 24; and a light chain variable region comprising an amino acid sequence at least 80%, at least 90%, at least 95%, at least 98%, or at least 99% identical to the amino acid sequence of SEQ ID NO: 25;

wherein:
the VH comprises a CDR-H1 sequence of SEQ ID NO: 1, a CDR-H2 sequence of SEQ ID NO: 15, and a CDR-H3 sequence of SEQ ID NO: 3; and the VL comprises a CDR-L1 sequence of SEQ ID NO: 4, a CDR-L2 sequence of SEQ ID NO: 18, and a CDR-L3 sequence of SEQ ID NO: 6.

In one embodiment, the invention provides an anti-C3 antibody or an antigen-binding fragment thereof comprising: a heavy chain variable region comprising the amino acid sequences of SEQ ID NO: 20, 22 or 24; and a light chain variable region comprising the amino acid sequence of SEQ ID NO: 21, 23 or 25.

In another embodiment, the invention provides an anti-C3 antibody or an antigen-binding fragment thereof comprising:
a. a variable heavy chain and a variable light chain comprising the amino acid sequences of SEQ ID NO: 20 and SEQ ID NO: 21, respectively;
b. a variable heavy chain and a variable light chain comprising the amino acid sequences of SEQ ID NO: 22 and SEQ ID NO: 23, respectively; or
c. a variable heavy chain and a variable light chain comprising the amino acid sequences of SEQ ID NO: 24 and SEQ ID NO: 25, respectively.

In yet another embodiment, the present invention provides an anti-C3 antibody or an antigen-binding fragment thereof comprising:
a. a variable heavy chain comprising, preferably consisting of, the amino acid sequence of SEQ ID NO: 20 and a variable light chain comprising, preferably consisting of the amino acid sequence of SEQ ID NO: 21, said antibody being referred to as "clone I",
b. a variable heavy chain comprising, preferably consisting of, the amino acid sequence of SEQ ID NO: 22 and a variable light chain comprising, preferably consisting of the amino acid sequence of SEQ ID NO: 23, said antibody being referred to as "clone II";
c. a variable heavy chain comprising, preferably consisting of, the amino acid sequence of SEQ ID NO: 24 and a variable light chain comprising, preferably consisting of the amino acid sequence of SEQ ID NO: 25, said antibody being referred to as "clone III".

The following table depicts the CDRs of antibodies according to the invention, according different well-known nomenclature, such as according to Kabat; according to the CCG (Chemical Computing Group as illustrated in Almagro et al., Proteins 2011; 79:3050-3066 and Maier et al, Proteins 2014; 82:1599-1610); according to Chothia; and/or according to Aho.

The table 2 further summarizes the amino acid sequences of the CDRs of the antibodies according to the invention.

TABLE 2

| Clone | Name | Amino acid sequence | Nomenclature | SEQ ID NO: |
|---|---|---|---|---|
| Clone I | CDR-H1 | NYAMN | Kabat | 1 |
| | CDR-H2 | VISYDGSNKYYADSVKG | Kabat | 2 |
| | CDR-H3 | AVGYHHARLDP | Kabat | 3 |
| | CDR-L1 | TLSSAHKTYTID | Kabat | 4 |
| | CDR-L2 | LKSDGSYTKGS | Kabat | 5 |
| | CDR-L3 | GTEGVGGYV | Kabat | 6 |
| | CDR-H1 | GFTFSNYAMN | CCG | 7 |
| | CDR-H2 | VISYDGSNKYYADSVKG | CCG | 2 |
| | CDR-H3 | AVGYHHARLDP | CCG | 3 |
| | CDR-L1 | TLSSAHKTYTID | CCG | 4 |
| | CDR-L2 | LKSDGSYTKGS | CCG | 5 |
| | CDR-L3 | GTEGVGGYV | CCG | 6 |
| | CDR-H1 | GFTFSNY | Chothia | 8 |
| | CDR-H2 | SYDGSN | Chothia | 9 |

TABLE 2-continued

| Clone | Name | Amino acid sequence | Nomen-clature | SEQ ID NO: |
|---|---|---|---|---|
| | CDR-H3 | AVGYHHARLDP | Chothia | 3 |
| | CDR-L1 | TLSSAHKTYTID | Chothia | 4 |
| | CDR-L2 | LKSDGSYTKGS | Chothia | 5 |
| | CDR-L3 | GTEGVGGYV | Chothia | 6 |
| | CDR-H1 | GFTFSNYA | Aho | 10 |
| | CDR-H2 | ISYDGSNK | Aho | 11 |
| | CDR-H3 | ARAVGYHHARLDP | Aho | 12 |
| | CDR-L1 | SAHKTYT | Aho | 13 |
| | CDR-L2 | LKSDGSY | Aho | 14 |
| | CDR-L3 | GTEGVGGYV | Aho | 6 |
| Clone II | CDR-H1 | NYAMN | Kabat | 1 |
| | CDR-H2 | IINVGGGTNYADSVKG | Kabat | 15 |
| | CDR-H3 | AVGYHHARLDP | Kabat | 3 |
| | CDR-L1 | TLSSAHKTYTID | Kabat | 4 |
| | CDR-L2 | LKSDGSYTKGS | Kabat | 5 |
| | CDR-L3 | GTEGVGGYV | Kabat | 6 |
| | CDR-H1 | GFTFSNYAMN | CCG | 7 |
| | CDR-H2 | IINVGGGTNYADSVKG | CCG | 15 |
| | CDR-H3 | AVGYHHARLDP | CCG | 3 |
| | CDR-L1 | TLSSAHKTYTID | CCG | 4 |
| | CDR-L2 | LKSDGSYTKGS | CCG | 5 |
| | CDR-L3 | GTEGVGGYV | CCG | 6 |
| | CDR-H1 | GFTFSNY | Chothia | 8 |
| | CDR-H2 | NVGGG | Chothia | 16 |
| | CDR-H3 | AVGYHHARLDP | Chothia | 3 |
| | CDR-L1 | TLSSAHKTYTID | Chothia | 4 |
| | CDR-L2 | LKSDGSYTKGS | Chothia | 5 |
| | CDR-L3 | GTEGVGGYV | Chothia | 6 |
| | CDR-H1 | GFTFSNYA | Aho | 10 |
| | CDR-H2 | INVGGGT | Aho | 17 |
| | CDR-H3 | ARAVGYHHARLDP | Aho | 12 |
| | CDR-L1 | SAHKTYT | Aho | 13 |
| | CDR-L2 | LKSDGSY | Aho | 14 |
| | CDR-L3 | GTEGVGGYV | Aho | 6 |
| Clone III | CDR-H1 | NYAMN | Kabat | 1 |
| | CDR-H2 | IINVGGGTNYADSVKG | Kabat | 15 |
| | CDR-H3 | AVGYHHARLDP | Kabat | 3 |
| | CDR-L1 | TLSSAHKTYTID | Kabat | 4 |
| | CDR-L2 | LKSEGSYTKGS | Kabat | 18 |
| | CDR-L3 | GTEGVGGYV | Kabat | 6 |
| | CDR-H1 | GFTFSNYAMN | CCG | 7 |
| | CDR-H2 | IINVGGGTNYADSVKG | CCG | 15 |
| | CDR-H3 | AVGYHHARLDP | CCG | 3 |
| | CDR-L1 | TLSSAHKTYTID | CCG | 4 |
| | CDR-L2 | LKSEGSYTKGS | CCG | 18 |
| | CDR-L3 | GTEGVGGYV | CCG | 6 |
| | CDR-H1 | GFTFSNY | Chothia | 8 |
| | CDR-H2 | NVGGG | Chothia | 16 |
| | CDR-H3 | AVGYHHARLDP | Chothia | 3 |
| | CDR-L1 | TLSSAHKTYTID | Chothia | 4 |
| | CDR-L2 | LKSEGSYTKGS | Chothia | 18 |
| | CDR-L3 | GTEGVGGYV | Chothia | 6 |
| | CDR-H1 | GFTFSNYA | Aho | 10 |
| | CDR-H2 | INVGGGT | Aho | 17 |
| | CDR-H3 | ARAVGYHHARLDP | Aho | 12 |
| | CDR-L1 | SAHKTYT | Aho | 13 |
| | CDR-L2 | LKSEGSY | Aho | 19 |
| | CDR-L3 | GTEGVGGYV | Aho | 6 |

Therefore, in a specific aspect, the invention relates to an anti-C3 antibody or an antigen-binding fragment thereof comprising a variable heavy chain (VH), and a variable light chain (VL), wherein the VH comprises a CDR-H1 selected from the group consisting of SEQ ID NO: 1, 7, 8, and 10, a CDR-H2 sequence selected from the group consisting of SEQ ID NO: 2, 9, 11, 15, 16, and 17, a CDR-H3 sequence selected from the group consisting of SEQ ID NO: 3 and 12; and wherein the VL comprises a CDR-L1 sequence selected from the group consisting of SEQ ID NO: 4 and 13, a CDR-L2 sequence selected from the group consisting of SEQ ID NO: 5, 14, 18 and 19, and a CDR-L3 sequence of SEQ ID NO: 6.

In a particular aspect, the invention relates to an anti-C3 antibody or an antigen-binding fragment thereof comprising a variable heavy chain (VH), and a variable light chain (VL), wherein the VH comprises a CDR-H1 sequence of SEQ ID NO: 7, a CDR-H2 sequence of SEQ ID NO: 2, and a CDR-H3 sequence of SEQ ID NO: 3; and the VL comprises a CDR-L1 sequence of SEQ ID NO: 4, a CDR-L2 sequence of SEQ ID NO: 5, and a CDR-L3 sequence of SEQ ID NO: 6, or wherein the VH comprises a CDR-H1 sequence of SEQ ID NO: 8 a CDR-H2 sequence of SEQ ID NO: 9, and a CDR-H3 sequence of SEQ ID NO: 3; and the VL comprises a CDR-L1 sequence of SEQ ID NO: 4, a CDR-L2 sequence of SEQ ID NO: 5, and a CDR-L3 sequence of SEQ ID NO: 6, or wherein the VH comprises a CDR-H1 sequence of SEQ ID NO: 10, a CDR-H2 sequence of SEQ ID NO: 11, and a CDR-H3 sequence of SEQ ID NO: 12; and the VL comprises a CDR-L1 sequence of SEQ ID NO: 13, a CDR-L2 sequence of SEQ ID NO: 14, and a CDR-L3 sequence of SEQ ID NO: 6, or wherein the VH comprises a CDR-H1 sequence of SEQ ID NO: 7, a CDR-H2 sequence of SEQ ID NO: 15, and a CDR-H3 sequence of SEQ ID NO: 3; and the VL comprises a CDR-L1 sequence of SEQ ID NO: 4, a CDR-L2 sequence of SEQ ID NO: 5, and a CDR-L3 sequence of SEQ ID NO: 6, or wherein the VH comprises a CDR-H1 sequence of SEQ ID NO: 8, a CDR-H2 sequence of SEQ ID NO: 16, and a CDR-H3 sequence of SEQ ID NO: 3; and the VL comprises a CDR-L1 sequence of SEQ ID NO: 4, a CDR-L2 sequence of SEQ ID NO: 5, and a CDR-L3 sequence of SEQ ID NO: 6, or wherein the VH comprises a CDR-H1 sequence of SEQ ID NO: 10, a CDR-H2 sequence of SEQ ID NO: 17, and a CDR-H3 sequence of SEQ ID NO: 12; and the VL comprises a CDR-L1 sequence of SEQ ID NO: 13, a CDR-L2 sequence of SEQ ID NO: 14, and a CDR-L3 sequence of SEQ ID NO: 6, or wherein the VH comprises a CDR-H1 sequence of SEQ ID NO: 7, a CDR-H2 sequence of SEQ ID NO: 15, and a CDR-H3 sequence of SEQ ID NO: 3; and the VL comprises a CDR-L1 sequence of SEQ ID NO: 4, a CDR-L2 sequence of SEQ ID NO: 18, and a CDR-L3 sequence of SEQ ID NO: 6, or wherein the VH comprises a CDR-H1 sequence of SEQ ID NO: 8, a CDR-H2 sequence of SEQ ID NO: 16, and a CDR-H3 sequence of SEQ ID NO: 3; and the VL comprises a CDR-L1 sequence of SEQ ID NO: 4, a CDR-L2 sequence of SEQ ID NO: 18, and a CDR-L3 sequence of SEQ ID NO: 6, or wherein the VH comprises a CDR-H1 sequence of SEQ ID NO: 10, a CDR-H2 sequence of SEQ ID NO: 17, and a CDR-H3 sequence of SEQ ID NO: 12; and the VL comprises a CDR-L1 sequence of SEQ ID NO: 13, a CDR-L2 sequence of SEQ ID NO: 19, and a CDR-L3 sequence of SEQ ID NO: 6.

The sequences of exemplary variable heavy chains and variable light chains according to the invention are depicted in the table 3.

TABLE 3

| Name | Sequence | SEQ ID No |
|---|---|---|
| VH-Clone I | QVQLVESGGGSVQPGRSLRLSCAASGFTFSNYAMNWVRQAPGKGLEWVAVISYDGSNKYYADSVKGRFTISRDNSKNTLYLQMNSLRAEDTASYYCARAVGYHHARLDPWGCGTSVTVSS | 20 |
| VL-Clone I | QLVLTQSPSASASLGASVKLTCTLSSAHKTYTIDWYQQQPEKCPRYLMQLKSDGSYTKGSGIPDRFSGSSSGAERYLTISSLQSEDEADYYCGTEGVGGYVFGGGTKLTVLG | 21 |
| VH-Clone II | QVQLVESGGGSVQPGRSLRLSCAASGFTFSNYAMNWVRQAPGKGLEWVAIINVGGGTNYADSVKGRFTISRDNSKNTLYLQMNSLRAEDTASYYCARAVGYHHARLDPWGCGTSVTVSS | 22 |
| VL-Clone II | QLVLTQSPSASASLGASVKLTCTLSSAHKTYTIDWYQQQPEKCPRYLMQLKSDGSYTKGSGIPDRFSGSSSGAERYLTISSLQSEDEADYYCGTEGVGGYVFGGGTKLTVLG | 23 |
| VH-Clone III | QVQLVESGGGSVQPGRSLRLSCAASGFTFSNYAMNWVRQAPGKGLEWVAIINVGGGTNYADSVKGRFTISRDNSKNTLYLQMNSLRAEDTASYYCARAVGYHHARLDPWGCGTSVTVSS | 24 |
| VL-Clone III | QLVLTQSPSASASLGASVKLTCTLSSAHKTYTIDWYQQQPEKCPRYLMQLKSEGSYTKGSGIPDRFSGSSSGAERYLTISSLQSEDEADYYCGTEGVGGYVFGGGTKLTVLG | 25 |

The sequences of exemplary scFv of the invention are depicted in the table 4.

TABLE 4

| Name | sequence | SEQ ID No |
|---|---|---|
| Clone I | QLVLTQSPSASASLGASVKLTCTLSSAHKTYTIDWYQQQPEKCPRYLMQLKSDGSYTKGSGIPDRFSGSSSGAERYLTISSLQSEDEADYYCGTEGVGGYVFGGGTKLTVLGGGGSGGGGSGGGGSQVQLVESGGGSVQPGRSLRLSCAASGFTFSNYAMNWVRQAPGKGLEWVAVISYDGSNKYYADSVKGRFTISRDNSKNTLYLQMNSLRAEDTASYYCARAVGYHHARLDPWGCGTSVTVSS | 26 |
| Clone I | MQLVLTQSPSASASLGASVKLTCTLSSAHKTYTIDWYQQQPEKCPRYLMQLKSDGSYTKGSGIPDRFSGSSSGAERYLTISSLQSEDEADYYCGTEGVGGYVFGGGTKLTVLGGGGGSGGGGSGGGGSQVQLVESGGGSVQPGRSLRLSCAASGFTFSNYAMNWVRQAPGKGLEWVAVISYDGSNKYYADSVKGRFTISRDNSKNTLYLQMNSLRAEDTASYYCARAVGYHHARLDPWGCGTSVTVSS | 27 |
| Clone II | QLVLTQSPSASASLGASVKLTCTLSSAHKTYTIDWYQQQPEKCPRYLMQLKSDGSYTKGSGIPDRFSGSSSGAERYLTISSLQSEDEADYYCGTEGVGGYVFGGGTKLTVLGGGGSGGGGSGGGGSQVQLVESGGGSVQPGRSLRLSCAASGFTFSNYAMNWVRQAPGKGLEWVAIINVGGGTNYADSVKGRFTISRDNSKNTLYLQMNSLRAEDTASYYCARAVGYHHARLDPWGCGTSVTVSS | 28 |
| Clone II | MQLVLTQSPSASASLGASVKLTCTLSSAHKTYTIDWYQQQPEKCPRYLMQLKSDGSYTKGSGIPDRFSGSSSGAERYLTISSLQSEDEADYYCGTEGVGGYVFGGGTKLTVLGGGGSGGGGSGGGGSQVQLVESGGGSVQPGRSLRLSCAASGFTFSNYAMNWVRQAPGKGLEWVAIINVGGGTNYADSVKGRFTISRDNSKNTLYLQMNSLRAEDTASYYCARAVGYHHARLDPWGCGTSVTVSS | 29 |
| Clone III | QLVLTQSPSASASLGASVKLTCTLSSAHKTYTIDWYQQQPEKCPRYLMQLKSEGSYTKGSGIPDRFSGSSSGAERYLTISSLQSEDEADYYCGTEGVGGYVFGGGTKLTVLGGGGSGGGGSGGGGSQVQLVESGGGSVQPGRSLRLSCAASGFTFSNYAMNWVRQAPGKGLEWVAIINVGGGTNYADSVKGRFTISRDNSKNTLYLQMNSLRAEDTASYYCARAVGYHHARLDPWGCGTSVTVSS | 30 |
| Clone III | MQLVLTQSPSASASLGASVKLTCTLSSAHKTYTIDWYQQQPEKCPRYLMQLKSEGSYTKGSGIPDRFSGSSSGAERYLTISSLQSEDEADYYCGTEGVGGYVFGGGTKLTVLGGGGGSGGGGSGGGGSQVQLVESGGGSVQPGRSLRLSCAASGFTFSNYAMNWVRQAPGKGLEWVAIINVGGGTNYADSVKGRFTISRDNSKNTLYLQMNSLRAEDTASYYCARAVGYHHARLDPWGCGTSVTVSS | 31 |

In one embodiment, the anti-C3 antibody or the antigen-binding fragment thereof of the invention is selected from the group consisting of a single chain variable fragment (scFv), a Fab fragment, a Fab' fragment, a Fv fragment, a diabody, a small antibody mimetic. In an alternative embodiment the anti-C3 antibody or the antigen-binding fragment thereof is selected from the groups consisting of a single domain antibody, such as a sdAb, a sdFv, a nanobody, a V-Nar and a VHH. In this particular embodiment, said anti-C3 antibody or the antigen-binding fragment thereof comprises a variable heavy chain. In a further embodiment, said variable heavy chain comprises a CDR-H1 sequence of SEQ ID NO: 1, a CDR-H2 sequence selected from the group consisting of SEQ ID NO: 2 and 15, a CDR-H3 sequence of SEQ ID NO: 3. In a specific embodiment, said variable heavy chain comprises the amino acid sequences of SEQ ID NO: 20, 22 or 24.

In one embodiment, the antibody of the invention is a single chain fragment comprising a linker, preferably comprising the linker set forth in SEQ ID NO: 46 (GGGGSGGGGSGGGGSGGGGS).

In one embodiment, the antibody of the invention is a single chain fragment comprising one sequence selected from the group consisting of SEQ ID NO: 26, 27, 28, 29, 30 and 31.

In one embodiment, the anti-C3 antibody or the antigen-binding fragment thereof according to the invention is capable of inhibiting the pathways of complement activation, including the Classical pathway (CP), the Lectin pathway (LP), and the Alternative pathway (AP).

In one embodiment, the anti-C3 antibody or the antigen-binding fragment thereof according to the invention capable of binding complement C3 and C3b.

In one embodiment, the anti-C3 antibody or the antigen-binding fragment thereof according to the invention is capable of preventing the formation of C3 convertase.

In one embodiment, the anti-C3 antibody or the antigen-binding fragment thereof according to the invention is capable of penetrating Bruch's membrane.

In one embodiment, the anti-C3 antibody or the antigen-binding fragment thereof according to the invention has approximately equivalent binding affinity for C3 and C3b.

In one embodiment, the anti-C3 antibody or the antigen-binding fragment thereof according to the invention has a binding affinity for C3a, iC3b, C4, C4b, C5, and/or C5b of about $10^{-4}$ M or below (i.e. weaker).

In one embodiment, the anti-C3 antibody or the antigen-binding fragment thereof according to the invention has weaker binding affinity for C3a, iC3b, C4, C4b, C5, and/or C5b compared to the binding affinity for C3 and C3b.

In one embodiment, the anti-C3 antibody or the antigen-binding fragment thereof according to the invention has no binding affinity for C3a, iC3b, C4, C4b, C5, and/or C5b.

In one embodiment, the anti-C3 antibody or the antigen-binding fragment thereof according to the invention is capable of inhibiting the C3 convertase amplification loop.

In one embodiment, the anti-C3 antibody or the antigen-binding fragment thereof according to the invention is capable of inhibiting choroidal C3 activity.

The anti-C3 antibody of the invention or the antigen-binding fragment thereof according to the invention binds with high affinity to human C3. In an embodiment relating to this aspect, the anti-C3 antibody of the present invention binds to human C3 at a $K_D<50$ nM, preferably at a $K_D<15$ nM, preferably at a $K_D<10$ nM, preferably at a $K_D<7$ nM, preferably at a $K_D<1$ nM, preferably at a $K_D<0.5$ nM, preferably at a $K_D<0.2$ nM, preferably at a $K_D<0.15$ nM, preferably at a $K_D<0.10$ nM, preferably at a $K_D<0.05$ nM, preferably at a $K_D<0.04$ nM, more preferably at a $K_D<0.03$ nM, e.g., as determined by SPR. In one embodiment, the anti-C3 antibody of the present invention binds to human C3 at a $K_D$ comprised between 0.16 to 0.023 nM, as exemplified in Example 8.

In a one embodiment, the anti-C3 antibody or the antigen-binding fragment thereof according to the invention binds to human C3b at a $K_D<50$ nM, preferably at a $K_D<15$ nM, preferably at a $K_D<10$ nM, preferably at a $K_D<7$ nM, preferably at a $K_D<1$ nM, preferably at a $K_D<0.5$ nM, preferably at a $K_D<0.2$ nM, preferably at a $K_D<0.15$ nM, preferably at a $K_D<0.10$ nM, more preferably at a $K_D<0.05$ nM, e.g., as determined by SPR. In a further embodiment, the anti-C3 antibody of the present invention binds to human C3 at a $K_D$ comprised between 0.15 nM to 0.05 nM, as exemplified in Example 8.

In one embodiment, the anti-C3 antibody or the antigen-binding fragment thereof according to the invention have a binding affinity for C3 and C3b of about $10^{-8}$ M to about $10^{-14}$ M. In certain embodiments, the antibody according to the invention have a binding affinity for C3 and C3b of about $10^{-10}$ M to about $10^{-12}$ M. In certain embodiments, the anti-C3 antibodies of the invention have a binding affinity for C3 and C3b of at least (stronger than) about $10^{-8}$ M, at least (stronger than) about $10^{-9}$ M, at least (stronger than) about $10^{-10}$ M, at least (stronger than) about 10-11 M, or at least (stronger than) about $10^{-12}$ M. In one embodiment, the antibody according to the invention has approximately equivalent binding affinity for C3 and C3b. For example, but in no way limiting, the antibody according to the invention can have a binding affinity for C3 of about $10^{-10}$ M and a binding affinity for C3b of about $10^{-10}$ M. In a particular embodiment, the antibody according to the invention has a binding affinity for C3 of about 10-11 M and a binding affinity for C3b of about $10^{-11}$ M. In another embodiment, the antibody according to the invention has a binding affinity for C3 of about $10^{-12}$ M and a binding affinity for C3b of about $10^{-12}$ M.

In one alternative embodiment, the binding affinity for C3 is within a factor of 10 of the binding affinity for C3b.

In one embodiment, the anti-C3 antibody or the antigen-binding fragment thereof according to the invention shows cross-reactivity with cynomolgus C3. The inventors have shown in Example 8 that the antibodies of the invention also bind cynomolgus C3. Cynomolgus (*Macaca fascicularis*) C3 is 95.1% identical to human C3 and cross-reactivity allows for the preclinical and toxicology testing of the anti-C3 antibodies of the invention in a relevant animal model.

In one embodiment, the anti-C3 antibody or the antigen-binding fragment thereof according to the invention has a binding affinity for C3 disease-relevant single nucleotide polymorphism (SNP), more precisely C3 SNP P314L and C3 SNP R102G. The inventors have also shown in Example 8 that the antibody of the invention binds to disease-relevant SNP of human C3, ensuring the antibodies of the invention can treat a wide range of patient suffering from eye or ocular disease.

The high binding affinity of the anti-C3 antibody or the antigen-binding fragment thereof according to the invention contributes to prolong the time for neutralization of C3 after intravitreal injection and further allows a reduced injection frequency. A higher binding affinity further allows the administration of a lower dose, limiting the potential side effects. The advantageous binding affinity and reduced injection frequency considerably ameliorate the efficacy of the treatment of patients in need thereof.

Due to its high binding affinity, its advantageous half-life and its ability to be highly concentrated, the anti-C3 antibody of the invention allows for an increased interval between dosing. It also provides valuable benefits for the patient, especially an improved drug observance and compliance.

The anti-C3 antibody or the antigen-binding fragment thereof according to the invention may have a therapeutically effective duration longer than 1 month which may be a longer duration compared to other therapeutic agents. The increased therapeutically effective duration may be due to the molar concentration of the anti-C3 antibodies or the antigen-binding fragments thereof of the invention, that can reach as high as 7 mM.

The anti-C3 antibody or the antigen-binding fragment thereof according to the invention may be more easily injected to the eye compared with other therapeutic agents. In one embodiment, the anti-C3 antibodies of the invention do not contain PEG, thereby reducing their viscosity, as illustrated in Example 13. Thus, the viscosity of the anti-C3 antibodies of the invention is expected to be lower than that of other therapeutic agents. Reduced viscosity solutions, such as solutions that are less than or equal to 20 centipoise (cP) are more easily injected into the eye because of a reduced back-pressure.

The inventors have shown the anti-C3 antibodies or the antigen-binding fragments thereof according to the invention present excellent pharmaceutical features, as illustrated by an improved stability. The inventors have indeed shown in Example 11 that the anti-C3 antibody or the antigen-binding fragment thereof according to the invention shows improved thermal stability. These results illustrate that the antibody of the invention remains in its native and active conformation at physiological temperature. It is noteworthy that a higher thermal transition midpoints ($T_m$) reflects an improved stability of a protein at lower temperatures. The inventors have thus shown that the anti-C3 antibody or the antigen-binding fragment thereof according to the invention shows improved thermal stability property contributing to an improved therapeutic efficacy while allowing a reduced injection dose and frequency to patients. In addition, a $T_m$ is indicative of a extended shelf-life and improved stability in time of the therapeutic product.

In a further aspect, the anti-C3 antibody or the antigen-binding fragment thereof according to the invention proved to have a low immunogenicity risk as described in Examples 4 and 12. These results confirm that the antibodies of the invention are highly suitable and promising for the treatment of eye or ocular diseases, as they show low immunogenicity risks and/or low risk of developing anti-drug antibodies (ADA).

The complement system is an important part of the innate immune system that participates in tissue injury in a number of inflammatory and autoimmune diseases. The complement system includes more than 30 cell-associated and circulating proteins (e.g., C1, C1q, C1r, C1 s, C2, C3, C3a, C3b, C4, Factor B, Factor D, Factor H, Factor I).

There are three main pathways that activate complement, the classical pathway (CP), the lectin pathway (LP), and the alternative pathway (AP).

The three complement pathways are initiated by different factors, each resulting in the cleavage of complement component C3.

The classical pathway is usually triggered by the interaction of antigen and specific antibody of the correct isotype or subclass; immunoglobulin M (IgM), IgG3 and IgG1 are the most efficient activators of the classical pathway This induces a conformational change in the C1 complex, allowing it to cleave C4 and C2 to generate the C4bC2b complex. C4bC2b acts as the C3 convertase of the classical pathway.

The lectin complement pathway is triggered by the binding of a C-type lectin, mannan-binding lectin (MBL; also known as mannose-binding lectin) or a related series of proteins termed ficolins (L-ficolin, H-ficolin and M-ficolin), to terminal sugars as expressed on glycoproteins or envelope polysaccharides found on the surface of microorganisms The alternative pathway is initiated by the slow hydrolysis of circulating C3, which exposes an internal thioester group, a phenomenon referred to as 'C3 tickover'. Binding of the alternative-pathway-specific proteins factor B, factor D and properdin to hydrolysed C3 or to the complement cleavage fragment C3b leads to further activation of C3. Cleaved C3 in the form of C3b can then interact with polysaccharides or proteins on the surface of microorganisms or endotoxins (bacterial lipopolysaccharides) to initiate alternative-pathway activation and generate the MAC, as occurs during classical pathway activation.

In certain embodiments, the anti-C3 antibodies or the antigen-binding fragments thereof according to the invention are selected for their ability to inhibit one or more complement pathways, the Classical pathway, the Alternative pathway, and the Lectin pathway. In certain embodiments, the anti-C3 antibodies of the invention are selected for their ability to inhibit all three complement pathways, the Classical pathway, the Alternative pathway, and the Lectin pathway. In certain embodiments, the anti-C3 antibody or the antigen-binding fragment thereof according to the invention are capable of inhibiting all three complement pathways in the eye.

Typically, functional potency of the anti-C3 antibodies or the antigen-binding fragments thereof according to the invention in inhibiting the Classical pathway, the Alternative pathway, and the Lectin pathway can be determined by complement inhibition assay- or Hemolytic assay as described in Example 7. Potency can be expressed in an IC50 (half maximal inhibitory concentration). Therefore, in one embodiment, the antibody or fragment thereof according to the invention inhibits the Classical pathway (CP) with a potency comprised between 70 and 80 nM as measured by a Complement inhibition assay inhibits the Lectin pathway (LP) with a potency comprised between 340 and 360 nM as measured by a Complement inhibition assay, and inhibits the Alternative pathway (AP) with a potency comprised between 60 and 70 nM, as measured by a Complement inhibition assay.

The ability of the anti-C3 antibodies or the antigen-binding fragments thereof according to the invention to inhibit all three complement pathways further improves their therapeutic potential in the treatment of eye or ocular disease. In one embodiment, the ability of the antibodies of the invention to inhibit all three complement pathways further improves their therapeutic potential in the treatment of an eye or ocular disease, in particular AMD or GA. Without wishing to be bound by theory, inhibiting all three complement pathways may improve the therapeutic potential of the anti-C3 antibodies of the invention by preventing the disease-promoting effects of one active pathway from compensating for the other inactivated pathways.

Therefore, in a particular embodiment, the anti-C3 antibody or the antigen-binding fragment thereof according to the invention are capable of inhibiting all three complement pathways in the choroid region of the eye. The choroid region is a layer containing blood vessels that lines the back of the eye and is located between the retina and the sclera. The choroid region is divided into four layers, Haller's layer, Sattler's layer, the Choriocapillaris, and Bruch's membrane. Bruch's membrane, also known as the vitreous lamina, is the innermost layer of the choroid and is adjacent to the retinal pigment epithelium (RPE). In certain embodiments, the anti-C3 antibodies of the invention are capable of penetrating or diffusing across Bruch's membrane and entering the other layers of the choroid, such as, but not limited to, the Choriocapillaris.

The retina has substantial physical barriers that may prevent large molecules, such as full-length immunoglobulins, to penetrate to deeper layers which may result in reduced therapeutic effects (Jackson et al. Invest Ophthalmol Vis Sci. 2003; 44(5): 2141-6). Smaller antibody derivatives may in contrast penetrate deeper into the retina. Exemplary antibody derivates having a molecular weight of about 60 kDa or lower are antibody fragments, including, but not limited to, a Fab, a Fab' fragment, a scFab, an scFv, a Fv fragment, a nanobody, a VHH, a dAb, a V-Nar, sdAb, a sdFv, and bispecific and bivalent antibodies such as a single-chain diabody (scDb), or a DART. In certain embodiments, the anti-C3 antibody or the antigen-binding fragment thereof according to the invention have a molecular weight of about 60 kDa or lower, for example, about 55 kDa, about 50 kDa, about 45 kDa, about 40 kDa, about 35 kDa, about 30 kDa, about 25 kDa, about 20 kDa, about 15 kDa, or lower.

In one embodiment, the scFv format enables dosing frequency of 3 months. This represents a significant improvement compared to the existing therapeutic approach to treat eye or ocular diseases which requires more frequent administration. The scFv of the invention therefore sensibly improves the patient compliance.

The inventors have shown in Example 10 that the anti-C3 antibody or the antigen-binding fragment thereof according to the invention (Clone I) displays a high diffusion ability through Bruch's membrane, in particular when compared to comparative compounds A2 and Comparative Compound A3 as described in Example 2. Therefore, in one embodiment, the anti-C3 antibodies or the antigen-binding fragments thereof according to the invention are capable of penetrating or diffusing across Bruch's membrane in part due to their size, which is sufficiently low to facilitate penetration. In certain embodiments, the size of the antibodies of the invention are measured by molecular weight. In certain embodiments, the anti-C3 antibodies or the antigen-binding fragments thereof according to the invention have a molecular weight that is less than about 60 kDa. In certain embodiments, the anti-C3 antibodies of the invention are about 20 kDa to about 30 kDa or about 10 kDa to about 20 kDa. In certain embodiments, the anti-C3 antibodies of the invention are about 25 kDa. In certain embodiments, the anti-C3 antibodies of the invention are about 15 kDa. In certain embodiments, the size of the anti-C3 antibodies or the antigen-binding fragments thereof according to the invention is measured by their hydrodynamic radius. In certain embodiments, the anti-C3 antibodies of the invention have a hydrodynamic radius of less than or equal to about 3.0 nm. In certain embodiments, the anti-C3 antibodies of the invention have a hydrodynamic radius of less than or equal to about 2.5 nm. In certain embodiments, the anti-C3 antibody or the antigen-binding fragment thereof according to the invention have a hydrodynamic radius of less than or equal to about 2.0 nm.

Humanization and Amino Acid Sequence Variants

Further variant anti-C3 antibodies and antibody fragments can be engineered based on the set of CDRs identified under the sequences depicted in SEQ ID NO: 1 to 6, 15 and 18. It is to be understood that in some embodiments, in said variant of the anti-C3 antibodies and antibody fragments the amino acid sequence of the CDRs remain unchanged but the surrounding regions e.g., FR regions, can be engineered. Amino acid sequence variants of the anti-C3 antibody or fragments thereof can be prepared by introducing appropriate nucleotide changes into the anti-C3 antibody DNA, or by peptide synthesis. Such variants include, for example, deletions from, and/or insertions into and/or substitutions of, residues within the amino acid sequences of the anti-C3 antibodies or fragments thereof of the examples herein. Any combination of deletions, insertions, and substitutions is made to arrive at the final construct, provided that the final construct possesses the desired characteristics. The amino acid changes also may alter post-translational processes of the humanized or variant anti-C3 antibody or antigen-binding fragment thereof, such as changing the number or position of glycosylation sites.

Another type of amino acid variant of the antibody involves altering the original glycosylation pattern of the antibody. The term "altering" in this context means deleting one or more carbohydrate moieties found in the antibody, and/or adding one or more glycosylation sites that were not previously present in the antibody.

In some aspects, the present invention includes nucleic acid molecules that encode the amino acid sequence variants of the anti-C3 antibodies or antigen-binding fragments thereof described herein. Nucleic acid molecules encoding amino acid sequence variants of the anti-C3 antibody or fragment thereof are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the anti-C3 antibody or antigen-binding fragment thereof.

In certain embodiments, the anti-C3 antibody of the invention is an antibody fragment. There are techniques that have been developed for the production of antibody fragments. Fragments can be derived via proteolytic digestion of intact antibodies (see, e.g., Morimoto et al., 1992, Journal of Biochemical and Biophysical Methods 24:107-117; and Brennan et al., 1985, Science 229:81). Alternatively, the fragments can be produced directly in recombinant host cells. For example, Fab'-SH fragments can be directly recovered from E. coli and chemically coupled to form F(ab')$_2$ fragments (see, e.g., Carter et al., 1992, Bio/Technology 10:163-167). By another approach, F(ab')$_2$ fragments can be isolated directly from recombinant host cell culture. Other techniques for the production of antibody fragments will be apparent to the skilled practitioner.

The anti-C3 antibodies and antigen-binding fragments thereof can include modifications. Variants of the antibodies provided herein may be generated by introducing deletions, substitutions, additions, and/or modifications to the framework and/or to the CDRs. The antibody variants can then be tested for the desired function using methods described herein. Any combination(s) of deletions, substitutions, additions, modifications and insertions can be made to the antigen binding protein or fragment thereof, provided that the generated variant possesses the desired characteristics for which it can be screened using appropriate methods.

As used herein, a "conservative substitution" refers to a modification that maintains the functional properties of the parental antibody. For example, conservative amino acid substitutions include those in which the amino acid residue is replaced with an amino acid residue having similar properties. For example, substituting alanine (A) by valine (V); substituting arginine (R) by lysine (K); substituting asparagine (N) by glutamine (Q); substituting aspartic acid (D) by glutamic acid (E); substituting cysteine (C) by serine (S); substituting glutamic acid (E) by aspartic acid (D); substituting glycine (G) by alanine (A); substituting histidine (H) by arginine (R) or lysine (K); substituting isoleucine (I) by leucine (L); substituting methionine (M) by leucine (L); substituting phenylalanine (F) by tyrosine (Y); substituting serine (S) by threonine (T); substituting tryptophan (W) by tyrosine (Y); substituting phenylalanine (F) by tryptophan (W); and/or substituting valine (V) by leucine (L) and vice versa.

In certain embodiments, it may be desirable to use an anti-C3 antibody fragment, rather than an intact antibody. It may be desirable to modify the antibody fragment in order to increase its serum half-life. This can be achieved, for example, by incorporation of a salvage receptor binding epitope into the antibody fragment. In one method, the appropriate region of the antibody fragment can be altered (e.g., mutated), or the epitope can be incorporated into a peptide tag that is then fused to the antibody fragment at either end or in the middle, for example, by DNA or peptide synthesis. See, e.g., WO 96/32478.

In other embodiments, the present invention includes covalent modifications of the anti-C3 antibodies or antigen-binding fragments. Covalent modifications include modification of cysteinyl residues, histidyl residues, lysinyl and amino-terminal residues, arginyl residues, tyrosyl residues, carboxyl side groups (aspartyl or glutamyl), glutaminyl and asparaginyl residues, or seryl, or threonyl residues. Another type of covalent modification involves chemically or enzymatically coupling glycosides to the antibody. Such modifications may be made by chemical synthesis or by enzymatic or chemical cleavage of the antibody or fragment thereof, if applicable. Other types of covalent modifications of the antibody can be introduced into the molecule by reacting targeted amino acid residues of the antibody or fragment thereof with an organic derivatizing agent that is capable of reacting with selected side chains or the amino- or carboxy-terminal residues.

Removal of any carbohydrate moieties present on the antibody or fragment thereof can be accomplished chemically or enzymatically. Chemical deglycosylation is described by Hakimuddin et al., 1987, Arch. Biochem. Biophys. 259:52 and by Edge et al., 1981, Anal. Biochem., 118:131. Enzymatic cleavage of carbohydrate moieties on antibodies can be achieved by the use of a variety of endo- and exo-glycosidases as described by Thotakura et al., 1987, Meth. Enzymol 138:350.

Another type of useful covalent modification comprises linking the antibody to one of a variety of nonproteinaceous polymers, e.g., polyethylene glycol, polypropylene glycol, or polyoxyalkylenes, in the manner set forth in one or more of U.S. Pat. Nos. 4,640,835, 4,496,689, 4,301,144, 4,670, 417, 4,791,192 and 4,179,337.

The variant antibody of antigen-binding fragment thereof described herein, such as the variants comprising a sequence having a certain level of % of identity to the sequences disclosed herein, preferably retain a functional capability of the antibodies or antigen-binding fragments thereof described above, for example, specific C3 epitope binding, being capable of inhibiting the pathways of complement activation, including the Classical pathway (CP), the Lectin pathway (LP), and the Alternative pathway (AP), being capable of binding complement C3 and C3b, being capable of preventing the formation of C3 convertase and/or being capable of penetrating Bruch's membrane.

Epitope Binding

In one aspect, the invention provides an antibody or an antigen-binding fragment thereof that recognizes a specific "C3 epitope". As used herein, the term "C3 epitope" refer to a molecule (e.g., a peptide) or a fragment of a molecule capable of binding to an anti-C3 antibody or an antigen-binding fragment thereof. These terms further include, for example, a C3 antigenic determinant recognized by any of the antibodies or antigen-binding fragments of the present invention.

C3 antigen epitopes can be included in proteins, protein fragments, peptides or the like. The epitopes are most commonly proteins, short oligopeptides, oligopeptide mimics (i.e., organic compounds that mimic antibody binding properties of the C3 antigen), or combinations thereof.

In the context of epitope binding, the phrase "binds within amino acid regions X-Y . . . " means that the anti-C3 antibody or an antigen-binding fragment thereof according to the invention binds to at least one amino acid residue within the amino acid region specified in the sequence.

The antibody or antigen-binding fragments of present invention binds to an epitope of the human Complement C3 as set forth in SEQ ID NO: 47. In one embodiment, the antibody of the invention binds to an epitope of the Chain D of the human Complement C3c as set forth in SEQ ID NO: 48. SEQ ID No: 48 is available online under reference PDB: 2A74_D.

The antibody or antigen-binding fragments of the present invention binds to an epitope of the human Complement C3 as set forth in SEQ ID NO: 47. In another embodiment, the antibody of the invention binds to an epitope of the Chain D of the human Complement C3c as set forth in SEQ ID NO: 48. SEQ ID No: 48 is available online under reference PDB: 2A74_D.

It has been found that the anti-C3 antibody or the antigen-binding fragment thereof according to the invention binds to a unique epitope of the human Complement C3. In one embodiment, the anti-C3 antibody or antigen-binding fragment thereof of present invention binds to at least one amino acid residue within residues from amino acid 366 to amino acid 478 of the human Complement C3 as set forth in SEQ ID NO: 47.

In one embodiment, the invention provides anti-C3 antibody or an antigen-binding fragment thereof that binds to at least one amino acid residue selected from the group consisting of residues 366, 392-396, 413-421, 425, 427, 442, 453 and 478 of the human Complement C3 as set forth in SEQ ID NO: 47.

In one embodiment, the invention provides anti-C3 antibody or an antigen-binding fragment thereof that binds to all of the residues 366, 392-396, 413-421, 425, 427, 442, 453 and 478 of the human Complement C3 as set forth in SEQ ID NO: 47. In one embodiment, the invention relates to an anti-C3 antibody or an antigen-binding fragment thereof that binds to at least one amino acid residue within residues from amino acid 344 to amino acid 456 of the Chain D of the human Complement C3c as set forth in SEQ ID NO: 48.

In one embodiment, the invention relates to an anti-C3 antibody or an antigen-binding fragment thereof that binds to at least one residue selected from the group consisting of residues 344, 370-374, 391-399, 403, 405, 420, 431 and 456 of the Chain D of the human Complement C3c as set forth in SEQ ID NO: 48.

In one embodiment, the antibody or antigen-binding fragment thereof of the invention binds to all of the residues 344, 370-374, 391-399, 403, 405, 420, 431 and 456 of the Chain D of the human Complement C3c as set forth in SEQ ID NO: 48.

In one embodiment, the invention relates to an anti-C3 antibody or an antigen-binding fragment thereof that binds to at least one amino acid residue within residues from amino acid 369 to amino acid 418 of the Chain D of the human Complement C3c as set forth in SEQ ID NO: 48.

In another embodiment, the invention relates to an anti-C3 antibody or an antigen-binding fragment thereof that binds residues at least one residue selected from the group consisting of residues 369 to 379, 389, 391 to 401, 403 and 418 of the Chain D of the human Complement C3c as set forth in SEQ ID NO: 48.

In another embodiment, the antibody of the invention binds all residues 369 to 379, 389, 391 to 401, 403 and 418 of the Chain D of the human Complement C3c as set forth in SEQ ID NO: 48.

The sequences SEQ ID NO: 47 and 48 are depicted in the table 5 below.

TABLE 5

| Name | Sequence | SEQ ID NO: |
|---|---|---|
| Human C3 | MGPTSGPSLLLLLLTHLPLALGSPMYSIITPNILRLESEETMVLE AHDAQGDVPVTVTVHDFPGKKLVLSSEKTVLTPATNHMGNVTFTI PANREFKSEKGRNKFVTVQATFGTQVVEKVVLVSLQSGYLFIQTD KTIYTPGSTVLYRIFTVNHKLLPVGRTVMVNIENPEGIPVKQDSL SSQNQLGVLPLSWDIPELVNMGQWKIRAYYENSPQQVFSTEFEVK EYVLPSFEVIVEPTEKFYYIYNEKGLEVTITARFLYGKKVEGTAF VIFGIQDGEQRISLPESLKRIPIEDGSGEVVLSRKVLLDGVQNPR AEDLVGKSLYVSATVILHSGSDMVQAERSGIPIVTSPYQIHFTKT PKYFKPGMPFDLMVFVTNPDGSPAYRVPVAVQGEDTVQSLTQGDG VAKLSINTHPSQKPLSITVRTKKQELSEAEQATRTMQALPYSTVG | 47 |

TABLE 5-continued

| Name | Sequence | SEQ ID NO: |
|---|---|---|
| | NSNNYLHLSVLRTELRPGETLNVNFLLRMDRAHEAKIRYYTYLIM<br>NKGRLLKAGRQVREPGQDLVVLPLSITTDFIPSFRLVAYYTLIGA<br>SGQREVVADSVWVDVKDSCVGSLVVKSGQSEDRQPVPGQQMTLKI<br>EGDHGARVVLVAVDKGVFVLNKKNKLTQSKIWDVVEKADIGCTPG<br>SGKDYAGVFSDAGLTFTSSSGQQTAQRAELQCPQPAARRRRSVQL<br>TEKRMDKVGKYPKELRKCCEDGMRENPMRFSCQRRTRFISLGEAC<br>KKVFLDCCNYITELRRQHARASHLGLARSNLDEDIIAEENIVSRS<br>EFPESWLWNVEDLKEPPKNGISTKLMNIFLKDSITTWEILAVSMS<br>DKKGICVADPFEVTVMQDFFIDLRLPYSVVRNEQVEIRAVLYNYR<br>QNQELKVRVELLHNPAFCSLATTKRRHQQTVTIPPKSSLSVPYVI<br>VPLKTGLQEVEVKAAVYHHFISDGVRKSLKVVPEGIRMNKTVAVR<br>TLDPERLGREGVQKEDIPPADLSDQVPDTESETRILLQGTPVAQM<br>TEDAVDAERLKHLIVTPSGCGEQNMIGMTPTVIAVHYLDETEQWE<br>KFGLEKRQGALELIKKGYTQQLAFRQPSSAFAAFVKRAPSTWLTA<br>YVVKVFSLAVNLIAIDSQVLCGAVKWLILEKQKPDGVFQEDAPVI<br>HQEMIGGLRNNNEKDMALTAFVLISLQEAKDICEEQVNSLPGSIT<br>KAGDFLEANYMNLQRSYTVAIAGYALAQMGRLKGPLLNKFLTTAK<br>DKNRWEDPGKQLYNVEATSYALLALLQLKDFDFVPPVVRWLNEQR<br>YYGGGYGSTQATFMVFQALAQYQKDAPDHQELNLDVSLQLPSRSS<br>KITHRIHWESASLLRSEETKENEGFTVTAEGKGQGTLSVVTMYHA<br>KAKDOLTCNKFDLKVTIKPAPETEKRPQDAKNTMILEICTRYRGD<br>QDATMSILDISMMTGFAPDTDDLKQLANGVDRYISKYELDKAFSD<br>RNTLIIYLDKVSHSEDDCLAFKVHQYFNVELIQPGAVKVYAYYNL<br>EESCTRFYHPEKEDGKLNKLCRDELCRCAEENCFIQKSDDKVTLE<br>ERLDKACEPGVDYVYKTRLVKVQLSNDFDEYIMAIEQTIKSGSDE<br>VQVGQQRTFISPIKCREALKLEEKKHYLMWGLSSDFWGEKPNLSY<br>IIGKDTWVEHWPEEDECQDEENQKQCQDLGAFTESMVVFGCPN | |
| Complement C3c from Human Plasma component 1 (chain D) | SPMYSIITPNILRLESEETMVLEAHDAQGDVPVTVTVHDFPGKKL<br>VLSSEKTVLTPATNHMGNVTFTIPANREFKSEKGRNKFVTVQATF<br>GTQVVEKVVLVSLQSGYLFIQTDKTIYTPGSTVLYRIFTVNHKLL<br>PVGRTVMVNIENPEGIPVKQDSLSSQNQLGVLPLSWDIPELVNMG<br>QWKIRAYYENSPQQVFSTEFEVKEYVLPSFEVIVEPTEKFYYIYN<br>EKGLEVTITARFLYGKKVEGTAFVIFGIQDGEQRISLPESLKRIP<br>IEDGSGEVVLSRKVLLDGVQNLRAEDLVGKSLYVSATVILHSGSD<br>MVQAERSGIPIVTSPYQIHFTKTPKYFKPGMPFDLMVFVTNPDGS<br>PAYRVPVAVQGEDTVQSLTQGDGVAKLSINTHPSQKPLSITVRTK<br>KQELSEAEQATRTMQALPYSTVGNSNNYLHLSVLRTELRPGETLN<br>VNFLLRMDRAHEAKIRYYTYLIMNKGRLLKAGRQVREPGQDLVVL<br>PLSITTDFIPSFRLVAYYTLIGASGQREVVADSVWVDVKDSCVGS<br>LVVKSGQSEDRQPVPGQQMTLKIEGDHGARVVLVAVDKGVFVLNK<br>KNKLTQSKIWDVVEKADIGCTPGSGKDYAGVFSDAGLTFTSSSGQ<br>QTAQRAELQCPQP | 48 |

It is very likely that the specific C3 epitope binding results in the unexpected functional properties of the antibodies or antigen-binding fragments thereof of the present invention, for example, high binding affinity to both C3 and C3b, and potent inhibition on all three pathways of complement activation, including the Classical pathway (CP), the Lectin pathway (LP), and the Alternative pathway (AP).

Therapeutic Uses

In one aspect, the invention relates to an anti-C3 antibody or an antigen-binding fragment thereof for use as a medicament.

As previously mentioned, the inventors have thus now shown that neutralization of C3 in the retina will block the amplification loop of all complement pathways and thereby reduces the generation of the cell toxic membrane attack complex and the generation of the proinflammatory complement components (C3a, C3b, iC3b, C5a), improving the clinical outcome of patients suffering from geographic atrophy.

Consequently, the present invention provides an anti-C3 antibody or an antigen-binding fragment thereof for use in the treatment or prevention of a retinal or eye disease.

In one aspect, the present invention provides an anti-C3 antibody or an antigen-binding fragment thereof for use in the treatment or prevention of an eye or an ocular disease.

In one aspect, the present invention provides an anti-C3 antibody or an antigen-binding fragment thereof for use in the treatment or prevention of a disease selected from the group consisting of retinopathy, proliferative retinopathy (PR) such as retinopathy of prematurity, ischemic retinopathy, diabetic retinopathy (DR) including proliferative diabetic retinopathy (PDR) and non-proliferative diabetic retinopathy, diabetic macular edema (DME), diabetic macular ischemia (DMI), age-related macular degeneration (AMD) including dry AMD and wet AMD, geographic atrophy (GA), retinitis pigmentosa, inherited retinal dystrophy, myopic degeneration, retinal vein occlusions, retinal artery occlusions, endophthalmitis, uveitis, cystoid macular edema, choroidal neovascular membrane secondary to any retinal diseases, optic neuropathies, glaucoma, retinal detachment, toxic retinopathy, radiation retinopathy, traumatic retinopathy, drug-induced retinal vasculopathy, retinal neovascularisation, polypoidal choroidal vasculopathy, retinal vasculitis, retinal microaneurysm, retrolental fibroplasia, chorioretinitis, Fuch's dystrophy, macular telangiectasia, usher syndrome, Paroxysmal nocturnal hemoglobinuria (PNH), and Stargardt disease.

In another embodiment, the present invention provides an anti-C3 antibody or an antigen-binding fragment thereof for use in the treatment or prevention of a disease selected from the group consisting of age-related macular degeneration, geographic atrophy, neovascular glaucoma, and diabetic retinopathy. In yet a preferred embodiment, the present invention provides an anti-C3 antibody or an antigen-binding fragment thereof for use in the treatment or prevention of geographic atrophy.

In a preferred embodiment, the present invention provides an anti-C3 scFv for use in treating geographic atrophy, wherein said anti-C3 scFv comprises a variable heavy chain (VH), and a variable light chain (VL), wherein the VH comprises a CDR-H1 sequence of SEQ ID NO: 1, a CDR-H2 sequence selected from the group consisting of SEQ ID NO: 2 and 15, a CDR-H3 sequence of SEQ ID NO: 3; and wherein the VL comprises a CDR-L1 sequence of SEQ ID NO: 4, a CDR-L2 sequence selected from the group consisting of SEQ ID NO: 5 and 18, and a CDR-L3 sequence of SEQ ID NO: 6. In a particular embodiment, said anti-C3 scFv comprises a variable heavy chain and a variable light chain comprising the amino acid sequences of SEQ ID NO: 20 and SEQ ID NO: 21 respectively. In another particular embodiment, said anti-C3 scFv comprises a variable heavy chain and a variable light chain comprising the amino acid sequences of SEQ ID NO: 22 and SEQ ID NO: 23 respectively. In a further particular embodiment, said anti-C3 scFv comprises a variable heavy chain and a variable light chain comprising the amino acid sequences of SEQ ID NO: 24 and SEQ ID NO: 25 respectively.

The inventors have illustrated that the anti-C3 antibody or the antigen-binding fragment thereof according to the invention shows more advantageous properties than other "comparative compounds" targeting C3 mentioned in the prior art and described in Example 5.

The anti-C3 antibody or the antigen-binding fragment thereof according to the invention differs from therapeutic approaches based on APL2, NGM621 and ZIMURA®.

APL-2 or Pegcetacoplan is a pegylated derivative of the cyclic tridecapeptide compstatin (inhibitor of complement component C3). The active component of APL-2 is APL-1. The inventors have developed surrogate compounds (Comparative Compound A1 and Comparative Compound A2) for comparative purpose as illustrated in Example 5A.

APL-2 has a large molecular weight equivalent of 350 kDa and a hydrodynamic radius of about 7.8 nm, making it difficult to penetrate deeply into the retina. APL-2 only has an effective duration of 1 month, possibly due to a low concentration of 3.5 mM. APL-2 is also a PEGylated molecule, which increases its viscosity and may make it difficult to inject into the eye. Accordingly, there is a need for reducing GA progression more efficiently.

NGM621 is a humanized IgG1 monoclonal antibody that potently binds complement C3 (C3) and inhibits complement activation. The inventors have developed this compound for comparative purpose as illustrated in Example 5B. NGM621 has been described as being able to inhibit the classical and alternative pathways.

ZIMURA® (or avacincaptad pegol) is designed to inhibit complement factor C5 cleavage into C5a and C5b. ZIMURA® does not bind to C3.

The inventors have illustrated in Example 6B that the format of the anti-C3 antibodies or the antigen-binding fragments thereof according to the invention improves the quantity of delivered drug molecules in the eye per intravitreal injection. Indeed, it is illustrated that the scFv format can deliver a higher quantity of drug per IVT injection, compared to the other compounds. This confirms that the scFv format can achieve a greater complement inhibition, bolstering the therapeutic effect. In addition, the inventors have shown that scFv format allows better retinal penetration after IVT injection, compared to a Fab or IgG.

The inventors have compared the potency of the anti-C3 antibody or the antigen-binding fragment thereof according to the invention in comparison with inter alia a compstatin derivative such as Comparative Compound A1 and an IgG directed against C3 such as Comparative Compound A3 as illustrated in Example 7. The inventors have shown that the antibodies of the invention inhibit the classical, alternative and the lectin pathway more potently compared to Comparative Compound A1 and Comparative Compound A3. They have further assessed that the exemplary antibodies or fragments thereof of the invention are more potent in inhibiting the CP and LP when compared to Comparative Compound A1. They have also shown that the potency in inhibition the AP is improved in the hemolysis assay compared to Comparative Compound A1.

The inventors have also exemplified the binding affinity of the anti-C3 antibody or the antigen-binding fragment thereof according to the invention in comparison with existing compounds a compstatin derivative such as Comparative Compound A1 and an IgG directed against C3 such as Comparative Compound A3 in Example 8. The high binding affinity of the exemplary antibodies contributes to prolong the time for neutralization of C3 after intravitreal injection and further allows a reduced injection frequency. The improved binding affinity and reduced injection frequency considerably ameliorate the efficacy of the treatment of patients. It also provides valuable benefits for the patient, especially an improved drug observance and compliance.

In addition, the inventors have shown that the anti-C3 antibodies or the antigen-binding fragments thereof according to the invention bind with a higher affinity to human C3 and C3b compared to a compstatin derivative such as Comparative Compound A1 and an IgG directed against C3 such as Comparative Compound A3, enabling a more potent inhibition of C3. In comparison to Comparative Compound A3, the antibodies of the invention bind with higher affinity to C3b and will therefore block the generation of C3b in the C3 amplification loop as well the activity of already deposited C3b and C3b generated by alternative activation pathways.

The inventors have also shown in Example 8 that the anti-C3 antibody or the antigen-binding fragment thereof according to the invention binds disease-relevant single nucleotide polymorphism (SNP) of human C3, ensuring the antibodies of the invention can treat a wide range of patient suffering from eye or ocular disease. The inventors have further shown that said binding affinity is improved, compared to the binding affinity of Comparative Compound A1 to said SNP of human C3.

The inventors have illustrated in Example 10 that the anti-C3 antibody or the antigen-binding fragment thereof according to the invention allow improved permeation across the Bruch's membrane, whereas the Comparative Compound A2 and ZIMURA® shows no penetration and Comparative Compound A3 shows only reduced penetration. As the majority of the complement activity is in the RPE/Bruch's membrane/CC area, the excellent tissue penetration and diffusion through the Bruch's membrane is essential for the therapeutic approach of inhibiting the C3 pathway.

Finally, the anti-C3 antibodies or the antigen-binding fragments thereof according to the invention inhibit all complement effectors with high affinity and potency, as illustrated in Example 7. This leads to the inhibition of the C3 amplification loop in all pathways as well as the activity of already formed C3b and of C3b generated by C3 "tickover" activation. The result is a full inhibition of all complement activation pathways and all complement effector functions.

In conclusion, the inventors have thus developed a highly promising therapeutic strategy for treating patients suffering from GA and have shown the superiority of the anti-C3 antibodies or the antigen-binding fragments thereof according to the invention to the Comparative Compounds A2 and Comparative Compound A3. The inventors have indeed shown that the anti-C3 antibody or the antigen-binding fragment thereof according to the invention:

permits improved deliverance of the drug per intravitreal injection (Example 6B) and shows a better retinal penetration after equimolar intravitreal injection due to inter alia its format;

has an improved therapeutically effective duration due to inter alia its format, ensuring an improved dosing frequency and enhanced patient observance;

has a better penetration into target tissue (Example 10), and has the ability to penetrate the RPE and Bruch's membrane, thus improving its therapeutic potential in the treatment of eye or ocular disease;

has an improved potency and a more effective complement blockade, confirming that the anti-C3 antibody or the antigen-binding fragment thereof according to the invention inhibits all complement effector functions, with high affinity and potency (Examples 7 and 8);

has an improved binding affinity to C3, contributing to prolong the time for neutralization of C3 after intravitreal injection and further allowing a reduced injection frequency (Example 8);

has an improved binding affinity to C3b, in particular, the anti-C3 antibody or the antigen-binding fragment thereof according to the invention binds C3 and C3b with similar affinity, thereby ensuring an inhibition of the generation of C3b in the C3 amplification loop (Example 8); and has an improved binding affinity to disease-relevant SNP of human C3, ensuring the antibodies of the invention can treat a wide range of patients suffering from eye or ocular disease (Example 8);

shows improved stability (Examples 11 and 13); and has a low immunogenicity risk (Examples 4 and 12).

In addition, in one particular embodiment of the invention, the anti-C3 antibody or the antigen-binding fragment thereof is not PEGylated. In this embodiment, the anti-C3 antibody or the antigen-binding fragment thereof according to the invention shows reduction of risk to induce neovascularization as observed in clinical trials disclosed with regards to comparative compound such as ZIMURA® or APL-2.

Overall, the antibodies of the invention proved to be a highly effective treatment, with longest duration of effect, an improved drug molar best possible observance by the patients and best retinal efficacy in wet AMD, in particular in GA.

In one aspect, the present invention provides a pharmaceutical composition comprising an anti-C3 antibody or an antigen-binding fragment thereof and a pharmaceutically acceptable carrier.

The anti-C3 antibody or an antigen-binding fragment thereof is administered by any suitable means, including intravitreal, oral, parenteral, subcutaneous, intraperitoneal, intrapulmonary, and intranasal. Parenteral infusions include intramuscular, intravenous, intraarterial, intraperitoneal, or subcutaneous administration. In addition, the anti-C3 antibody is suitably administered by pulse infusion, particularly with declining doses of the antibody. In one aspect, the dosing is given by injections, most preferably intravenous or subcutaneous injections, depending in part on whether the administration is brief or chronic. In one embodiment, the anti-C3 antibody is administered through an intravitreal injection into the eye.

For the prevention or treatment of disease, the appropriate dosage of antibody will depend on a variety of factors such as the type of disease to be treated, as defined above, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments.

In some embodiments, the dose range of the antibodies of the invention applicable per injection is usually from 1 mg/eye to 20 mg/eye, or between 5 mg/eye and 20 mg/eye, or between 10 mg/eye and 15 mg/eye or about 15 mg/eye.

The term "suppression" is used herein in the same context as "amelioration" and "alleviation" to mean a lessening or diminishing of one or more characteristics of the disease.

The antibody composition will be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "therapeutically effective amount" of the antibody to be administered will be governed by such considerations, and is the minimum amount necessary to prevent, ameliorate, or treat the eye or ocular diseases addressed by the antibody of the invention.

The antibody needs not be, but is optionally, formulated with one or more agents currently used to prevent or treat the disorder in question. The effective amount of such other agents depends on the amount of anti-C3 antibody present in the formulation, the type of disorder or treatment, and other factors discussed above. These are generally used in the same dosages and with administration routes as used hereinbefore or about from 1 to 99% of the heretofore employed dosages.

In a specific aspect, the invention also provides a pharmaceutical composition comprising an anti-C3 antibody or an antigen-binding fragment thereof and a pharmaceutically acceptable carrier and at least one additional therapeutic agent.

Method of Treatment

In another aspect, the invention also encompasses any method for treating or preventing an eye or ocular diseases in a patient in need thereof, said method comprising the administration of an anti-C3 antibody or an antigen-binding fragment thereof of the invention.

In some embodiments, the invention relates to a method for treating or preventing an eye or ocular disease comprising administering to a patient in need thereof a pharmaceutically effective amount of the antibody or fragment thereof according to the invention. In one embodiment, said disease is selected from the group consisting of selected from the group consisting of retinopathy, proliferative retinopathy (PR) such as retinopathy of prematurity, ischemic retinopathy, diabetic retinopathy (DR) including proliferative diabetic retinopathy (PDR) and non-proliferative diabetic retinopathy, diabetic macular edema (DME), diabetic macular ischemia (DMI), age-related macular degeneration (AMD)

including dry AMD and wet AMD, geographic atrophy (GA), retinitis pigmentosa, inherited retinal dystrophy, myopic degeneration, retinal vein occlusions, retinal artery occlusions, endophthalmitis, uveitis, cystoid macular edema, choroidal neovascular membrane secondary to any retinal diseases, optic neuropathies, glaucoma, retinal detachment, toxic retinopathy, radiation retinopathy, traumatic retinopathy, drug-induced retinal vasculopathy, retinal neovascularisation, polypoidal choroidal vasculopathy, retinal vasculitis, retinal microaneurysm, retrolental fibroplasia, chorioretinitis, Fuch's dystrophy, macular telangiectasia, usher syndrome, Paroxysmal nocturnal hemoglobinuria (PNH), and Stargardt disease.

All the disclosed technical features described herein are applicable to said method of treatment.

Pharmaceutical Compositions and Administration Thereof

A composition comprising an anti-C3 antibody or an antigen-binding fragment thereof can be administered to a subject having or at risk of having an eye or ocular disease. The invention further provides for the use of an anti-C3 antibody or an antigen-binding fragment thereof in the manufacture of a medicament for prevention or treatment of an C3 related disease. The term "subject" as used herein means any mammalian patient to which an anti-C3 antibody or an antigen-binding fragment thereof can be administered, including, e.g., humans and non-human mammals, such as primates, rodents, and dogs. Subjects specifically intended for treatment using the methods described herein include humans. The anti-C3 antibody or an antigen-binding fragment thereof can be administered either alone or in combination with other compositions.

Various delivery systems are known and can be used to administer the anti-C3 antibody or an antigen-binding fragment thereof. Methods of introduction include but are not limited to intravitreal, eye drops, intradermal, intramuscular, intraperitoneal, intravenous, subcutaneous, intranasal, epidural, and oral routes. The anti-C3 antibody or an antigen-binding fragment thereof can be administered, for example by infusion, bolus or injection, and can be administered together with other biologically active agents. Administration can be systemic or local. In preferred embodiments, the administration is by intravitreal injection. Formulations for such injections may be prepared in, for example, prefilled syringes.

In certain embodiments, the anti-C3 antibodies or the antigen-binding fragments thereof according to the invention are administered intraocularly. Delivery of therapeutic compounds to the different structures of the eye, such as the retina, is challenging. The challenges include, but are not limited to, several restrictive ocular barriers, tear mechanisms, including blinking and washing out of delivered compounds, limited local injection volumes, limited local bioavailability, and low tolerance to impurities and contaminants (see, e.g., Patel et al. World J Pharmacol. 2013; 2(2): 47-64; Morrison et al. Ther. Deliv. 2014; 5(12): 1297-1315). The antibodies of the invention may overcome these challenges. The antibodies of the invention have preferably a molecular weight of about 60 kDa or less, preferably about 25 kDa. Examples of antigen binding proteins of about 60 kDa or less include, but are not limited to, scFv, VHH, and Fab fragments. Examples of antigen binding proteins of about 25 kDa or less include, but are not limited to scFv and VHH. The smaller size of the scFv enables delivery of more therapeutic compound per injection. This allows for high concentrations of the antibodies to the eye. The smaller size of the antibodies of the invention, in particular scFvs, may also improve their penetration into the disease-relevant tissues, i.e., the choroid region of the eye. The antibodies of the invention are capable of penetrating one or more layers of the choroid region, including Haller's layer, Sattler's layer, the Choriocapillaris, and Bruch's membrane, thereby targeting complement C3 and C3b within those layers of the choroid region.

In certain embodiments, intraocular administration is achieved with a drug delivery device, such as a suprachoroidal drug delivery device or a subretinal drug delivery device. Suprachoroidal administration procedures involve administration of a drug to the suprachoroidal space of the eye, and are normally performed using a suprachoroidal drug delivery device such as a microinjector with a microneedle (see, e.g., Hariprasad, Retinal Physician; 2016; 13: 20-23; Goldstein, 2014, Retina Today 9(5): 82-87; each of which is incorporated by reference herein in its entirety).

In certain embodiments intraocular administration is achieved via an intravitreal route. Intravitreal administration is often performed with a syringe and a 27-gauge to 30-gauge needle (see, e.g., Jiang et al. supra).

While all these forms of administration are clearly contemplated as being within the scope of the present invention, a form for administration would be a solution for injection, in particular for intravitreal injection. Usually, a suitable pharmaceutical composition for injection may comprise a buffer (e.g., acetate, phosphate or citrate buffer), a surfactant (e.g., polysorbate), optionally a stabilizer agent (e.g., human albumin), etc. However, in other methods compatible with the teachings herein, the antibodies of the invention can be delivered directly to the site of the adverse cellular population thereby increasing the exposure of the diseased tissue to the therapeutic agent.

In alternative embodiments, the pharmaceutical composition can be formulated in accordance with routine procedures as a pharmaceutical composition adapted for intravenous or subcutaneous administration to human beings. Typically, compositions for administration by injection are solutions in sterile isotonic aqueous buffer. Where necessary, the pharmaceutical can also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the pharmaceutical is to be administered by infusion, it can be dispensed with an infusion bottle containing sterile pharmaceutical grade water or saline. Where the pharmaceutical is administered by injection, an ampoule of sterile water for injection or saline can be provided so that the ingredients can be mixed prior to administration.

Further, the pharmaceutical composition can be provided as a pharmaceutical kit comprising (a) a container containing an anti-C3 antibody or an antigen-binding fragment thereof according to the invention in lyophilized form and (b) a second container containing a pharmaceutically acceptable diluent (e.g., sterile water) for injection. The pharmaceutically acceptable diluent can be used for reconstitution or dilution of the lyophilized anti-C3 antibody or an antigen-binding fragment thereof. Optionally associated with such container(s) can be a notice in the form prescribed by a governmental agency regulating the manufacture, use or sale of pharmaceuticals or biological products, which notice reflects approval by the agency of manufacture, use or sale for human administration.

The amount of the anti-C3 antibody or an antigen-binding fragment thereof according to the invention that is effective in the treatment or prevention of an eye or ocular disease can be determined by standard clinical techniques. In addition, in vitro assays may optionally be employed to help identify optimal dosage ranges. The precise dose to be employed in the formulation will also depend on the route of administration, and the stage of disorder, and should be decided according to the judgment of the practitioner and each patient's circumstances. Effective doses may be extrapolated from dose-response curves derived from in vitro or animal model test systems.

For example, toxicity and therapeutic efficacy of the anti-C3 antibody or an antigen-binding fragment thereof according to the invention can be determined in cell cultures or experimental animals by standard pharmaceutical procedures for determining the $ED_{50}$ (the dose therapeutically effective in 50% of the population). An anti-C3 antibody or an antigen-binding fragment thereof that exhibits a large therapeutic index is preferred.

The data obtained from the cell culture assays and animal studies can be used in formulating a range of dosage for use in humans. The dosage of the anti-C3 antibody or an antigen-binding fragment thereof typically lies within a range of circulating concentrations that include the $ED_{50}$ with little or no toxicity. The dosage may vary within this range depending upon the dosage form employed and the route of administration utilized. For any anti-C3 antibody or an antigen-binding fragment thereof used in the method, the therapeutically effective dose can be estimated initially from cell culture assays. A dose can be formulated in animal models to achieve a circulating plasma concentration range that includes the $IC_{50}$ (i.e., the concentration of the test compound that achieves a half-maximal inhibition of symptoms) as determined in cell culture. Such information can be used to more accurately determine useful doses in humans. Levels in plasma can be measured, for example, by high performance liquid chromatography, ELISA and the like.

For intravitreal injection of the anti-C3 antibody or the antigen-binding fragment thereof according to the invention generally longer intervals between treatments are preferred. Due to its improved potency, the anti-C3 antibody of the present invention can be administered in longer intervals.

In one embodiment the anti-C3 antibody or the antigen-binding fragment thereof according to the invention is administered every 6 weeks, preferably every 7 weeks, preferably every 8 weeks, preferably every 9 weeks, preferably every 10 weeks, preferably every 11 weeks, and more preferably every 12 weeks. In a yet preferred embodiment, the anti-C3 antibody or the antigen-binding fragment thereof according to the invention is administered once every 3 months.

Since the volume that can be administered to the eye is strictly limited, it is very important that the anti-C3 antibody or the antigen-binding fragment thereof according to the invention can be formulated to high concentrations. Furthermore, potency of the anti-C3 antibody or the antigen-binding fragment thereof according to the invention is of great importance as a potent antibody can exert its effect at even lower doses and thereby prolong activity and also intervals between treatments.

Antibodies of the present invention can be formulated to very high doses which include, but are not limited to 20 mg/ml, 30 mg/ml, 40 mg/ml, 50 mg/ml, 60 mg/ml, 70 mg/ml, 80 mg/m, 90 mg/ml, 100 mg/ml, 110 mg/ml, 120 mg/ml, 130 mg/ml, 140 mg/ml, 150 mg/ml, 160 mg/ml, 170 mg/ml, 180 mg/ml, 190 mg/ml, 200 mg/ml. Preferably, the anti-C3 antibody or the antigen-binding fragment thereof according to the invention cam be formulated in a liquid formulation with a concentration comprises between 90 mg/ml and 180 mg/m I, more preferably between 130 mg/ml and 160 mg/ml formulation of about Preferably, the anti-C3 antibody or the antigen-binding fragment thereof according to the invention can be formulated in a liquid formulation of about 150 mg/ml.

A typical dosage that can be administered to a patient is about between 2.5 mg/eye and 20 mg/eye, or between 7.5 mg/eye and 15 mg/eye. In a particular embodiment the anti-C3 antibody or the antigen-binding fragment thereof according to the invention can be administered to a patient at the concentration of 7.5 mg per eye. In another particular embodiment the anti-C3 antibody or the antigen-binding fragment thereof according to the invention can be administered to a patient at the concentration of 15 mg per eye. Typical buffer components that can be used for such a formulation comprise e.g., Sodium Acetate, PS20, and Trehalose Dihydrate.

In some embodiments, the pharmaceutical compositions comprising the anti-C3 antibody or an antigen-binding fragment thereof can further comprise a therapeutic agent, either conjugated or unconjugated to the binding agent.

With respect to therapeutic regimens for combinatorial administration, in a specific embodiment, the anti-C3 antibody or the antigen-binding fragment thereof is administered concurrently with a therapeutic agent. In another specific embodiment, the therapeutic agent is administered prior or subsequent to administration of the anti-C3 antibody or an antigen-binding fragment thereof, by at least an hour and up to several months, for example at least an hour, five hours, 12 hours, a day, a week, a month, or three months, prior or subsequent to administration of the anti-C3 antibody or an antigen-binding fragment thereof.

Polynucleotides, Vectors, Host Cells, and Recombinant Methods

In one aspect, the present invention encompasses isolated polynucleotides that comprise a sequence encoding the anti-C3 antibody or the antigen-binding fragment thereof according to the invention, vectors, and host cells comprising the polynucleotides, and recombinant techniques for production of the antibody. The isolated polynucleotides can encode any desired form of the anti-C3 antibody or the antigen-binding fragment thereof including, for example, full length monoclonal antibodies, Fab, Fab', F(ab')$_2$, and Fv fragments, diabodies, linear antibodies, single-chain antibody molecules, and multispecific antibodies formed from antibody fragments.

The polynucleotide(s) that comprise a sequence encoding the anti-C3 antibody or the antigen-binding fragment thereof according to the invention can be fused to one or more regulatory or control sequence, as known in the art, and can be contained in suitable expression vectors or host cell as known in the art. Each of the polynucleotide molecules encoding the heavy or light chain variable domains can be independently fused to a polynucleotide sequence encoding a constant domain, such as a human constant domain, enabling the production of intact antibodies. Alternatively, polynucleotides, or portions thereof, can be fused together, providing a template for production of a single chain antibody.

For recombinant production, a polynucleotide encoding the antibody or antigen-binding fragment thereof is inserted into a replicable vector for cloning (amplification of the DNA) or for expression. Many suitable vectors for expressing the recombinant antibody are available. The vector components generally include, but are not limited to, one or more of the following: a signal sequence, an origin of replication, one or more marker genes, an enhancer element, a promoter, and a transcription termination sequence.

The anti-C3 antibody or the antigen-binding fragment thereof according to the invention can also be produced as fusion polypeptides, in which said antibody or fragment thereof is fused with a heterologous polypeptide, such as a signal sequence or other polypeptide having a specific cleavage site at the amino terminus of the mature protein or polypeptide. The heterologous signal sequence selected is typically one that is recognized and processed (i.e., cleaved by a signal peptidase) by the host cell. For prokaryotic host cells that do not recognize and process the anti-C3 antibody signal sequence, the signal sequence can be substituted by a prokaryotic signal sequence. The signal sequence can be, for example, alkaline phosphatase, penicillinase, lipoprotein, heat-stable enterotoxin II leaders, and the like. For yeast secretion, the native signal sequence can be substituted, for example, with a leader sequence obtained from yeast invertase alpha-factor (including *Saccharomyces* and *Kluyveromyces* α-factor leaders), acid phosphatase, *C. albicans* glucoamylase, or the signal described in WO90/13646. In mammalian cells, mammalian signal sequences as well as viral secretory leaders, for example, the herpes simplex gD signal, can be used. The DNA for such precursor region is ligated in reading frame to DNA encoding the humanized anti-C3 antibody or antigen-binding fragment thereof.

Expression and cloning vectors contain a nucleic acid sequence that enables the vector to replicate in one or more selected host cells. Generally, in cloning vectors this sequence is one that enables the vector to replicate independently of the host chromosomal DNA, and includes origins of replication or autonomously replicating sequences. Such sequences are well known for a variety of bacteria, yeast, and viruses. The origin of replication from the plasmid pBR322 is suitable for most Gram-negative bacteria, the 2-υ. plasmid origin is suitable for yeast, and various viral origins (SV40, polyoma, adenovirus, VSV, and BPV) are useful for cloning vectors in mammalian cells. Generally, the origin of replication component is not needed for mammalian expression vectors (the SV40 origin may typically be used only because it contains the early promoter).

Expression and cloning vectors may contain a gene that encodes a selectable marker to facilitate identification of expression. Typical selectable marker genes encode proteins that confer resistance to antibiotics or other toxins, e.g., ampicillin, neomycin, methotrexate, or tetracycline, or alternatively, are complement auxotrophic deficiencies, or in other alternatives supply specific nutrients that are not present in complex media, e.g., the gene encoding D-alanine racemase for Bacilli.

One example of a selection scheme utilizes a drug to arrest growth of a host cell. Those cells that are successfully transformed with a heterologous gene produce a protein conferring drug resistance and thus survive the selection regimen. Examples of such dominant selection use the drugs neomycin, mycophenolic acid, and hygromycin. Common selectable markers for mammalian cells are those that enable the identification of cells competent to take up a nucleic acid encoding a humanized anti-C3 antibody, such as DHFR (dihydrofolate reductase), thymidine kinase, metallothionein-I and -II (such as primate metallothionein genes), adenosine deaminase, ornithine decarboxylase, and the like. Cells transformed with the DHFR selection gene are first identified by culturing all of the transformants in a culture medium that contains methotrexate (Mtx), a competitive antagonist of DHFR. An appropriate host cell when wild-type DHFR is employed is the Chinese hamster ovary (CHO) cell line deficient in DHFR activity (e.g., DG44).

Alternatively, host cells (particularly wild-type hosts that contain endogenous DHFR) transformed or co-transformed with DNA sequences encoding anti-C3 antibody, wild-type DHFR protein, and another selectable marker such as aminoglycoside 3'-phosphotransferase (APH), can be selected by cell growth in medium containing a selection agent for the selectable marker such as an aminoglycosidic antibiotic, e.g., kanamycin, neomycin, or G418. See, e.g., U.S. Pat. No. 4,965,199.

Where the recombinant production is performed in a yeast cell as a host cell, the TRP1 gene present in the yeast plasmid YRp7 (Stinchcomb et al., 1979, Nature 282: 39) can be used as a selectable marker. The TRP1 gene provides a selection marker for a mutant strain of yeast lacking the ability to grow in tryptophan, for example, ATCC No. 44076 or PEP4-1 (Jones, 1977, Genetics 85:12). The presence of the trp1 lesion in the yeast host cell genome then provides an effective environment for detecting transformation by growth in the absence of tryptophan. Similarly, Leu2p-deficient yeast strains such as ATCC 20,622 and 38,626 are complemented by known plasmids bearing the LEU2 gene.

In addition, vectors derived from the 1.6 µm circular plasmid pKD1 can be used for transformation of *Kluyveromyces* yeasts. Alternatively, an expression system for large-scale production of recombinant calf chymosin was reported for *K. lactis* (Van den Berg, 1990, Bio/Technology 8:135). Stable multi-copy expression vectors for secretion of mature recombinant human serum albumin by industrial strains of *Kluyveromyces* have also been disclosed (Fleer et al., 1991, Bio/Technology 9:968-975).

Expression and cloning vectors usually contain a promoter that is recognized by the host organism and is operably linked to the nucleic acid molecule encoding an anti-C3 antibody or polypeptide chain thereof. Promoters suitable for use with prokaryotic hosts include phoA promoter, β-lactamase and lactose promoter systems, alkaline phosphatase, tryptophan (trp) promoter system, and hybrid promoters such as the tac promoter. Other known bacterial promoters are also suitable. Promoters for use in bacterial systems also will contain a Shine-Dalgarno (S.D.) sequence operably linked to the DNA encoding the humanized anti-C3 antibody.

Many eukaryotic promoter sequences are known. Virtually all eukaryotic genes have an AT-rich region located approximately 25 to 30 bases upstream from the site where transcription is initiated. Another sequence found 70 to 80 bases upstream from the start of transcription of many genes is a CNCAAT region where N may be any nucleotide. At the 3' end of most eukaryotic genes is an AATAAA sequence that may be the signal for addition of the poly A tail to the 3' end of the coding sequence. All of these sequences are suitably inserted into eukaryotic expression vectors.

Examples of suitable promoting sequences for use with yeast hosts include the promoters for 3-phosphoglycerate kinase or other glycolytic enzymes, such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Inducible promoters have the additional advantage of transcription controlled by growth conditions. These include yeast promoter regions for alcohol dehydrogenase 2, isocytochrome C, acid phosphatase, derivative enzymes associated with nitrogen metabolism, metallothionein, glyceraldehyde-3-phosphate dehydrogenase, and enzymes responsible for maltose and galactose utilization. Yeast enhancers also are advantageously used with yeast promoters.

Anti-C3 antibody or antigen-binding fragment thereof according to the invention transcription from vectors in mammalian host cells is controlled, for example, by promoters obtained from the genomes of viruses such as polyoma virus, fowlpox virus, adenovirus (such as Adenovirus 2), bovine papilloma virus, avian sarcoma virus, cytomegalovirus, a retrovirus, hepatitis-B virus and Simian Virus 40 (SV40), from heterologous mammalian promoters, e.g., the actin promoter or an immunoglobulin promoter, or from heat-shock promoters, provided such promoters are compatible with the host cell systems.

The early and late promoters of the SV40 virus are conveniently obtained as an SV40 restriction fragment that also contains the SV40 viral origin of replication. The immediate early promoter of the human cytomegalovirus is conveniently obtained as a HindIII E restriction fragment. A system for expressing DNA in mammalian hosts using the bovine papilloma virus as a vector is disclosed in U.S. Pat. No. 4,419,446. A modification of this system is described in U.S. Pat. No. 4,601,978. See also Reyes et al., 1982, Nature 297:598-601, disclosing expression of human p-interferon cDNA in mouse cells under the control of a thymidine kinase promoter from herpes simplex virus. Alternatively, the rous sarcoma virus long terminal repeat can be used as the promoter.

Another useful element that can be used in a recombinant expression vector is an enhancer sequence, which is used to increase the transcription of a DNA encoding the anti-C3 antibody or the antigen-binding fragment thereof according to the invention by higher eukaryotes. Many enhancer sequences are now known from mammalian genes (e.g., globin, elastase, albumin, α-fetoprotein, and insulin). Typically, however, an enhancer from a eukaryotic cell virus is used. Examples include the SV40 enhancer on the late side of the replication origin (bp 100-270), the cytomegalovirus early promoter enhancer, the polyoma enhancer on the late side of the replication origin, and adenovirus enhancers. See also Yaniv, 1982, Nature 297:17-18 for a description of enhancing elements for activation of eukaryotic promoters. The enhancer may be spliced into the vector at a position 5' or 3' to the anti-C3 antibody-encoding sequence, but is preferably located at a site 5' from the promoter.

Expression vectors used in eukaryotic host cells (yeast, fungi, insect, plant, animal, human, or nucleated cells from other multicellular organisms) can also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding the anti-C3 antibody or the antigen-binding fragment thereof according to the invention. One useful transcription termination component is the bovine growth hormone polyadenylation region. See WO94/11026 and the expression vector disclosed therein. In some embodiments, anti-C3 antibodies can be expressed using the CHEF system. (See, e.g., U.S. Pat. No. 5,888,809).

Suitable host cells for cloning or expressing the DNA in the vectors herein are the prokaryote, yeast, or higher eukaryote cells described above. Suitable prokaryotes for this purpose include eubacteria, such as Gram-negative or Gram-positive organisms, for example, Enterobacteriaceae such as *Escherichia*, e.g., *E. coli*, *Enterobacter*, *Erwinia*, *Klebsiella*, *Proteus*, *Salmonella*, e.g., *Salmonella typhimurium*, *Serratia*, e.g., *Serratia marcescans*, and *Shigella*, as well as Bacilli such as *B. subtilis* and *B. licheniformis* (e.g., *B. licheniformis* 41 P disclosed in DD 266,710 published Apr. 12, 1989), *Pseudomonas* such as *P. aeruginosa*, and *Streptomyces*. One preferred *E. coli* cloning host is *E. coli* 294 (ATCC 31,446), although other strains such as *E. coli* B, *E. coli* X1776 (ATCC 31,537), and *E. coli* W3110 (ATCC 27,325) are suitable. These examples are illustrative rather than limiting.

In addition to prokaryotes, eukaryotic microbes such as filamentous fungi or yeast are suitable cloning or expression hosts for anti-C3 antibody-encoding vectors. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe*; *Kluyveromyces* hosts such as, e.g., *K. lactis*, *K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906), *K. thermotolerans*, and *K. marxianus*; *yarrowia* (EP 402,226); *Pichia pastors* (EP 183,070); *Candida*; *Trichoderma reesia* (EP 244,234); *Neurospora crassa*; *Schwanniomyces* such as *Schwanniomyces occidentalis*; and filamentous fungi such as, e.g., *Neurospora, Penicillium, Tolypocladium*, and *Aspergillus* hosts such as *A. nidulans* and *A. niger*.

Suitable host cells for the expression of glycosylated anti-C3 antibody or the antigen-binding fragment thereof are derived from multicellular organisms. Examples of invertebrate cells include plant and insect cells, including, e.g., numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* (silk worm). A variety of viral strains for transfection are publicly available, e.g., the L-1 variant of *Autographa californica* NPV and the Bm-5 strain of *Bombyx mori* NPV, and such viruses may be used, particularly for transfection of *Spodoptera frugiperda* cells.

Plant cell cultures of cotton, corn, potato, soybean, *petunia*, tomato, and tobacco can also be utilized as hosts.

The anti-C3 antibody or the antigen-binding fragment thereof according to the invention can also be incorporated in viral vectors, i.e., the polynucleotide encoding for the anti-C3 antibody or the antigen-binding fragment thereof is introduced into the viral vector and then expressed in the body of the patient after infection with the virus.

In another aspect, expression of the anti-C3 antibody or the antigen-binding fragment thereof according to the invention is carried out in vertebrate cells. The propagation of vertebrate cells in culture (tissue culture) has become routine procedure and techniques are widely available. Examples of useful mammalian host cell lines are monkey kidney CV1 line transformed by SV40 (COS-7, ATCC CRL 1651), human embryonic kidney line (293 or 293 cells subcloned for growth in suspension culture, (Graham et al., 1977, J. Gen Virol. 36: 59), baby hamster kidney cells (BHK, ATCC CCL 10), Chinese hamster ovary cells/-DHFR1 (CHO, Urlaub et al., 1980, Proc. Natl. Acad. Sci. USA 77: 4216; e.g., DG44), mouse sertoli cells (TM4, Mather, 1980, Biol. Reprod. 23:243-251), monkey kidney cells (CV1 ATCC CCL 70), African green monkey kidney cells (VERO-76, ATCC CRL-1587), human cervical carcinoma cells (HELA, ATCC CCL 2), canine kidney cells (MDCK, ATCC CCL 34), buffalo rat liver cells (BRL 3A, ATCC CRL 1442), human lung cells (W138, ATCC CCL 75), human liver cells (Hep G2, HB 8065), mouse mammary tumor (MMT 060562, ATCC CCL51), TR1 cells (Mather et al., 1982, Annals N.Y. Acad. Sci. 383: 44-68), MRC 5 cells, FS4 cells, and human hepatoma line (Hep G2).

Host cells are transformed with the above-described expression or cloning vectors for anti-C3 antibody or antigen-binding fragment thereof production and cultured in conventional nutrient media modified as appropriate for inducing promoters, selecting transformants, or amplifying the genes encoding the desired sequences.

The host cells used to produce the anti-C3 antibody or the antigen-binding fragment thereof according to the invention may be cultured in a variety of media. Commercially available media such as Ham's F10 (Sigma-Aldrich Co., St. Louis, Mo.), Minimal Essential Medium ((MEM), (Sigma-Aldrich Co.), RPMI-1640 (Sigma-Aldrich Co.), and Dulbecco's Modified Eagle's Medium ((DMEM), Sigma-Aldrich Co.) are suitable for culturing the host cells. In addition, any of the media described in one or more of Ham et al., 1979, Meth. Enz. 58: 44, Barnes et al., 1980, Anal. Biochem. 102: 255, U.S. Pat. Nos. 4,767,704, 4,657,866, 4,927,762, 4,560,655, 5,122,469, WO 90/103430, and WO 87/00195 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as gentamicin), trace elements (defined as inorganic compounds usually present at final concentrations in the micromolar range), and glucose or an equivalent energy source. Other supplements may also be included at appropriate concentrations that would be known to those skilled in the art. The culture conditions, such as temperature, pH, and the like, are those previously used with the host cell selected for expression, and will be apparent to the ordinarily skilled artisan.

When using recombinant techniques, the antibody or fragment thereof can be produced intracellularly, in the periplasmic space, or directly secreted into the medium. If the antibody is produced intracellularly, the cells may be disrupted to release protein as a first step. Particulate debris, either host cells or lysed fragments, can be removed, for example, by centrifugation or ultrafiltration. Carter et al., 1992, Bio/Technology 10:163-167 describes a procedure for isolating antibodies that are secreted to the periplasmic space of E. coli. Briefly, cell paste is thawed in the presence of sodium acetate (pH 3.5), EDTA, and phenylmethylsulfonylfluoride (PMSF) over about 30 minutes. Cell debris can be removed by centrifugation. Where the antibody is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants. A variety of methods can be used to isolate the antibody from the host cell.

The antibody composition prepared from the cells can be purified using, for example, hydroxylapatite chromatography, gel electrophoresis, dialysis, and affinity chromatography, with affinity chromatography being a typical purification technique. The suitability of protein A as an affinity ligand depends on the species and isotype of any immunoglobulin Fc domain that is present in the antibody. Protein A can be used to purify antibodies that are based on human gamma1, gamma2, or gamma4 heavy chains (see, e.g., Lindmark et al., 1983 J. Immunol. Meth. 62:1-13). Protein G is recommended for all mouse isotypes and for human gamma3 (see, e.g., Guss et al., 1986 EMBO J. 5:1567-1575). A matrix to which an affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a $C_{H3}$ domain, the Bakerbond ABX™ resin (J. T. Baker, Phillipsburg, N.J.) is useful for purification. Other techniques for protein purification such as fractionation on an ion-exchange column, ethanol precipitation, reverse phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody to be recovered.

Following any preliminary purification step(s), the mixture comprising the antibody or fragment thereof of interest and contaminants may be subjected to low pH hydrophobic interaction chromatography using an elution buffer at a pH between about 2.5-4.5, typically performed at low salt concentrations (e.g., from about 0-0.25M salt).

Also included are nucleic acids that hybridize under low, moderate, and high stringency conditions, as defined herein, to all or a portion (e.g., the portion encoding the variable region) of the nucleotide sequence represented by isolated polynucleotide sequence(s) that encode the anti-C3 antibody or the antigen-binding fragment thereof according to the invention. The hybridizing portion of the hybridizing nucleic acid is typically at least 15 (e.g., 20, 25, 30 or 50) nucleotides in length. The hybridizing portion of the hybridizing nucleic acid is at least 80%, e.g., at least 90%, at least 95%, or at least 98%, identical to the sequence of a portion or all of a nucleic acid encoding an anti-C3 polypeptide (e.g., a heavy chain or light chain variable region), or its complement. Hybridizing nucleic acids of the type described herein can be used, for example, as a cloning probe, a primer, e.g., a PCR primer, or a diagnostic probe.

In one embodiment, the present invention relates to an isolated polynucleotide or polynucleotides comprising a sequence encoding a heavy chain variable region set forth in SEQ ID NO: 20, SEQ ID NO: 22, or SEQ ID NO: 24, and a sequence encoding a light chain variable region set forth in SEQ ID NO: 21, SEQ ID NO: 23 and or ID NO: 25.

It is to be understood that in said anti-C3 antibodies and antibody fragments, the nucleic acid sequence coding for the CDRs remain unchanged (unchanged with respect to the amino acid they encode, equivalents of the DNA sequence due to the degeneracy of codons are possible) but the surrounding regions e.g., FR regions, can be engineered.

Articles of Manufacture

In another aspect, an article of manufacture containing materials useful for the treatment of the disorders described above is included. The article of manufacture comprises a container and a label. Suitable containers include, for example, bottles, vials, syringes, and test tubes. The containers may be formed from a variety of materials such as glass or plastic. The container holds a composition that is effective for treating the condition and may have a sterile access port. For example, the container may be an intravenous solution bag or a vial having a stopper pierceable by a hypodermic injection needle. The active agent in the composition is the anti-C3 antibody or the antigen-binding fragment thereof according to the invention. The label on or associated with the container indicates that the composition is used for treating the condition of choice. The article of manufacture may further comprise a second container comprising a pharmaceutically-acceptable buffer, such as phosphate-buffered saline, Ringer's solution, and dextrose solution. It may further include other materials desirable from a commercial and user standpoint, including other buffers, diluents, filters, needles, syringes, and package inserts with instructions for use.

The invention is further described in the following examples, which are not intended to limit the scope of the invention.

EXAMPLES

Example 1: C3 Mechanisms and Etiology of Geographic Atrophy

In patients with GA, an increased and uncontrolled activation of the complement system results in the destruction of the choriocapillaris, damage of RPE cells and finally loss of photoreceptors.

The relevance of complement activation for the pathophysiology of the disease is based on the following points:
A. Expression of Complement Proteins and Activation of the Complement System in the Retina in AMD Patients All proteins of the complement cascade were found to be expressed locally in different cell types in the retina. In patients, protein levels of several complement factors (e.g., C3, CFB and C5) are increased in drusen and GA lesions. In addition, increased levels of the complement activation products C3a, C4a, C3d, CBb were found to be increased in aqueous humor and plasma of AMD patients. Immunohistochemistry staining for the membrane attack complex (MAC) shows an increased deposition in the Bruch's membrane, RPE layer and choriocapillaris near GA lesions in patients.
B. Genetics of AMD GWAS studies identified the Y402H polymorphism in the complement factor H (CFH) as a major risk factor to develop AMD. An up to 7-fold increased risk was found in individuals homozygous for this mutation. CFH is the major negative regulator of the complement system. It enhances the decay of the C3 convertase C3bBb and regulates the proteolytic degradation of already deposited C3b. The Y402 polymorphism results in a decreased binding of CFH to other proteins and increased levels of complement activation products as well as an increased deposition of the MAC were found in homozygous patients. In addition, polymorphisms in other complement genes (e.g., CFB, C3, C7, C9) were linked with the development of AMD.
C. Clinical Studies with Complement Inhibitors Existing therapeutic strategies including treatment with a C3 inhibitor (APL-2) and a C5 inhibitor (ZIMURA®) reduced the growth of GA lesions in Phase 2 clinical trials. Inhibition of C3 will inhibit the C3 amplification loop and therefore inhibit the alternative, classical and lectin pathway of the complement system.

Example 2: Generation and Characterization of Anti-C3 Antibody Library

To generate the anti-C3 antibodies, 3 New Zealand white rabbits are immunized with native human C3 protein. Each animal receives 4 injections of the C3 protein at different timepoints with complete or incomplete Freund's adjuvant. The immune response of each animal is tested with an ELISA and the specific antibody titers in sera indicate excellent immune responses.

scFv antibody cDNA libraries are constructed from the RNA extracted from isolated rabbit PBMCs and spleen lymphocytes via PCR amplification. Coding sequences for the variable light- and heavy-domains are amplified separately and linked through a series of overlap PCR steps to give the final scFv products.

The amplified DNA sequences coding for the scFvs from rabbits are digested using appropriate restriction enzymes and ligated into the phagemid vectors. The phagemid vectors are transformed into *E. coli* TG1 electrocompetent cells which are well suited for antibody phage display library generation.

Example 3: Screen of Anti-C3 Antibody which Inhibits all Three Complement Pathways To screen for anti-C3 antibody with high affinities, scFvs displayed on phages are submitted to several rounds of biopanning (selection) against the native human C3. Stringency of the selection is increased with each round by either decreasing the concentration of the C3 protein used in the biopanning or increasing the stringency of the washes. Approximately 380 monoclonal phages are selected and screened for their ability to bind C3 in ELISA assays.

Based on the phage ELISA data and DNA fingerprint, a selection of the displayed scFvs is produced recombinantly as antibody proteins in a Fab format. The resulting proteins are evaluated for their ability to bind human C3 and C3b.

To identify antibodies that block all 3 complement pathways, antibodies are screened using an enzyme immunoassay for the qualitative determination of functional classical, lectin and alternative complement pathways in human serum using the WEISLAB® Complement system Screen (Svar Life Science AB, Malmö, Sweden). Clone IV (SEQ ID NO: 32) was identified as capable of inhibiting all three complement pathways, as shown in Table 6.

TABLE 6

Complement pathway inhibition by Clone IV at single dose of 2 μM for CP-, LP- and AP-dependent MAC formation.
Complement activation by Clone IV [%]

| Classical Pathway | Lectin Pathway | Alternative Pathway |
|---|---|---|
| 2.9 ± 0.0 | 0.5 ± 0.9 | −0.1 ± 0.2 |

The Clone IV sequence is shown in the following table 7.

TABLE 7

| Name | Amino acid sequence | SEQ ID NO: |
|---|---|---|
| Clone IV | QSVKESGGRLVTPGTPLTLTCTVSGFSLYNYAMN WVRQAPGKGLEWIGIINTDGNTNYASWAKGRFTI STTSSTTVDLKITSPTTEDTATYFCPRAVGYHHH ALDPWGPGTLVTVSSGGGGSGGGGSGGGGSGGGG ASELVLTQSPSVSAALGASAKLTCTLSSAHKTYT IDWYQQQQGEAPRYLMQLKSDGSYTKGTGVPDRF SGSSSGADRYLIIPSVQADDEADYYCGTDYGGGY VFGGGTQLTVTG | 32 |

Example 4: Reformatting, Humanization and Optimization Campaign

Reformatting and humanization: For antibody humanization and reformatting into the scFv antibody fragment format, the rabbit-derived Clone IV CDR sequences are grafted into the light chain variable (VL) and heavy chain variable (VH) domains of the human germline sequences. For the humanization of the VH, CDRs are grafted into the IMGT_hVH_3_30 framework. For the humanization of the VL, CDRs are grafted into IMGT_hVL_4-69 framework. The variable domains are connected using a (GGGGS)₄ linker (SEQ ID NO: 46) in a VL-linker-VH fashion. For framework 4, the IGLJ2*01 junction (J) gene sequence is used.

The reformatted and humanized variant Clone V (SEQ ID NO: 33) retains its ability to inhibit the classical and alternative complement pathways but shows lower binding affinity to C3 and C3b than the parental molecule Clone IV.

The variant is further modified by replacing additional rabbit-derived amino acids with germline sequences, thereby creating Clone VI (SEQ ID NO: 34). Its affinity towards the human C3 and C3b was comparable to the parental molecule and the thermal stability of the construct increased by 11.7° C.

The Clone V and Clone VI sequences are summarised in the following table 8.

TABLE 8

| Name | Amino acid sequence | SEQ ID NO: |
|---|---|---|
| Clone V | MQLVLTQSPSASASLGASVKLTCTLSSAHKTYTID WYQQQPEKGPRYLMQLKSDGSYTKGTGVPDRFS GSSSGAERYLTISSLQSEDEADYYCGTDYGGGYV FGGGTKLTVLGGGGSGGGGSGGGGSGGGGSQ VQVVESGGGSVQPGRSLRLSCAASGFSLYNYAM NWVRQAPGKGLEWIGIINTDGNTNYASWAKGRFT ISTDNSKNTLYLQMNSLRAEDTASYYCPRAVGYH HHALDPWGQGTSVTVSS | 33 |
| Clone VI | MQLVLTQSPSASASLGASVKLTCTLSSAHKTYTID WYQQQPEKGPRYLMQLKSDGSYTKGTGVPDRFS GSSSGAERYLTISSLQSEDEADYYCGTDYGGGYV FGGGTKLTVLGGGGSGGGGSGGGGSGGGGSQ VQVVESGGGSVQPGRSLRLSCAASGFSLYNYAM NWVRQAPGKGLEWIGIINTDGNTNYASWAKGRFT ISTDNSKNTLYLQMNSLRAEDTASYYCARAVGYH HHALDPWGQGTSVTVSS | 34 |

Affinity Maturation

Library construction: To improve the affinity of the molecule, site saturation libraries are constructed using Clone VI (SEQ ID NO: 34) as a template. Randomizations are performed on CDRs L1, L2, L3 and H3.

Biopanning: Libraries comprising light chain randomizations are combined into one library. Likewise, libraries comprising the heavy chain randomizations are combined into another library. Light and heavy chain libraries are subjected to biopanning against human C3. In rounds two, three and four of biopanning (ROP2-4), a competition against Clone IV at 50 µg/mL is introduced to increase the selection stringency and allow identification of binders with higher affinity than the parental molecule. Hits identified via the phage ELISA in ROP2-4 are subjected to sequencing. The most promising candidates from ROP4 are expressed and purified in a scFv format.

Hit characterization: All hits identified in ROP4 comprise amino acid substitutions in CDR L3 or CDR H3.

All hits were successfully expressed and purified. Best binding affinities to human C3 and C3b were observed for Clone VII (SEQ ID NO: 35), Clone VIII (SEQ ID NO: 36) and Clone IX (SEQ ID NO: 37) with C3 affinities of 1.1 nM, 184 µM and 1.3 nM, respectively.

Clone VII and Clone IX showed a comparable binding affinity and complement inhibition activity to the parental molecule Clone IV. Clone VIII showed an approximately 10-fold increase in the binding affinity to C3 and C3b, and a superior performance in the complement inhibition assays, compared to Clone IV.

The sequences of Clones VII, VIII, and IX are summarised in the following table 9.

TABLE 9

| Name | Amino acid sequence | SEQ ID NO: |
|---|---|---|
| Clone VII | MQLVLTQSPSASASLGASVKLTCTLSSAHKTYTID WYQQQPEKGPRYLMQLKSEGSYTKGTGVPDRFS GSSSGAERYLTISSLQSEDSAVYYCGTEGVGGYV FGCGTKLTVLGGGGSGGGGSGGGGSGGGGSQ VQVVESGGGSVQPGRSLRLSCAVSGFSLYNYAM NWVRQAPGKCLEWIGIINVGGGTNYASWAKGRFT ISTDNSKNTVYLQMNSLRAEDTASYYCARAVGYH HHALDPWGQGTSVTVSS | 35 |
| Clone VIII | MQLVLTQSPSASASLGASVKLTCTLSSAHKTYTID WYQQQPEKGPRYLMQLKSEGSYTKGTGVPDRFS GSSSGAERYLTISSLQSEDSAVYYCGTEGVGGYV FGCGTKLTVLGGGGSGGGGSGGGGSGGGGSQ VQVVESGGGSVQPGRSLRLSCAVSGFSLYNYAM NWVRQAPGKCLEWIGIINVGGGTNYASWAKGRFT ISTDNSKNTVYLQMNSLRAEDTASYYCARAVGYH HSRLDPWGQGTSVTVSS | 36 |
| Clone IX | MQLVLTQSPSASASLGASVKLTCTLSSAHKTYTID WYQQQPEKGPRYLMQLKSEGSYTKGTGVPDRFS GSSSGAERYLTISSLQSEDSAVYYCGTDGVGGYV FGCGTKLTVLGGGGSGGGGSGGGGSGGGGSQ VQVVESGGGSVQPGRSLRLSCAVSGFSLYNYAM NWVRQAPGKCLEWIGIINVGGGTNYASWAKGRFT ISTDNSKNTVYLQMNSLRAEDTASYYCARAVGYH HHALDPWGQGTSVTVSS | 37 |

Stabilization of the scFv

Stabilization of the scFv was performed by introduction of a disulfide bridge (VL 43C, VH 105C). Natural antibodies have a conserved interchain disulfide bridge between the constant light and constant heavy $C_{H1}$ domains that strongly stabilizes the interaction between light and heavy chains. The absence of this interchain disulfide bond in a scFv may lead to variable domain destabilization and formation of dimers, trimers and higher oligomer species, especially when formulated in high concentrations. The presence of a disulfide bond may thus stabilize the VH/VL interface of a scFv.

The stability of Clone VI's heavy chain framework was explored by introducing framework substitutions, thereby creating inter alia Clone X (SEQ ID NO: 38). Clone X and its disulfide bond stabilized variant Clone XI (SEQ ID NO: 39) were compared in a stability study at 37° C. and >100 mg/mL protein concentration. Two weeks incubation of Clone XI at 37° C. resulted in only 3.3% monomeric purity loss, while the parental molecule Clone X lost 60.4% monomeric content (Table 10).

TABLE 10

Concentration-dependent monomeric stability of the disulfide bond stabilized scFv Clone XI and the parental molecule Clone X at 37° C.

| Parameter | Clone XI | Clone X |
|---|---|---|
| Concentration at start | 152 mg/mL | 100 mg/mL |
| Monomeric content at start | 99.8% | 99.7% |
| Monomeric content after 2 weeks at 37° C. | 96.5% | 39.3% |

The sequences of Clones X and XI are summarised in the following table 11.

TABLE 11

| Name | Amino acid sequence | SEQ ID NO: |
|---|---|---|
| Clone X | MQLVLTQSPSASASLGASVKLTCTLSSAHKTYTID WYQQQPEKGPRYLMQLKSDGSYTKGTVPDRFS GSSSGAERYLTISSLQSEDEADYYCGTDYGGGYV FGGGTKLTVLGGGGSGGGGSGGGGSGGGGSQ VQVVESGGGSVQPGRSLRLSCTVSGFSLYNYAM NWVRQAPGKGLEWIGIINTDGNTNYASWAKGRFT ISTDNSKNTVYLQMNSLRAEDTASYYCARAVGYH HHALDPWGQGTSVTVSS | 38 |
| Clone XI | MQLVLTQSPSASASLGASVKLTCTLSSAHKTYTID WYQQQPEKCPRYLMQLKSDGSYTKGTVPDRFS GSSSGAERYLTISSLQSEDEADYYCGTDYGGGYV FGGGTKLTVLGGGGSGGGGSGGGGSGGGGSQ VQVVESGGGSVQPGRSLRLSCTVSGFSLYNYAM NWVRQAPGKGLEWIGIINTDGNTNYASWAKGRFT ISTDNSKNTVYLQMNSLRAEDTASYYCARAVGYH HHALDPWGCGTSVTVSS | 39 |

Final Optimization

The most promising affinity maturation substitutions and the disulfide bond stabilization were combined in Clone XII (SEQ ID NO: 40), Clone XIII (SEQ ID NO: 41) and Clone XIV (SEQ ID NO: 42).

Thermal stability and affinity to the human C3 and C3b are determined by the DSF and SPR assays. Clone XII, Clone XIII and Clone XIV showed melting temperatures of 70.4° C., 67.7° C. and 67.2° C., respectively. Binding affinity to the human C3 and C3b was 4.7 nM and 4.8 nM for Clone XII, 116 pM and 110 pM for Clone XIII, and 129 pM and 116 pM for Clone XIV, respectively.

Clone XII, Clone XIII and Clone XIV are also tested for their activity in the complement inhibition assay. The IC50 values for complement inhibition in the classical pathway were 0.098 µM, 0.06 µM and 0.05 µM for Clone XII, Clone XIII and Clone XIV, respectively, while the parental Clone IV showed IC50 of 0.08 µM. The IC50 values for complement inhibition in the alternative pathway were 0.21 µM, 0.26 µM and 0.25 µM for Clone XII, Clone XIII and Clone XIV, respectively, while Cone IV showed the IC50 of 0.28 µM. Collectively, Clone XIII and Cone XIV showed superior functional properties than Clone IV. Additionally, Clone XIII and Clone XIV were compared in the concentration-dependent stability study. Clone XIII could be concentrated to 150 mg/mL with no loss in the monomeric content and only 2.2% loss after 2 weeks of incubation at 37° C., while Cone XIV already lost 1.6% monomeric content with concentration to 50 mg/mL and an additional 2.3% after a 2-week incubation at 37° C.

The sequences of Clone XII, Clone XIII and Clone XIV are summarised in the following table 12.

TABLE 12

| Name | Amino acid sequence | SEQ ID NO: |
|---|---|---|
| Clone XII | MQLVLTQSPSASASLGASVKLTCTLSSAHKTYTID WYQQQPEKCPRYLMQLKSEGSYTKGTVPDRFS GSSSGAERYLTISSLQSEDEADYYCGTDYGGGYV FGGGTKLTVLGGGGSGGGGSGGGGSGGGGSQ VQVVESGGGSVQPGRSLRLSCAVSGFSLYNYAM NWVRQAPGKGLEWIGIINVGGGTNYASWAKGRFT ISTDNSKNTVYLQMNSLRAEDTASYYCARAVGYH HARLDPWGCGTSVTVSS | 40 |
| Clone XIII | MQLVLTQSPSASASLGASVKLTCTLSSAHKTYTID WYQQQPEKCPRYLMQLKSEGSYTKGTVPDRFS GSSSGAERYLTISSLQSEDEADYYCGTEGVGGYV FGGGTKLTVLGGGGSGGGGSGGGGSGGGGSQ VQVVESGGGSVQPGRSLRLSCAVSGFSLYNYAM NWVRQAPGKGLEWIGIINVGGGTNYASWAKGRFT ISTDNSKNTVYLQMNSLRAEDTASYYCARAVGYH HARLDPWGCGTSVTVSS | 41 |
| Clone XIV | MQLVLTQSPSASASLGASVKLTCTLSSAHKTYTID WYQQQPEKCPRYLMQLKSEGSYTKGTVPDRFS GSSSGAERYLTISSLQSEDEADYYCGTEGVGGYV FGGGTKLTVLGGGGSGGGGSGGGGSGGGGSQ VQVVESGGGSVQPGRSLRLSCAVSGFSLYNYAM NWVRQAPGKGLEWIGIINVGGGTNYASWAKGRFT ISTDNSKNTVYLQMNSLRAEDTASYYCARAVGYH HSRLDPWGCGTSVTVSS | 42 |

Final humanization: Immunogenicity risk prediction through EpiVax reveals an intermediate risk for Clone X (the parental construct of Clone XIII). EpiVax scores of ~39.36 and 14.86 were determined for the VH and VL, respectively. In addition, Clone XI showed human germline sequence identity 77% for the VH and 87% for the VL.

Clone IX evolution to Clone XIII comprised exclusively of CDR loop modifications, thus the liabilities identified in the FRs of Clone XI remained unchanged in Clone XIII. Therefore, additional germlining in the framework regions is performed.

Additionally, in silico analysis allows identification of the residues rarely occurring in the human antibody repertoire and thus harboring an increased immunogenicity risk. Accordingly, to further reduce the risk of immunogenicity, the following mutations VH S61D, W62S, A63V, and Y30S, and VL T56S were included in the candidates.

In the final humanization and optimization campaign, the inventors created Clone III, which was devoid of the critical post-translational modification (PTM) motifs, further humanized (human sequence identity of 86% and 89% for the VL and VH, respectively) and affinity matured.

In addition, the isomerization motif (DG) on CDR L2 was explored since it had a great impact on refolding yield and affinity. Therefore, Clone III was modified by introducing the mutation E50D, resulting in Clone II. Clone II showed a human sequence identity of 87% and 89% for the VL and VH, respectively.

An additional variant of Clone II was generated by the exchange of the entire CDR H2 to a fully human germline sequence (increasing human sequence identity to the human germline by an additional 7% in the VH), thus creating Clone I.

The inventors have thus ensured that the anti-C3 of the invention do not contain liability potentially causing isomerization, deamidation and oxidation. They further verified that the anti-C3 antibody or the antigen-binding fragment thereof according to the invention have acceptable viscosity strong storage stability, high affinity towards C3, C3b, show similar potency in classical, alternative and lectin pathway, show diffusion through porcine Bruch's membrane, and show no significant T-cell activation.

The exemplary antibodies of the invention include:
Clone I: comprising a variable heavy chain of SEQ ID NO: 20 and a variable light chain of SEQ ID NO: 21;
Clone II: comprising a variable heavy chain of SEQ ID NO: 22 and a variable light of SEQ ID NO: 23; and
Clone III: comprising a variable heavy chain of SEQ ID NO: 24 and a variable light chain of SEQ ID NO: 25.

Immunogenicity

The inventors have further assessed the immunogenicity of the scFv of the invention. The inventors have assessed the predicted immunogenicity of exemplary antibodies according to the invention: Clone I, Clone II and Clone III.

For this purpose, the inventors have used an in silico tool for predicting such T cell epitopes (EpiMatrix developed by EpiVax).

By screening the sequences of many human antibody isolates, EpiVax has identified several highly conserved HLA ligands which are believed to have a regulatory potential. Experimental evidence suggests many of these peptides are actively tolerogenic in most subjects. These highly conserved, regulatory, and promiscuous T cell epitopes are known as Tregitopes (De Groot et al. Blood. 2008 Oct. 15; 112(8):3303-11). The immunogenic potential of neo-epitopes contained in humanized antibodies can be effectively controlled in the presence of significant numbers of Tregitopes.

For the purposes of antibody immunogenicity analysis, EpiVax includes a Tregitope-adjusted EpiMatrix Score and corresponding prediction of anti-therapeutic antibody response. To calculate the Tregitope-adjusted EpiMatrix Score, the scores of the Tregitopes are deducted from the EpiMatrix Protein Score. The Tregitope-adjusted scores have been shown to be well correlated with observed clinical immune response for a set of 23 commercial antibodies (De Groot et al. Clin Immunol. 2009 May; 131(2):189-201).

The results on the EpiMatrix scale are summarised in the following table 13.

TABLE 13

| Molecule | VH Human germline sequence identity [%] | Epivax (VH) | Epivax (VL) | VL Human germline sequence identity [%] |
|---|---|---|---|---|
| Clone I | 96 | −55 | 8 | 87 |
| Clone II | 92 | −66 | 8 | 87 |

TABLE 13-continued

| Molecule | VH Human germline sequence identity [%] | Epivax (VH) | Epivax (VL) | VL Human germline sequence identity [%] |
|---|---|---|---|---|
| Clone III | 88 | −66 | 19 | 86 |
| Beovu | 80 | −66 | 32 | 88 |
| Lucentis | 76 | −49 | 14 | 87 |
| Avastin | 77 | −37 | −25 | 88 |
| Lampalizumab | 89 | −32 | −14 | 78 |
| Eylea | na | na | −16 | na |

Figures 2A, 2B:
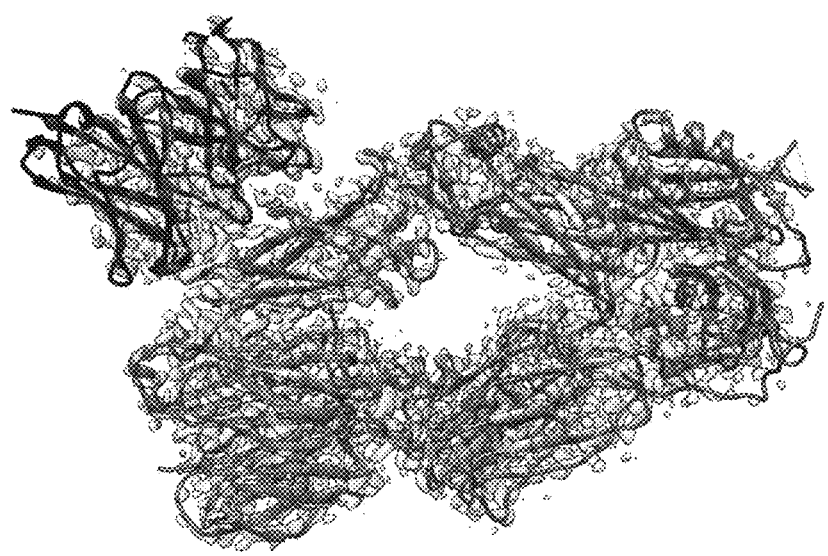
FIG. 2A shows SEQ ID NO: 55 which is part of the C3 sequence as set forth in in SEQ ID NO: 47, in which the epitope residues are in bold and underlined.
FIG. 2B shows the EM-structure of C3c:Clone I complex, in which the C3c structure is depicted in grey and the scFv structure in black ribbon representation, respectively. The final EM map is shown as semitransparent surface at a contour level of 0.214.

Sequences of the antibody of the invention score on the low end of EpiMatrix scale, indicating that the scFv of the invention has a strongly limited potential for immunogenicity. Said EpiMatrix scale is well known by the person skilled in the art and can be found inter alia in FIG. 2 of the publication Mufarrege et al. Clin Immunol., 2017 March; 176:31-41.

Example 5: Generation of Comparative Compounds

A. APL-1 Surrogate and APL-2 Surrogate

For comparison purposes, the inventors have developed several derivatives of compstatin, as follows:
an APL-1 surrogate: a PEGylated mono compstatin derivative (designed hereinafter as "Comparative Compound A1" or "Compound A1")
an APL-2 surrogate: a PEGylated dimerized compstatin derivative (designed hereinafter as "Comparative Compound A2" or "Compound A2").

These compounds are disclosed as APL-1 and APL-2 in the patent application US20200282012A1. They are further disclosed in:
Ricklin D, Lambris J D. Compstatin: a complement inhibitor on its way to clinical application. Adv Exp Med Biol. 2008; 632:273-292. doi:10.1007/978-0-387-78952-1_20 and
Mastellos D C, Ricklin D, Lambris J D. Clinical promise of next-generation complement therapeutics. Nat Rev Drug Discov. 2019; 18(9):707-729. doi:10.1038/s41573-019-0031-6.

The Compound A1 is an anti-C3 cyclic peptide derived from compstatin. Compound A2 was further developed based on the Compound A1 to extend its circulating half-life and improve its solubility in serum. Compound A2 comprises two peptide moieties linked via a linear 40 kDa PEG linker.

The sequences of Compound A1 and Compound A2 are summarised in the following Table 14.

TABLE 14

| Name | Amino acid sequence | Core sequence | Comments |
|---|---|---|---|
| Compound A1 | Ac-I-[CV-Trp(Me)-QDWGAHRC]-T-NH$_2$ (SEQ ID NO: 49) | ICVWQDWGAHRCT (SEQ ID NO: 49) | The compound A1 is acetylated at the C terminus. The tryptophan in position 4 is a 1-methyl tryptophan. Brackets indicate cyclization of the peptide via the Cys residues |
| Compound A2 | Gly-I-[CV-Trp(Me)-QDWGAHRC]-T-NH$_2$ (SEQ ID NO: 50) | GICVWQDWGAHRCT (SEQ ID NO: 50) | The tryptophan in position 4 is a 1-methyl tryptophan. Brackets indicate cyclization of the peptide via the Cys residues. The compound is dimerized via NHS-PEG40-NHS |

Additional data regarding structure and sequence of Compound A1 and Compound A2 are available in Adv Exp Med Biol. 2008; 632: 273-292.

B. NGM621 Surrogate

For comparison purposes, the inventors have developed a NGM compound, as disclosed in WO2019195136A1. This NGM compound is preferably as NGM621 surrogate, referred to hereinafter as "Comparative Compound A3" or "Compound A3". Said Compound A3 is anti-C3 IgG with the following features.

The relevant sequences are summarised as follows in the following table 15.

TABLE 15

| Name | Amino acid sequence | SEQ ID NO: |
|------|---------------------|------------|
| Compound A3 VH | QVQLVQSGAEVKKPGASVKVSCKASGYTFTDFYM DWVRQAPGQRLEWMGYIYPHNGGTTYNQQFTG RVTITVDKSASTAYMELSSLRSEDTAVYYCARRGG FDFDYWGQGTLVTVSS | 51 |
| Compound A3 VL | DIQMTQSPSSLSASVGDRVTITCKASENVDTYVS WYQQKPGKAPKLLIYGASNRYTGVPSRFSGSGSG TDFTFTISSLQPEDIATYHCGQSHSYPLTFGQGTK LEIKR | 52 |
| Compound A3 HC | QVQLVQSGAEVKKPGASVKVSCKASGYTFTDFYM DWVRQAPGQRLEWMGYIYPHNGGTTYNQQFTG RVTITVDKSASTAYMELSSLRSEDTAVYYCARRGG FDFDYWGQGTLVTVSSASTKGPSVFPLAPSSKST SGGTAALGCLVKDYFPEPVTVSWNSGALTSGVHT FPAVLQSSGLYSLSSVVTVPSSSLGTQTYICNVNH KPSNTKVDKKVEPKSCDKTHTCPPCPAPELLGGP SVFLFPPKPKDTLMISRTPEVTCVVVDVSHEDPEV KFNWYVDGVEVHNAKTKPREEQYNSTYRVVSVLT VLHQDWLNGKEYKCKVSNKALPAPIEKTISKAKGQ PREPQVYTLPPSRDELTKNQVSLTCLVKGFYPSDI AVEWESNGQPENNYKTTPPVLDSDGSFFLYSKLT VDKSRWQQGNVFSCSVMHEALHNHYTQKSLSLS PGK | 53 |
| Compound A3 LC | DIQMTQSPSSLSASVGDRVTITCKASENVDTYVS WYQQKPGKAPKLLIYGASNRYTGVPSRFSGSGSG TDFTFTISSLQPEDIATYHCGQSHSYPLTFGQGTK LEIKRTVAAPSVFIFPPSDEQLKSGTASVVCLLNN | 54 |

TABLE 15-continued

| Name | Amino acid sequence | SEQ ID NO: |
|------|---------------------|------------|
| | FYPREAKVQWKVDNALQSGNSQESVTEQDSKDST YSLSSTLTLSKADYEKHKVYACEVTHQGLSSPVTK SFNRGEC | |

The inventors further developed a NGM621 surrogate in a Fab format, based on the above mentioned sequence. Said compound is referred to as "Compound A3 Fab".

Example 6: Comparative Data

A. Different Mechanism of Action

The exemplary antibody of the invention and the comparative compounds have distinctive mechanisms of action and distinctive features, as summarised below:

the antibody of the invention inhibits C3 and C3b,
APL-2 inhibits C3 and C3b,
NGM621 inhibits C3, and
ZIMURA FO inhibits C5.

The inventors have shown that contrary to NGM621, the exemplary antibody of the invention Clone I binds to C3 and C3b with similar affinity, as illustrated in the following table 16.

TABLE 16

| | Exemplary antibody of the invention (Clone I) | NGM621* |
|---|---|---|
| C3 (Kd, nM) | 0.16 | 0.34 |
| C3b (Kd, nM) | 0.14 | >34 |

*published data Alexander Loktev et al. "NGM621 is a potent inhibitory anti-complement C3 antibody in development for treatment of geographic atrophy" ARVO 2020 Meeting, Poster B0267.

B. ScFv Format can Deliver More Drug Molecules Per IVT Injection

The inventors established the mass weight, the injection volume and the potentials doses of an exemplary antibody according to the invention and the Comparative Compound A2, Comparative Compound A3 and ZIMURA® (data available in the literature), as illustrated in the following table 17.

TABLE 17

| | Exemplary antibody of the invention (Clone I) | APL-2 | Comparative Compound A3 | ZIMURA ®** |
|---|---|---|---|---|
| Mw (kDa) | 26 | 43 | 150 | 54 |
| Injection volume (ul) | 50 | 100 | 100 | 100 |
| Dose (mg) | 7.5 | 15 | 15 | 2 |
| Dose (nmol) | 287 | 574 | 347 | 100 | 37 |

The antibody of the invention proves to provide higher drug amount per IVT administered to the eye, contributing to achieving greater complement inhibition in the eye.

C. ScFv Format Allows Better Retinal Penetration after Equimolar Intravitreal Injection, Compared to Fab or IgG.

Figure 1B:
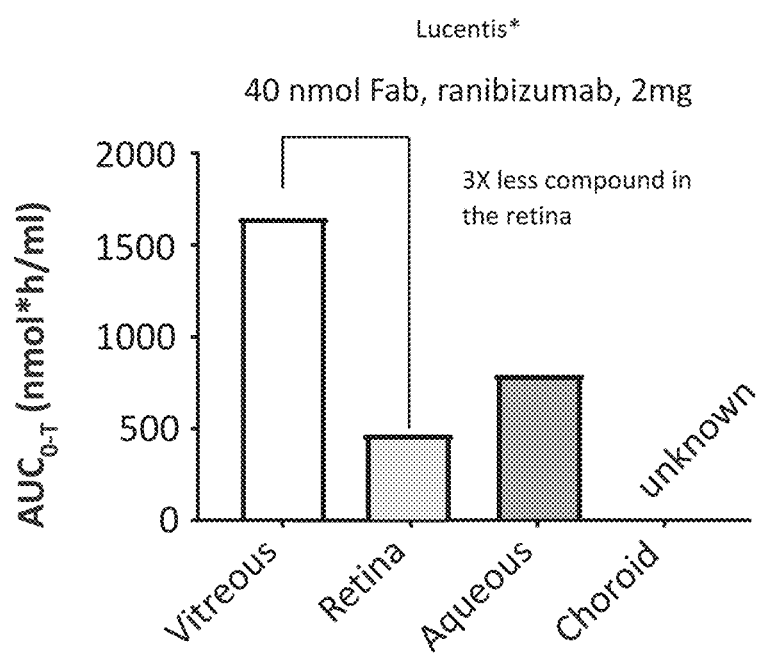
FIG. 1B depicts the retinal exposure level of a Fab intravitreal injection (40 nmol Fab, ranibizumab, 2 mg). The data are adapted from adapted from: Invest Ophthalmol Vis Sci. 2005 February; 46(2):726-33.

The inventors have compared the retinal penetration of a scFv (brolucizumab) and a Fab (ranibizumab) after equimolar intravitreal injection in cynomolgus monkey. The data indicate that scFv format allows an improved retinal penetration compared to Fab or IgG. Therefore, the antibodies of the invention in the scFv format are expected to achieve superior retinal exposure levels compared to a Fab upon intravitreal administration (FIGS. 1A and 1B).

Example 7: Potency and In Vitro Activity of the scFv of the Invention and Comparison with Comparative Compound A1 and Comparative Compound A3

For determination of a functional potency and comparison between exemplary scFv of the invention, the following assay are carried out: complement inhibition assay measuring generation of the membrane attack complex and a Hemolytic assay.

A. Materials and Methods a. Complement Inhibition Assay

To monitor inhibition of the complement system in human serum, the scFv of the invention or the comparator molecules are tested using an enzyme immunoassay for the qualitative determination of functional classical, lectin and alternative complement pathways in human serum using the WEISLAB® Complement system Screen (Svar Life Science AB, Malmö, Sweden), following the supplier's instructions. The amount of C5b-C9 neoantigen generated is proportional to the functional activity of complement pathways. The scFv of the invention and the comparator molecules are tested in a concentration response curve and the IC50 for the inhibition is calculated using the GraphPadPrism software and a non-linear, 4 parameters curve regression.

b. Hemolytic Assay

Anti-C3 antibody fragments are evaluated for their ability to inhibit hemolysis of antibody-sensitized sheep erythrocytes mediated by Classical Pathway (CP) or Alternative Pathway (AP) activation in human serum. For this, sheep erythrocytes are coated with hemolysin (rabbit anti-sheep antibodies) on the surface to activate the complement system in human serum resulting in C3 activation and subsequent formation of the Membrane Attack Complex (MAC). The MAC assembles on the membrane of sheep erythrocytes leading to cell lysis. The level of hemoglobin released from lysed erythrocytes is measured at OD 414 nm and is proportional to the complement activity present in the serum sample. For determining the ability of anti-C3 molecules to inhibit CP activity, human serum was diluted in GVB++ buffer (Complement technology) for optimal activation of the Classical Pathway (requires calcium and magnesium ions). Serial dilutions of anti-C3 test samples are prepared from this solution with a final concentration of 1% human serum for each datapoint (prior to addition to erythrocytes). The samples are incubated with antibody-sensitized sheep erythrocytes for 1 hour at 37° C. and released hemoglobin is measured in the supernatant after a centrifugation step.

The Alternative Pathway (AP) in human serum samples is spontaneously activated by rabbit erythrocytes. Since AP activation requires higher concentrations of serum, the Classical Pathway needs to be blocked with MgEGTA to chelate Ca2+ ions (AP only requires Mg2+ ions). AP activation results in C3 activation and subsequent formation of the Membrane Attack Complex (MAC). The MAC assembles on the membrane of rabbit erythrocytes leading to cell lysis. The level of hemoglobin released from lysed erythrocytes is measured at OD 414 nm and is proportional to the complement activity present in the serum sample.

B. Results

The results are summarised in the following table 18.

TABLE 18

| IC50 (nM) | | Clone I | Clone II | Clone III | Compound A1 | Compound A3 |
| --- | --- | --- | --- | --- | --- | --- |
| Classical Pathway | MAC deposition | 79 | 77 | 73 | 402 | 56 |
| | Hemolysis | 74 | 69 | 72 | 709 | 56 |
| Alternative Pathway | MAC deposition | 344 | 360 | 349 | 333 | 548 |
| | Hemolysis | 705 | 668 | 745 | 2535 | 207 |
| Lectin Pathway | MAC deposition | 67 | 71 | 64 | 222 | 58 |

The exemplary antibodies of the invention (Clone I, Clone II and Clone III) are more potent than Compound A1 (active component of Compound A2). Importantly, the inventors have shown the exemplary antibodies of the invention inhibits the classical and the lectin pathway more potently compared to Compound A1.

Clone I shows a similar activity on the alternative pathway like Compound A1.

Clone I shows a more potent inhibition of the classical pathway compared to Compound A1.

Clone I shows a more potent inhibition of the lectin pathway compared to Compound A1.

Clone I: The inventors have shown that an exemplary antibody of the invention (Clone I) inhibits all complement effector functions, with high affinity and potency.

Compound A1: The inventors have illustrated that the comparative Compound A1 inhibits all complement effector functions, with lower affinity and potency, when compared to the antibodies of the invention.

NGM621: The inventors have shown that the NGM621 surrogate, the Comparative Compound A3 shows no C3b inhibition.

ZIMURA®: The ZIMURA® compound targets only C5.

Example 8: Binding Affinity to Human C3 and C3b and Comparison of Binding Affinity of the Antibody of the Invention, Comparative Compound A1 and Comparative Compound A3

The inventors have assessed the binding affinity of exemplary scFv of the invention to human C3 as well as the binding affinity of Compound A1 and Compound A3 to human C3 and C3b.

A. Materials and Methods

The kinetic parameters of the candidates are determined using a surface plasmon resonance (SPR) and Biacore T100 device. C3 and different variants thereof (Table 19) are immobilized as a ligand on a HC30M SPR sensor chip (XanTec bionanalytics, Germany) using EDC/sulfo-NHC linking chemistry. Five increasing concentrations of each molecule (analyte) are consecutively injected using the single cycle kinetics (SCK) mode to determine the kinetic parameters. Regeneration between the candidates is done with 10 mM glycine*HCl, 2 M NaCl, pH 3.5. The data is fitted to a 1:1 Langmuir binding model and the kinetic parameters of on-rate (ka), off-rate (kd), and affinity (Ko) were determined.

Single nucleotide polymorphism (SNP) in C3 has been observed across the population and certain SNPs were identified in genome-wide association studies (GWAS) to correlate with an increased risk to develop AMD. Common SNP variants include P314L, which occurs in approximately 23.3% of population, and R102G, which has been reported to occur in approximately 26-29% of population. Very rare variants, which occur in less that 2.5% of the population include K155Q, R735W, S1619W, K65Q and R161W.

The inventors therefore measured the binding affinity of the scFv of the invention to the most commonly occurring C3 forms, i.e., R102G and P314L. Wild-type human C3, human C3 P314L and human C3 R102G are expressed in the CHO cell line using the ExpiFectamine CHO Expression Kit (Thermo Fisher Scientific). Proteins are expressed with N-terminal 6×His tag and purified using a HisTrap Excel HP column (GE Healthcare), followed by a size-exclusion chromatography step (SUPERDEX®20010/300GL; GE Healthcare).

B. Results

The Kinetic and affinity data of the scFv of the invention, Compound A1 (active component of Compound A2) and Compound A3 binding to human C3 and C3b respectively are listed in following table 19.

TABLE 19

| IC50 (nM) | Clone I | Clone II | Clone III | Compound A1 | Compound A3 Fab |
|---|---|---|---|---|---|
| Affinity human C3 (nM) | 0.152 | 0.022 | 0.151 | 6.2 | 0.34 |
| Affinity human C3b (nM) | 0.149 | 0.05 | 0.127 | 8.6 | >34 |

Compound A3 binds C3 with high affinity to intact human C3 (KD=0.34 nM), but shows significantly lower affinity (>100-fold) to C3 cleavage fragments C3b.

On the contrary, the exemplary antibody of the invention binds C3 with higher affinity than Compound A3. In addition, the exemplary antibody of the invention has approximately equivalent binding affinity for C3 and C3b.

It is noteworthy that the antibodies of invention bind with a higher affinity to human C3 and C3b compared to Compound A1 and Compound A3, enabling a more potent inhibition of C3. In comparison to Compound A3, the antibodies of the invention bind with higher affinity to C3b and will therefore block the generation of C3b in the C3 amplification loop as well the activity of already deposited C3b and C3b generated by alternative activation pathways.

Additional results are summarised in the following table 20.

TABLE 20

| Molecule | | C3 | C3b | cyno C3 | recombinant C3 | C3 SNP1 P314L | C3 SNP2 R102G |
|---|---|---|---|---|---|---|---|
| Clone II | $K_D$ (nM) | 0.022 | 0.05 | 0.07 | 0.035 | <0.04* | 0.021 |
| | $k_a$ (×$10^5$ $M^{-1}s^{-1}$) | 2.5 | 2.5 | 2.1 | 3 | 2.9 | 3.3 |
| | $k_d$ (×$10^{-6}$ $s^{-1}$) | 5.5 | 12 | 15 | 10 | <11 | 7 |
| Clone I | $K_D$ (nM) | 0.152 | 0.149 | 0.267 | 0.148 | 0.14 | 0.135 |
| | $k_a$ (×$10^5$ $M^{-1}s^{-1}$) | 3.1 | 3.2 | 2.4 | 3.3 | 3 | 3.3 |
| | $k_d$ (×$10^{-6}$ $s^{-1}$) | 47 | 48 | 63 | 49 | 42 | 45 |
| Clone III | $K_D$ (nM) | 0.151 | 0.127 | 0.208 | 0.128 | 0.127 | 0.115 |
| | $k_a$ (×$10^5$ $M^{-1}s^{-1}$) | 2.4 | 2.5 | 2 | 2.7 | 2.5 | 2.8 |
| | $k_d$ (×$10^{-6}$ $s^{-1}$) | 36 | 31 | 43 | 35 | 32 | 32 |
| Compound A1 | $K_D$ (nM) | 6.2 | 8.6 | n.d. | 12.9 | 13.7 | n.d. |
| | $k_a$ (×$10^5$ $M^{-1}s^{-1}$) | 8.8 | 10.7 | | 4.99 | 4.47 | |
| | $k_d$ (×$10^{-6}$ $s^{-1}$) | 5470.9 | 9202.7 | | 6444.4 | 6139.1 | |

The inventors therefore confirmed that the antibodies of the invention including Clone I, Clone II and Clone III have a higher affinity to C3 and C3b and inhibits ⅔ complement activation more potent than Compound A1.

The high binding affinity of the exemplary antibodies contributes to prolong the time for neutralization of C3 after intravitreal injection and further allows a reduced injection frequency. The improved binding affinity and reduced injection frequency considerably ameliorate the efficacy of the treatment of patients. It also provides valuable benefits for the patient, especially an improved drug observance and compliance.

It is further noteworthy that the scFv of the invention bind wildtype C3 as well as the disease-relevant SNP C3 P314L with a higher affinity than Compound A1.

Example 9: Identification of the Antibody-Binding Epitope on Human Complement C3

Protein preparation: Complement Component C3c is the major fragment resulting from C3 cleavage by C3 convertase and factor I. C3c isolated from human plasma is purchased from Athens Research & Technology (Product number 16-16-030303), deglycosylated with PNGase F and purified by size exclusion chromatography on a SUPERDEX® 200 column. Peak fractions are pooled, concentrated using an Amicon filter device with 50 kDa cutoff and stored at −80° C.

Crystallization of scFv: Crystals are obtained using the hanging drop vapor diffusion method by mixing 0.1 µl of the protein with 0.1 µL of a reservoir solution containing 0.1 M ammonium acetate, 0.1 M Zinc chloride, 0.1 M BIS-TRIS pH 6.0 and 15% w/v PEG Smear High. Crystals of plate-like shape appear within one day. Crystals are cryo-protected with the reservoir solution supplemented with 30% v/v glycerol and flash frozen in liquid nitrogen.

Data collection and structure determination: Data are collected at 100 K at the beamline X10SA of the SLS in Villigen, Switzerland. 3600 frames with 0.1° per frame are collected on an EIGER X 16M detector. The data are processed with autoPROC. A model for molecular replacement is created with SCULPTOR within the PHENIX software suite using the previously determined X-ray structure of a similar scFv as template. Molecular replacement is performed with PHASER using the scFv model prepared with SCULPTOR as template. The structure is refined with Buster, model building and least square fit analysis is done with COOT.

Cryo-EM sample preparation and data collection: C3c is mixed with ScFv at a ratio of 1:1.2, incubated for 16 h at 277 K and purified with a SUPERDEX® 200 increase column. The peak fraction is concentrated to 36 µM and applied to a EM-grid (Quantifoil-1.2/1.3 Au 300). The cryo-EM grids are prepared using a Leica GP (Leica Microsystems). Grids are blotted for 2 s at 4° C. with 85% humidity and plunged into liquid ethane cooled by liquid nitrogen. Cryo-grids are screened on a Glacios microscope operated at a voltage of 200 kV with a Falcon III detector and grids of good quality are transferred to a Titan Krios microscope operated at 300 kV. Images are collected in super-resolution mode using a Falcon IV detector (Thermo Fisher Scientific) mounted post an energy filter with a calibrated pixel size of 0.745 Å per pixel. Micrographs are exposed with at total dose of 60 $e^-/Å^2$ and processed using CryoSPARC v3.1.1. Stacks are motion-corrected and binned twofold, resulting in a pixel size of 1.49 Å per pixel.

Cryo-EM image analysis: A total of 1,914,120 particles are picked using CryoSPARC template picker from 3622 micrographs. The picked particles are extracted with a box size of 348 pixels and binned to 174 pixels in CryoSPARC. The extracted particles are then subjected to 3 rounds of 2D classification in cryoSPARC-3.1.1. to remove ice, contaminants and aggregates, yielding 421,628 particles. The classes with clearly defined C3c-scFv densities are used for ab initio reconstruction in cryoSPARC-3.1.0. 245,993 particles are selected based on a 2D class Threshold of 0.9 and subjected to one round of uniform and non-uniform refinement. Particles are re-extracted with a box size of 348 pixels and two one further round of uniform and non-uniform refinement is performed. This resulted in a fourier shell resolution of 2.55 Å.

Model building: The X-ray structures of C3c (pdb 5FOB) and the scFv are built into the EM density with the help of CHIMERA, real-space refined with PHENIX and inspected with COOT. Interface analysis is done with PYMOL.

The structure of Clone I is determined by X-ray crystallography to a resolution of 1.4 Å. The structured contains two molecules per asymmetric unit. All residues were well defined within the electron density map except for residues the two N-terminal residues in chain A and B, the linker residues 115-132 in chain A and 114-133 in chain B and the C-terminal residue 253 in chain B.

Due to preferred orientation of the complex molecules on the EM-grids, the resolution was limited to 4-5 Å at the interface between C3c and the scFv which still allows placement of the X-ray derived models into the EM map. Residues within 6 Å proximity to the scFv were determined as binding-site residues, which correspond to amino acids 366, 392-396, 413-421, 425, 427, 442, 453, 478 on human Complement C3 (SEQ ID NO: 47). The results showed that Clone I binds to an epitope partly overlapping to the compstatin binding site but not limited to it. The enhanced binding affinity to C3 exhibited by the molecule of present invention compared to compstatin derivatives is likely to result from this extended binding interface. These results indicate that the molecule of present invention binds to C3 in a different mode compared to prior art C3 inhibitors, which is likely to contribute to its unique ability on inhibiting all three complement pathways, including the Classical pathway (CP), the Lectin pathway (LP), and the Alternative pathway (AP).

Example 10: In Vitro BrM Permeation Assay and BrM Permeability

Bruch's membrane forms the innermost layer of the choroid and structural changes are thought to trigger complement activation in GA patients. Since complement-driven destruction of the choriocapillaris plays a major role in the pathophysiology of GA, excellent diffusion through Bruch's membrane is an important feature of a complement inhibitor to treat this disease.

Therefore, the inventors evaluated the ability of the scFv of the invention to diffuse through Bruch's membrane in vitro and compared it to Compound A2 and Compound A3.

A. Materials and Methods

Porcine Bruch's membrane samples are used for this measurement. Porcine eyes are collected from the slaughterhouse) no more than 6 hours after the animals were sacrificed and stored at 4° C. until use (on same day).

Preparation of enriched Bruch's Membrane (BrM): The eyes are placed into a disposable petri-dish and any residual tissue surrounding the eyeball is removed. The eyeball is incised next to the iris with a scalpel and the front part of the eye as well as lens, vitreous and retinal tissue are removed from the eyecup. The enriched Bruch's membrane including overlying RPE monolayer is gently dislodged from the entire inside surface of the eyecup, placed a in Petri dish filled with PBS and carefully flattened out in the fluid. After that, the Bruch's membrane is transferred to Ussing chamber, the Ussing chamber closed and one compartment filled with 1 ml PBS for leakage test. If after 5 min no significant accumulation of fluid was observed in the second compartment, the membrane is considered intact. Bruch's preparation from 4 different eyes are used for each Ussing chamber.

Incubation of enriched Bruch's membrane with test samples: A mastermix of APL-2 surrogate (such as Compound A2) and anti-C3 scFvs or APL-2 surrogate (such as Compound A2) and NGM621 surrogate (such as Compound A3) in PBS (+0.02% NaN3+protease inhibitor mix (Complete Tablets, Mini EDTA-free, EASYpack; Roche)) sufficient for 4 Ussing chambers (1 ml per Ussing chamber) at 0.1 mg/ml final concentration for each compound is prepared. 1 ml of mastermix is added to one compartment (designated sample chamber) per Ussing chamber. 1 ml of PBS (+0.02% NaN3+protease inhibitors) is added to second compartment (designated diffusate chamber) per Ussing chamber. Ussing chambers are sealed with parafilm and incubated for at room temperature with gentle shake to facilitate diffusion.

Sampling and membrane integrity analysis: For sampling at different timepoints (4 h, 24 h, 48 h and 72 h) the solution in the single compartments is mixed by carefully pipetting up and down and 90 µl were transferred separately from each sample and diffusate chamber to collection tubes. At the end of the incubation period a membrane integrity test is performed using Sphero Carboxyl Polystyrene Blue Particles: the suspension is diluted 1:10 in PBS and 200 ul are added to one compartment (designated sample chamber) per Ussing chamber and incubated for 30 min. Accumulation of blue particles in the second compartment is observed and camera pictures are recorded to control for overall membrane integrity.

Sample analysis: 15 µl of each solution from the sample and diffusate chambers are effectively loaded on 2 precast polyacrylamide gels (NuPAGE Bis-Tris gels) together with a similar amount of stored mastermix as loading control. The first gel is analyzed by standard SDS-PAGE and Coomassie-based staining methods for protein detection (anti-C3 scFv). The second gel is analyzed by SDS-PAGE and Barium iodide staining for PEG detection (Compound A2).

Evaluation: Pictures of the SDS-gels are analyzed using ImageJ2 software (Fiji). Bands were quantified and represented as % test compound in the respective chamber, where 100% refers to the summed band intensities of sample and diffusate chamber in the same Ussing device.

B. Results

The ability to cross porcine BrM was compared for the scFv of the invention and a compstatin derivatives such as Compound A2 that were simultaneously incubated on BrM preparations from four different porcine eyes. Significantly higher amounts of the scFv crossed the BrM in all four membrane preparations compared to the APL-2 surrogate. Similarly, the ability to cross porcine BrM was compared for NGM621 surrogate (Compound A3) and an APL-2 surrogate (Compound A2) that were simultaneously incubated on BrM preparations from four different porcine eyes.

Figure 3:
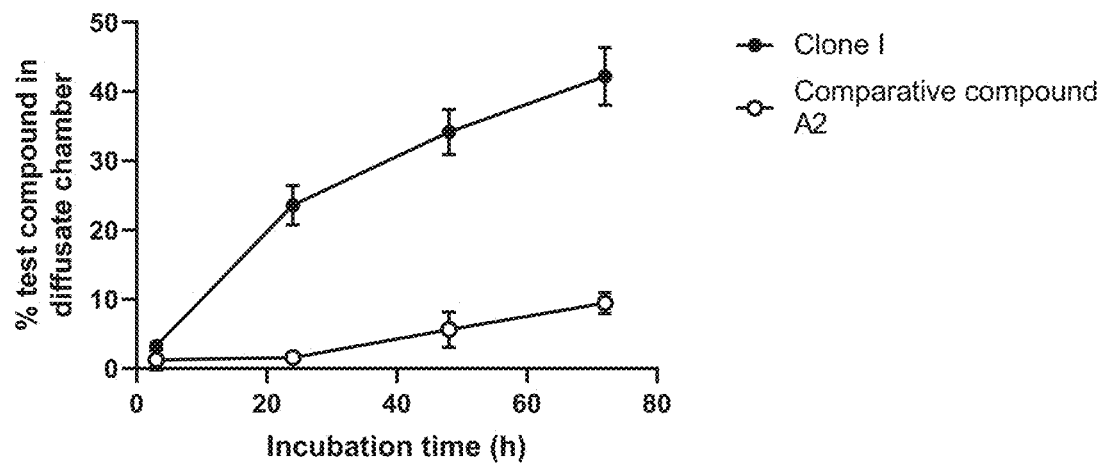
FIG. 3: This figure shows the in vitro diffusion of the clone I and the Comparative Compound A2 through porcine Bruch's membrane. Diffusion was measured over 72 hr in an Ussing chamber and the compound amount diffused through Bruch's membrane is given as compound measured in the diffusate chamber compared to total compound amount (sample and diffusate chamber). The total compound amount was set to 100%.
Figure 4:
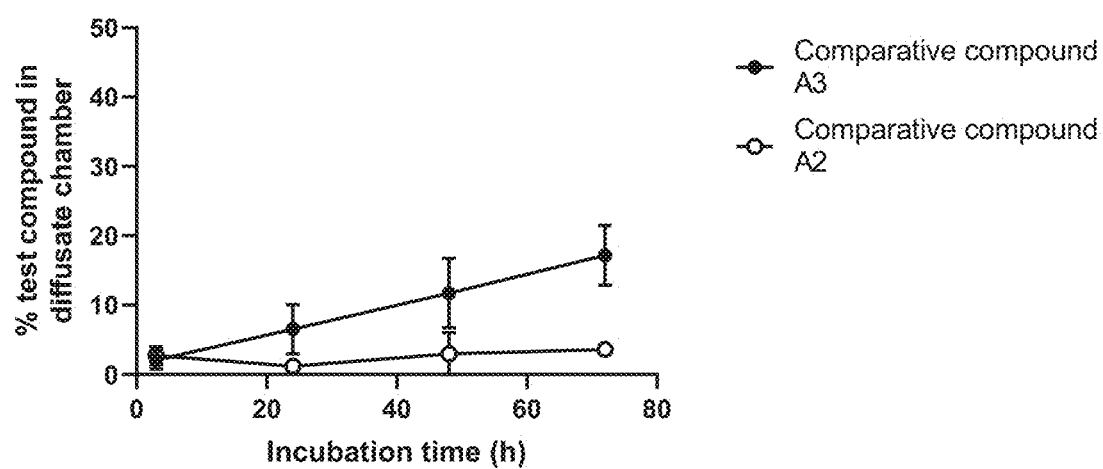
FIG. 4: This figure shows the in vitro diffusion of the Comparative Compound A3 and Comparative Compound A2 through porcine Bruch's membrane. Diffusion was measured over 72 hr in an Ussing chamber and the compound amount diffused through Bruch's membrane is given as compound measured in the diffusate chamber compared to total compound amount (sample and diffusate chamber). The total compound amount was set to 100%.

The exemplary antibody of the invention (Clone I) displayed a superior diffusion ability through Bruch's membrane compared to Compound A2 and Compound A3 (FIGS. 3 and 4).

Compound A2: No penetration

Compound A3: Reduced penetration compared to our exemplary antibody according to the invention.

ZIMURA®: The molecule was not tested. Since it contains the same large 40 kDa PEG moiety like APL-2, a similar behavior is expected.

Example 11: Protein Thermal Stability of the scFv of the Invention

A. Materials and Methods
Used Techniques: DSF

Differential scanning fluorimetry (DSF) measures protein unfolding by monitory changes in fluorescence as a function of temperature.

The temperature of protein unfolding ($T_m$) is tied to the stability of antibodies, specifically to aggregation during storage and long-term stability of the therapeutic product. The thermal transitions of monoclonal antibody CH2 and CH3 domains are typically invariant for different antibodies within an isotype, with the CH2 domain unfolding prior to the CH3 domain.

B. Results

The results are summarized in the following table 21.

TABLE 21

| COMPOUND | CLONE I | CLONE II | CLONE III |
|---|---|---|---|
| TM UNFOLDING ° C. (DSF) | 72.0/71.8 | 69.5/69.4 | 69.0/68.5 |

A high $T_m$ value means that fewer molecules populate the unfolded state at a given temperature. Thus, a high $T_m$ value is beneficial for therapeutic protein drugs as a high $T_m$ value sustains the active conformation at physiological temperatures.

These results confirm the excellent pharmaceutical properties of the exemplary antibodies of the invention. In particular, the improved thermal stability property contributes to an improved therapeutic efficacy while allowing a reduced injection dose and frequency to patients. In addition, the results are indicative of a higher shelf-life and improved stability in time of the therapeutic product. The improved stability and prolonged activity contribute to making the antibodies of the invention highly adapted for intravitreal administration.

Example 12: Immunogenicity Risk: Screen for Pre-Existing ADA

The inventors screen sera of healthy human donors for pre-existing ADA against Clone I using a bridging ELISA. Pre-existing ADAs present in serum from healthy human donors are bound by immobilized anti-C3 scFv. In a next step, ADAs are bound by the same anti-C3 scFv labeled with biotin and are detected by HRP-conjugated Streptavidin.

A. Materials and Methods

The scFv is biotin-labeled using the "Biotin Conjugation Kit (Fast, Type A)-Lightning-Link"-Kit (Expedeon/Abcam) following the suppliers' instructions. The unlabeled scFv is diluted to 0.5 µg/ml in PBS, 50 µl per well transferred to a 96 well plate and incubated overnight at 4° C. On the next day, the 96 well plate is washed with wash buffer (3×320 µl, 0.05% Tween 20 in PBS pH 7.4) and non-specific binding sites are blocked with 300 µl/well blocking buffer (SuperBlock Blocking Buffer; ThermoFisher scientific) for 30 min at room temperature. The wells are then washed with wash buffer (3×320 µl/well)

Human serum from healthy volunteers is diluted to 10% in PBS, 50 µl/well are added to the 96 well plate and the plate incubated for 1 hr at room temperature. The plate is then washed with wash buffer (3×320 µl/well), 50 µl/well of the biotinylated scFv (0.05 µg/ml in PBS) is added per well and incubated for 1 h at room temperature.

The plate is washed (3×320 µl/well was buffer), 50 µl/well Streptavidin-PolyHRP40 (SDT Reagenst; 1:5000 in PBS) is added and incubated for 30 min at room temperature.

The plate is washed (3×320 µl/well wash buffer), 50 µl/well TMB substrate (Invitrogen) is added and incubated for 5 min at room temperature. The reaction is then stopped by the addition of 50 µl/well 1N H2SO4. The absorption is measured at 450 nm. Pre-existing ADA will lead to an increased absorption.

B. Results

For the Clone I, pre-existing ADA were found in 9 out of 50 serum samples, showing an overall low risk of immunogenicity. These results confirm that the antibodies of the Example 13: Biophysical Characterization of the Antibodies of the Invention at High Concentrated Formulations Storage Stability Clone I, clone II and clone III are tested for storage stability. Samples are concentrated to 150 mg/ml (Vivaspin20 centrifugal device, 5 kDa MWCO at 3800×g) and stored at 25° C. and 40° C. for up to 4 weeks. Samples are analyzed for oligomerization (SE-HPLC) and chemical degradation (IEX-HPLC). The respective decrease in the monomeric content compared to the starting value is reported in Table 22. The starting monomeric purity as determined by SE-HPLC was 99.96% for each clone. The starting charge purity, as determined by IEX-HPLC was 98.07%, 97.16% and 96.76%, respectively for clone I, II and III.

Clone I, Clone II and Clone III showed an excellent monomeric and charge stability at 25° C. and 40° C. over the 4-week incubation period.

Viscosity at High Concentrations

The injection force required to deliver the drug via a standard intravitreal needle is dependent on the viscosity of the product and needs to be low enough to enable safe injection of the product by the physician. Therefore, low viscosities, typically below 15 mPa*s at 20° C. in the fully formulated product, are required.

Viscosity measurements are performed with the samples prepared for the storage stability study. In addition to the fully formulated samples (10 mM His pH 5.5, 275 mM sucrose, 0.02% w/v Polysorbate20), viscosity of each candidate is also measured in a minimal formulation (10 mM histidine pH 5.5). This is performed to evaluate the drug substance processability (e.g., filtration, pumping, diafiltration, etc.) of the candidates up to 125% of the final drug product concentration of 150 mg/ml.

Viscosity is measured at 20° C. at a shear-rate of 1000 $s^{-1}$ using a cone-plate-rheometer. Briefly, a stepwise increase of the shear rate up to 1,000 $s^{-1}$ is done collecting 100 data points, followed by a further increase of the shear rate up to 2000 $s^{-1}$, collecting another 10 data points. Finally, a stepwise decrease of the shear rate down to starting rate is done. The obtained viscosity data is presented in Table 22. Good drug product handling properties for filling and syringeability have been observed for all candidates The viscosity and stability properties of Clone I, II and III formulated at >150 mg/mL are summarized in table 22.

TABLE 22

| Candidates | Clone I | Clone II | Clone III | Formulation |
|---|---|---|---|---|
| Viscosity [mPa * s] | | | | 10 mM His pH 5.5 |
| Minimal buffer at 185 g/L | 5.4 | 4.5 | 3.2 | 10 mM His pH 5.5, |
| Fully formulated at 150 g/L | 3.9 | 3.9 | 3.3 | 275 mM sucrose, 0.02% w/v Polysorbate20 |
| Storage stability, SEC | | | | 10 mM His pH 5.5, |
| 4 weeks at 25° C. [D %] | 0.06 | 0.11 | 0.10 | 150 mM NaCl |
| 4 weeks at 40° C. [D %] | 0.37 | 1.59 | 0.84 | |
| Storage stability, IEX | | | | 10 mM His pH 5.5, |
| 4 weeks at 25° C. [D %] | 1.1 | 0.5 | 0.3 | 150 mM NaCl |
| 4 weeks at 40° C. [D %] | 2.4 | 3.3 | 3.6 | |

The inventors have shown that the exemplary antibodies of the invention display extraordinary stability at high concentrated formulations.

The invention claimed is:

1. A monoclonal anti-C3 antibody or an antigen-binding fragment thereof comprising a heavy chain variable region (VH), and a light chain variable region (VL),
   wherein the VH comprises the CDR-H1 sequence of SEQ ID NO: 1, the CDR-H2 sequence of SEQ ID NO: 2 or 15, and the CDR-H3 sequence of SEQ ID NO: 3; and
   wherein the VL comprises the CDR-L1 sequence of SEQ ID NO: 4, the CDR-L2 sequence of SEQ ID NO: 5 or 18, and the CDR-L3 sequence of SEQ ID NO: 6.

2. The monoclonal anti-C3 antibody or the antigen-binding fragment thereof according to claim 1,
   wherein the VH comprises the CDR-H1 sequence of SEQ ID NO: 1, the CDR-H2 sequence of SEQ ID NO: 2, and the CDR-H3 sequence of SEQ ID NO: 3; and the VL comprises the CDR-L1 sequence of SEQ ID NO: 4, the CDR-L2 sequence of SEQ ID NO: 5, and the CDR-L3 sequence of SEQ ID NO: 6, or
   wherein the VH comprises the CDR-H1 sequence of SEQ ID NO: 1, the CDR-H2 sequence of SEQ ID NO: 15, and the CDR-H3 sequence of SEQ ID NO: 3; and the VL comprises the CDR-L1 sequence of SEQ ID NO: 4, the CDR-L2 sequence of SEQ ID NO: 5, and the CDR-L3 sequence of SEQ ID NO: 6, or
   wherein the VH comprises the CDR-H1 sequence of SEQ ID NO: 1, the CDR-H2 sequence of SEQ ID NO: 15, and the CDR-H3 sequence of SEQ ID NO: 3; and the VL comprises the CDR-L1 sequence of SEQ ID NO: 4, the CDR-L2 sequence of SEQ ID NO: 18, and the CDR-L3 sequence of SEQ ID NO: 6, or
   wherein the VH comprises the CDR-H1 sequence of SEQ ID NO: 1, the CDR-H2 sequence of SEQ ID NO: 2, and the CDR-H3 sequence of SEQ ID NO: 3 and the VL comprises the CDR-L1 sequence of SEQ ID NO: 4, the CDR-L2 sequence of SEQ ID NO: 18, and the CDR-L3 sequence of SEQ ID NO: 6.

3. The monoclonal anti-C3 antibody or the antigen-binding fragment thereof according to claim 1, wherein the antibody or the antigen-binding fragment thereof comprises:
   a heavy chain variable region comprising an amino acid sequence at least 80% identical to the amino acid sequence of SEQ ID NO: 20, 22 or 24; and
   a light chain variable region comprising an amino acid sequence at least 80% identical to the amino acid sequence of SEQ ID NO: 21, 23 or 25.

4. The monoclonal anti-C3 antibody or the antigen-binding fragment thereof according to claim 1, comprising:
   a heavy chain variable region comprising an amino acid sequence at least 80% identical to the amino acid sequence of SEQ ID NO: 20, 22 or 24; and
   a light chain variable region comprising an amino acid sequence at least 80% identical to the amino acid sequence of SEQ ID NO: 21, 23 or 25;
   wherein the VH comprises the CDR-H1 sequence of SEQ ID NO: 1, the CDR-H2 sequence of SEQ ID NO: 2 or 15, the CDR-H3 sequence of SEQ ID NO: 3; and
   wherein the VL comprises the CDR-L1 sequence of SEQ ID NO: 4, the CDR-L2 sequence of SEQ ID NO: 5 or 18, and the CDR-L3 sequence of SEQ ID NO: 6.

5. The monoclonal anti-C3 antibody or the antigen-binding fragment thereof according to claim 1, wherein the antibody or the antigen-binding fragment thereof comprises:
   a heavy chain variable region comprising the amino acid sequence of SEQ ID NO: 20, 22 or 24; and
   a light chain variable region comprising the amino acid sequence of SEQ ID NO: 21, 23 or 25.

6. The monoclonal anti-C3 antibody or the antigen-binding fragment thereof according to claim 1, wherein the antibody or the antigen-binding fragment thereof comprises:
   a. a heavy chain variable region and a light chain variable region comprising the amino acid sequences of SEQ ID NO: 20 and SEQ ID NO: 21, respectively;
   b. a heavy chain variable region and a light chain variable region comprising the amino acid sequences of SEQ ID NO: 22 and SEQ ID NO: 23, respectively; or
   c. a heavy chain variable region and a light chain variable region comprising the amino acid sequences of SEQ ID NO: 24 and SEQ ID NO: 25, respectively.

7. The monoclonal anti-C3 antibody or the antigen-binding fragment thereof according to claim 1, wherein the antigen binding fragment is selected from the group consisting of a single chain variable fragment (scFv), a Fab fragment, a Fab' fragment, a Fv fragment, a diabody, and a small antibody mimetic.

8. The monoclonal anti-C3 antibody or the antigen-binding fragment thereof according to claim 7, wherein said antigen binding fragment is a single chain variable fragment (scFv).

9. The monoclonal anti-C3 antibody or the antigen-binding fragment thereof according to claim 8, wherein the antigen binding fragment is an scFv comprising an amino acid sequence selected from the group consisting of SEQ ID NO: 26, 27, 28, 29, 30 and 31.

10. The monoclonal anti-C3 antibody or the antigen-binding fragment thereof according to claim 1, wherein said monoclonal anti-C3 antibody or the antigen-binding fragment thereof binds to human C3 at a $K_D$<50 nM.

11. The monoclonal anti-C3 antibody or the antigen-binding fragment thereof according to claim 1, wherein said monoclonal anti-C3 antibody or the antigen-binding fragment thereof binds to human C3b at a $K_D$<50 nM.

12. A method of treating an eye or ocular disease that is mediated by C3-mediated complement activation in a subject in need thereof, the method comprising: administering to the subject an effective amount of the monoclonal anti-C3 antibody or the antigen-binding fragment thereof according to claim 1.

13. The method of claim 12, wherein the eye or ocular disease is selected from the group consisting of retinopathy, proliferative retinopathy (PR), retinopathy of prematurity, ischemic retinopathy, diabetic retinopathy (DR), proliferative diabetic retinopathy (PDR), non-proliferative diabetic retinopathy, diabetic macular edema (DME), diabetic macular ischemia (DMI), age-related macular degeneration (AMD), dry AMD, wet AMD, geographic atrophy (GA), retinitis pigmentosa, inherited retinal dystrophy, myopic degeneration, retinal vein occlusions, retinal artery occlusions, endophthalmitis, uveitis, cystoid macular edema, choroidal neovascular membrane secondary to any retinal diseases, optic neuropathies, glaucoma, retinal detachment, toxic retinopathy, radiation retinopathy, traumatic retinopathy, drug-induced retinal vasculopathy, retinal neovascularisation, polypoidal choroidal vasculopathy, retinal vasculitis, retinal microaneurysm, retrolental fibroplasia, chorioretinitis, Fuch's dystrophy, macular telangiectasia, usher syndrome, Paroxysmal nocturnal hemoglobinuria (PNH), and Stargardt disease.

14. A method of treating age-related macular degeneration, geographic atrophy, neovascular glaucoma, or diabetic retinopathy in a subject in need thereof, the method comprising: administering to the subject an effective amount of the monoclonal anti-C3 antibody or the antigen-binding fragment thereof according to claim 1.

15. The method of claim 14, wherein the eye or ocular disease is geographic atrophy.

16. A method of detecting Complement C3 in a biological sample, the method comprising contacting the biological sample with the monoclonal anti-C3 antibody or the antigen-binding fragment thereof according to claim 1 and detecting said monoclonal anti-C3 antibody bound to said Complement C3.

17. A pharmaceutical composition comprising the monoclonal anti-C3 antibody or the antigen-binding fragment thereof according to claim 1 and a pharmaceutically acceptable carrier.

18. The method of claim 12, wherein the monoclonal anti-C3_antibody or the antigen-binding fragment thereof is administered parenterally, intravenously, intravitreally, or subcutaneously.

19. The method of claim 18, wherein the antibody or the antigen-binding fragment thereof is administered intravitreally.

20. An isolated polynucleotide or isolated polynucleotides encoding the antibody or the antigen-binding fragment thereof according to claim 1.

21. An expression vector comprising the isolated polynucleotide or polynucleotides of claim 20.

22. An isolated host cell comprising the expression vector according to claim 21.

23. A method for producing a monoclonal anti-C3 antibody or an antigen-binding fragment thereof comprising:
   a. obtaining the isolated host cell according to claim 22, and
   b. cultivating the host cell.

24. The method according to claim 23, further comprising recovering the antibody or the antigen-binding fragment thereof.

25. An anti-C3 antibody single chain fragment comprising the amino acid sequence of SEQ ID NO: 26.

26. An anti-C3 antibody single chain fragment comprising the amino acid sequence of SEQ ID NO: 27.

27. An anti-C3 antibody single chain fragment comprising the amino acid sequence of SEQ ID NO: 28.

28. An anti-C3 antibody single chain fragment comprising the amino acid sequence of SEQ ID NO: 29.

29. An anti-C3 antibody single chain fragment comprising the amino acid sequence of SEQ ID NO: 30.

30. An anti-C3 antibody single chain fragment comprising the amino acid sequence of SEQ ID NO: 31.

31. A pharmaceutical composition comprising the anti-C3 antibody single chain fragment according to claim 25 and a pharmaceutically acceptable carrier.

32. A pharmaceutical composition comprising the anti-C3 antibody single chain fragment according to claim 26 and a pharmaceutically acceptable carrier.

33. A pharmaceutical composition comprising the anti-C3 antibody single chain fragment according to claim 27 and a pharmaceutically acceptable carrier.

34. A pharmaceutical composition comprising the anti-C3 antibody single chain fragment according to claim 28 and a pharmaceutically acceptable carrier.

35. A pharmaceutical composition comprising the anti-C3 antibody single chain fragment according to claim 29 and a pharmaceutically acceptable carrier.

36. A pharmaceutical composition comprising the anti-C3 antibody single chain fragment according to claim 30 and a pharmaceutically acceptable carrier.

37. A method of treating age-related macular degeneration, geographic atrophy, neovascular glaucoma, or diabetic retinopathy in a subject in need thereof, the method comprising: administering to the subject an effective amount of the anti-C3 antibody single chain fragment according to claim 25.

38. A method of treating age-related macular degeneration, geographic atrophy, neovascular glaucoma, or diabetic retinopathy in a subject in need thereof, the method comprising: administering to the subject an effective amount of the anti-C3 antibody single chain fragment according to claim 26.

39. A method of treating age-related macular degeneration, geographic atrophy, neovascular glaucoma, or diabetic retinopathy in a subject in need thereof, the method comprising: administering to the subject an effective amount of the antibody or the anti-C3 antibody single chain fragment according to claim 27.

40. A method of treating age-related macular degeneration, geographic atrophy, neovascular glaucoma, or diabetic retinopathy in a subject in need thereof, the method comprising: administering to the subject an effective amount of the anti-C3 antibody single chain fragment according to claim 28.

41. A method of treating age-related macular degeneration, geographic atrophy, neovascular glaucoma, or diabetic retinopathy in a subject in need thereof, the method comprising: administering to the subject an effective amount of the anti-C3 antibody single chain fragment according to claim 29.

42. A method of treating age-related macular degeneration, geographic atrophy, neovascular glaucoma, or diabetic retinopathy in a subject in need thereof, the method comprising: administering to the subject an effective amount of the anti-C3 antibody single chain fragment according to claim 30.

43. A method of treating geographic atrophy in a subject in need thereof, the method comprising: administering to the subject an effective amount of the anti-C3 antibody single chain fragment according to claim 25.

44. A method of treating geographic atrophy in a subject in need thereof, the method comprising: administering to the subject an effective amount of the anti-C3 antibody single chain fragment according to claim 26.

45. A method of treating geographic atrophy in a subject in need thereof, the method comprising: administering to the subject an effective amount of the anti-C3 antibody single chain fragment according to claim 27.

46. A method of treating geographic atrophy in a subject in need thereof, the method comprising: administering to the subject an effective amount of the anti-C3 antibody single chain fragment according to claim 28.

47. A method of treating geographic atrophy in a subject in need thereof, the method comprising: administering to the subject an effective amount of the anti-C3 antibody single chain fragment according to claim 29.

48. A method of treating geographic atrophy in a subject in need thereof, the method comprising: administering to the subject an effective amount of the anti-C3 antibody single chain fragment according to claim 30.

49. A method of preventing age-related macular degeneration, geographic atrophy, neovascular glaucoma, or diabetic retinopathy in a subject in need thereof, the method comprising: administering to the subject an effective amount of the monoclonal anti-C3 antibody or the antigen-binding fragment thereof according to claim 1.

50. A method of preventing age-related macular degeneration, geographic atrophy, neovascular glaucoma, or diabetic retinopathy in a subject in need thereof, the method comprising: administering to the subject an effective amount of the anti-C3 antibody single chain fragment according to claim 44.

51. A method of preventing age-related macular degeneration, geographic atrophy, neovascular glaucoma, or diabetic retinopathy in a subject in need thereof, the method comprising: administering to the subject an effective amount of the anti-C3 antibody single chain fragment according to claim 45.

52. A method of preventing age-related macular degeneration, geographic atrophy, neovascular glaucoma, or diabetic retinopathy in a subject in need thereof, the method comprising: administering to the subject an effective amount of the anti-C3 antibody single chain fragment according to claim 46.

53. A method of preventing age-related macular degeneration, geographic atrophy, neovascular glaucoma, or diabetic retinopathy in a subject in need thereof, the method comprising: administering to the subject an effective amount of the anti-C3 antibody single chain fragment according to claim 47.

54. A method of preventing age-related macular degeneration, geographic atrophy, neovascular glaucoma, or diabetic retinopathy in a subject in need thereof, the method comprising: administering to the subject an effective amount of the anti-C3 antibody single chain fragment according to claim 48.

55. A method of preventing age-related macular degeneration, geographic atrophy, neovascular glaucoma, or diabetic retinopathy in a subject in need thereof, the method comprising: administering to the subject an effective amount of the anti-C3 antibody single chain fragment according to claim 49.

56. A method of preventing geographic atrophy in a subject in need thereof, the method comprising: administering to the subject an effective amount of the anti-C3 antibody single chain fragment according to claim 44.

57. A method of preventing geographic atrophy in a subject in need thereof, the method comprising: administering to the subject an effective amount of the anti-C3 antibody single chain fragment according to claim 45.

58. A method of preventing geographic atrophy in a subject in need thereof, the method comprising: administering to the subject an effective amount of the anti-C3 antibody single chain fragment according to claim 46.

59. A method of preventing geographic atrophy in a subject in need thereof, the method comprising: administering to the subject an effective amount of the anti-C3 antibody single chain fragment according to claim 47.

60. A method of preventing geographic atrophy in a subject in need thereof, the method comprising: administering to the subject an effective amount of the anti-C3 antibody single chain fragment according to claim 48.

61. A method of preventing geographic atrophy in a subject in need thereof, the method comprising: administering to the subject an effective amount of the anti-C3 antibody single chain fragment according to claim 49.

62. A method of treating age-related macular degeneration in a subject in need thereof, the method comprising: administering to the subject an effective amount of the anti-C3 antibody single chain fragment according to claim 44.

63. A method of treating age-related macular degeneration in a subject in need thereof, the method comprising: administering to the subject an effective amount of the anti-C3 antibody single chain fragment according to claim 45.

64. A method of treating age-related macular degeneration in a subject in need thereof, the method comprising: administering to the subject an effective amount of the anti-C3 antibody single chain fragment according to claim 46.

65. A method of treating age-related macular degeneration in a subject in need thereof, the method comprising: administering to the subject an effective amount of the anti-C3 antibody single chain fragment according to claim 47.

66. A method of treating age-related macular degeneration in a subject in need thereof, the method comprising: administering to the subject an effective amount of the anti-C3 antibody single chain fragment according to claim 48.

67. A method of treating age-related macular degeneration in a subject in need thereof, the method comprising: administering to the subject an effective amount of the anti-C3 antibody single chain fragment according to claim 49.

68. A method of preventing age-related macular degeneration in a subject in need thereof, the method comprising: administering to the subject an effective amount of the anti-C3 antibody single chain fragment according to claim 44.

69. A method of preventing age-related macular degeneration in a subject in need thereof, the method comprising: administering to the subject an effective amount of the anti-C3 antibody single chain fragment according to claim 45.

70. A method of preventing age-related macular degeneration in a subject in need thereof, the method comprising: administering to the subject an effective amount of the anti-C3 antibody single chain fragment according to claim 46.

71. A method of preventing age-related macular degeneration in a subject in need thereof, the method comprising: administering to the subject an effective amount of the anti-C3 antibody single chain fragment according to claim 47.

72. A method of preventing age-related macular degeneration in a subject in need thereof, the method comprising: administering to the subject an effective amount of the anti-C3 antibody single chain fragment according to claim 48.

73. A method of preventing age-related macular degeneration in a subject in need thereof, the method comprising: administering to the subject an effective amount of the anti-C3 antibody single chain fragment according to claim 49.

74. A method of treating diabetic retinopathy in a subject in need thereof, the method comprising: administering to the subject an effective amount of the anti-C3 antibody single chain fragment according to claim 44.

75. A method of treating diabetic retinopathy in a subject in need thereof, the method comprising: administering to the subject an effective amount of the anti-C3 antibody single chain fragment according to claim 45.

76. A method of treating diabetic retinopathy in a subject in need thereof, the method comprising: administering to the subject an effective amount of the anti-C3 antibody single chain fragment according to claim 46.

77. A method of treating diabetic retinopathy in a subject in need thereof, the method comprising: administering to the subject an effective amount of the anti-C3 antibody single chain fragment according to claim 47.

78. A method of treating diabetic retinopathy in a subject in need thereof, the method comprising: administering to the subject an effective amount of the anti-C3 antibody single chain fragment according to claim 48.

79. A method of treating diabetic retinopathy in a subject in need thereof, the method comprising: administering to the subject an effective amount of the anti-C3 antibody single chain fragment according to claim 49.

80. A method of preventing diabetic retinopathy in a subject in need thereof, the method comprising: administering to the subject an effective amount of the anti-C3 antibody single chain fragment according to claim 44.

81. A method of preventing diabetic retinopathy in a subject in need thereof, the method comprising: administering to the subject an effective amount of the anti-C3 antibody single chain fragment according to claim 45.

82. A method of preventing diabetic retinopathy in a subject in need thereof, the method comprising: administering to the subject an effective amount of the anti-C3 antibody single chain fragment according to claim 46.

83. A method of preventing diabetic retinopathy in a subject in need thereof, the method comprising: administering to the subject an effective amount of the anti-C3 antibody single chain fragment according to claim 47.

84. A method of preventing diabetic retinopathy in a subject in need thereof, the method comprising: administering to the subject an effective amount of the anti-C3 antibody single chain fragment according to claim 48.

85. A method of preventing diabetic retinopathy in a subject in need thereof, the method comprising: administering to the subject an effective amount of the anti-C3 antibody single chain fragment according to claim 49.

86. A method of preventing an eye or ocular disease that is mediated by C3-mediated complement activation in a subject in need thereof, the method comprising: administering to the subject an effective amount of the monoclonal anti-C3 antibody or the antigen-binding fragment thereof according to claim 1.

87. The monoclonal anti-C3 antibody or the antigen-binding fragment thereof according to claim 1, wherein the antibody or the antigen-binding fragment thereof comprises:
a heavy chain variable region comprising an amino acid sequence at least 90% identical to the amino acid sequence of SEQ ID NO: 20, 22 or 24; and
a light chain variable region comprising an amino acid sequence at least 90% identical to the amino acid sequence of SEQ ID NO: 21, 23 or 25.

88. The monoclonal anti-C3 antibody or the antigen-binding fragment thereof according to claim 1, wherein the antibody or the antigen-binding fragment thereof comprises:
a heavy chain variable region comprising an amino acid sequence at least 95% identical to the amino acid sequence of SEQ ID NO: 20, 22 or 24; and
a light chain variable region comprising an amino acid sequence at least 95% identical to the amino acid sequence of SEQ ID NO: 21, 23 or 25.

89. The monoclonal anti-C3 antibody or the antigen-binding fragment thereof according to claim 1, wherein the antibody or the antigen-binding fragment thereof comprises:
a heavy chain variable region comprising an amino acid sequence at least 98% identical to the amino acid sequence of SEQ ID NO: 20, 22 or 24; and
a light chain variable region comprising an amino acid sequence at least 98% identical to the amino acid sequence of SEQ ID NO: 21, 23 or 25.

90. The monoclonal anti-C3 antibody or the antigen-binding fragment thereof according to claim 1, wherein the antibody or the antigen-binding fragment thereof comprises:
a heavy chain variable region comprising an amino acid sequence at least 99% identical to the amino acid sequence of SEQ ID NO: 20, 22 or 24; and
a light chain variable region comprising an amino acid sequence at least 99% identical to the amino acid sequence of SEQ ID NO: 21, 23 or 25.

91. The monoclonal anti-C3 antibody or the antigen-binding fragment thereof according to claim 1, comprising:
a heavy chain variable region comprising an amino acid sequence at least 90% identical to the amino acid sequence of SEQ ID NO: 20, 22 or 24; and
a light chain variable region comprising an amino acid sequence at least 90% identical to the amino acid sequence of SEQ ID NO: 21, 23 or 25;
wherein the VH comprises the CDR-H1 sequence of SEQ ID NO: 1, the CDR-H2 sequence of SEQ ID NO: 2 or 15, the CDR-H3 sequence of SEQ ID NO: 3; and
wherein the VL comprises the CDR-L1 sequence of SEQ ID NO: 4, the CDR-L2 sequence of SEQ ID NO: 5 or 18, and the CDR-L3 sequence of SEQ ID NO: 6.

92. The monoclonal anti-C3 antibody or the antigen-binding fragment thereof according to claim 1, comprising:
a heavy chain variable region comprising an amino acid sequence at least 95% identical to the amino acid sequence of SEQ ID NO: 20, 22 or 24; and
a light chain variable region comprising an amino acid sequence at least 95% identical to the amino acid sequence of SEQ ID NO: 21, 23 or 25;
wherein the VH comprises the CDR-H1 sequence of SEQ ID NO: 1, the CDR-H2 sequence of SEQ ID NO: 2 or 15, the CDR-H3 sequence of SEQ ID NO: 3; and
wherein the VL comprises the CDR-L1 sequence of SEQ ID NO: 4, the CDR-L2 sequence of SEQ ID NO: 5 or 18, and the CDR-L3 sequence of SEQ ID NO: 6.

93. The monoclonal anti-C3 antibody or the antigen-binding fragment thereof according to claim 1, comprising:
a heavy chain variable region comprising an amino acid sequence at least 98% identical to the amino acid sequence of SEQ ID NO: 20, 22 or 24; and
a light chain variable region comprising an amino acid sequence at least 98% identical to the amino acid sequence of SEQ ID NO: 21, 23 or 25;
wherein the VH comprises the CDR-H1 sequence of SEQ ID NO: 1, the CDR-H2 sequence of SEQ ID NO: 2 or 15, the CDR-H3 sequence of SEQ ID NO: 3; and
wherein the VL comprises the CDR-L1 sequence of SEQ ID NO: 4, the CDR-L2 sequence of SEQ ID NO: 5 or 18, and the CDR-L3 sequence of SEQ ID NO: 6.

94. The monoclonal anti-C3 antibody or the antigen-binding fragment thereof according to claim 1, comprising:
a heavy chain variable region comprising an amino acid sequence at least 99% identical to the amino acid sequence of SEQ ID NO: 20, 22 or 24; and
a light chain variable region comprising an amino acid sequence at least 99% identical to the amino acid sequence of SEQ ID NO: 21, 23 or 25;
wherein the VH comprises the CDR-H1 sequence of SEQ ID NO: 1, the CDR-H2 sequence of SEQ ID NO: 2 or 15, the CDR-H3 sequence of SEQ ID NO: 3; and
wherein the VL comprises the CDR-L1 sequence of SEQ ID NO: 4, the CDR-L2 sequence of SEQ ID NO: 5 or 18, and the CDR-L3 sequence of SEQ ID NO: 6.

* * * * *

SEQUENCE LISTING

```
Sequence total quantity: 65
SEQ ID NO: 1             moltype = AA  length = 5
FEATURE                  Location/Qualifiers
REGION                   1..5
                         note = CDR-H1
source                   1..5
                         mol_type = protein
                         organism = synthetic construct
SEQUENCE: 1
NYAMN                                                                    5

SEQ ID NO: 2             moltype = AA  length = 17
FEATURE                  Location/Qualifiers
REGION                   1..17
                         note = HCDR2
source                   1..17
                         mol_type = protein
                         organism = synthetic construct
SEQUENCE: 2
VISYDGSNKY YADSVKG                                                       17

SEQ ID NO: 3             moltype = AA  length = 11
FEATURE                  Location/Qualifiers
REGION                   1..11
                         note = CDR-H3
source                   1..11
                         mol_type = protein
                         organism = synthetic construct
SEQUENCE: 3
AVGYHHARLD P                                                             11

SEQ ID NO: 4             moltype = AA  length = 12
FEATURE                  Location/Qualifiers
REGION                   1..12
```

```
                       note = CDR-L1
source                 1..12
                       mol_type = protein
                       organism = synthetic construct
SEQUENCE: 4
TLSSAHKTYT ID                                                                         12

SEQ ID NO: 5           moltype = AA   length = 11
FEATURE                Location/Qualifiers
REGION                 1..11
                       note = CDR-L2
source                 1..11
                       mol_type = protein
                       organism = synthetic construct
SEQUENCE: 5
LKSDGSYTKG S                                                                          11

SEQ ID NO: 6           moltype = AA   length = 9
FEATURE                Location/Qualifiers
REGION                 1..9
                       note = CDR-L3
source                 1..9
                       mol_type = protein
                       organism = synthetic construct
SEQUENCE: 6
GTEGVGGYV                                                                              9

SEQ ID NO: 7           moltype = AA   length = 10
FEATURE                Location/Qualifiers
REGION                 1..10
                       note = CDR-H1
source                 1..10
                       mol_type = protein
                       organism = synthetic construct
SEQUENCE: 7
GFTFSNYAMN                                                                            10

SEQ ID NO: 8           moltype = AA   length = 7
FEATURE                Location/Qualifiers
REGION                 1..7
                       note = CDR-H1
source                 1..7
                       mol_type = protein
                       organism = synthetic construct
SEQUENCE: 8
GFTFSNY                                                                                7

SEQ ID NO: 9           moltype = AA   length = 6
FEATURE                Location/Qualifiers
REGION                 1..6
                       note = CDR-H2
source                 1..6
                       mol_type = protein
                       organism = synthetic construct
SEQUENCE: 9
SYDGSN                                                                                 6

SEQ ID NO: 10          moltype = AA   length = 8
FEATURE                Location/Qualifiers
REGION                 1..8
                       note = CDR-H1
source                 1..8
                       mol_type = protein
                       organism = synthetic construct
SEQUENCE: 10
GFTFSNYA                                                                               8

SEQ ID NO: 11          moltype = AA   length = 8
FEATURE                Location/Qualifiers
REGION                 1..8
                       note = CDR-H2
source                 1..8
                       mol_type = protein
                       organism = synthetic construct
SEQUENCE: 11
ISYDGSNK                                                                               8

SEQ ID NO: 12          moltype = AA   length = 13
FEATURE                Location/Qualifiers
```

```
REGION                  1..13
                        note = CDR-H3
source                  1..13
                        mol_type = protein
                        organism = synthetic construct
SEQUENCE: 12
ARAVGYHHAR LDP                                                        13

SEQ ID NO: 13           moltype = AA  length = 7
FEATURE                 Location/Qualifiers
REGION                  1..7
                        note = CDR-L1
source                  1..7
                        mol_type = protein
                        organism = synthetic construct
SEQUENCE: 13
SAHKTYT                                                                7

SEQ ID NO: 14           moltype = AA  length = 7
FEATURE                 Location/Qualifiers
REGION                  1..7
                        note = CDR-L2
source                  1..7
                        mol_type = protein
                        organism = synthetic construct
SEQUENCE: 14
LKSDGSY                                                                7

SEQ ID NO: 15           moltype = AA  length = 16
FEATURE                 Location/Qualifiers
REGION                  1..16
                        note = CDR-H2
source                  1..16
                        mol_type = protein
                        organism = synthetic construct
SEQUENCE: 15
IINVGGGTNY ADSVKG                                                     16

SEQ ID NO: 16           moltype = AA  length = 5
FEATURE                 Location/Qualifiers
REGION                  1..5
                        note = CDR-H2
source                  1..5
                        mol_type = protein
                        organism = synthetic construct
SEQUENCE: 16
NVGGG                                                                  5

SEQ ID NO: 17           moltype = AA  length = 7
FEATURE                 Location/Qualifiers
REGION                  1..7
                        note = CDR-H2
source                  1..7
                        mol_type = protein
                        organism = synthetic construct
SEQUENCE: 17
INVGGGT                                                                7

SEQ ID NO: 18           moltype = AA  length = 11
FEATURE                 Location/Qualifiers
REGION                  1..11
                        note = CDR-L2
source                  1..11
                        mol_type = protein
                        organism = synthetic construct
SEQUENCE: 18
LKSEGSYTKG S                                                          11

SEQ ID NO: 19           moltype = AA  length = 7
FEATURE                 Location/Qualifiers
REGION                  1..7
                        note = CDR-L2
source                  1..7
                        mol_type = protein
                        organism = synthetic construct
SEQUENCE: 19
LKSEGSY                                                                7

SEQ ID NO: 20           moltype = AA  length = 120
```

```
FEATURE              Location/Qualifiers
REGION               1..120
                     note = VH
source               1..120
                     mol_type = protein
                     organism = synthetic construct
SEQUENCE: 20
QVQLVESGGG SVQPGRSLRL SCAASGFTFS NYAMNWVRQA PGKGLEWVAV ISYDGSNKYY    60
ADSVKGRFTI SRDNSKNTLY LQMNSLRAED TASYYCARAV GYHHARLDPW GCGTSVTVSS   120

SEQ ID NO: 21        moltype = AA   length = 112
FEATURE              Location/Qualifiers
REGION               1..112
                     note = VL
source               1..112
                     mol_type = protein
                     organism = synthetic construct
SEQUENCE: 21
QLVLTQSPSA SASLGASVKL TCTLSSAHKT YTIDWYQQQP EKCPRYLMQL KSDGSYTKGS    60
GIPDRFSGSS SGAERYLTIS SLQSEDEADY YCGTEGVGGY VFGGGTKLTV LG           112

SEQ ID NO: 22        moltype = AA   length = 119
FEATURE              Location/Qualifiers
REGION               1..119
                     note = VH
source               1..119
                     mol_type = protein
                     organism = synthetic construct
SEQUENCE: 22
QVQLVESGGG SVQPGRSLRL SCAASGFTFS NYAMNWVRQA PGKGLEWVAI INVGGGTNYA    60
DSVKGRFTIS RDNSKNTLYL QMNSLRAEDT ASYYCARAVG YHHARLDPWG CGTSVTVSS    119

SEQ ID NO: 23        moltype = AA   length = 112
FEATURE              Location/Qualifiers
REGION               1..112
                     note = VL
source               1..112
                     mol_type = protein
                     organism = synthetic construct
SEQUENCE: 23
QLVLTQSPSA SASLGASVKL TCTLSSAHKT YTIDWYQQQP EKCPRYLMQL KSDGSYTKGS    60
GIPDRFSGSS SGAERYLTIS SLQSEDEADY YCGTEGVGGY VFGGGTKLTV LG           112

SEQ ID NO: 24        moltype = AA   length = 119
FEATURE              Location/Qualifiers
REGION               1..119
                     note = VH
source               1..119
                     mol_type = protein
                     organism = synthetic construct
SEQUENCE: 24
QVQLVESGGG SVQPGRSLRL SCAASGFTFS NYAMNWVRQA PGKGLEWVAI INVGGGTNYA    60
DSVKGRFTIS RDNSKNTLYL QMNSLRAEDT ASYYCARAVG YHHARLDPWG CGTSVTVSS    119

SEQ ID NO: 25        moltype = AA   length = 112
FEATURE              Location/Qualifiers
REGION               1..112
                     note = VL
source               1..112
                     mol_type = protein
                     organism = synthetic construct
SEQUENCE: 25
QLVLTQSPSA SASLGASVKL TCTLSSAHKT YTIDWYQQQP EKCPRYLMQL KSEGSYTKGS    60
GIPDRFSGSS SGAERYLTIS SLQSEDEADY YCGTEGVGGY VFGGGTKLTV LG           112

SEQ ID NO: 26        moltype = AA   length = 252
FEATURE              Location/Qualifiers
REGION               1..252
                     note = ScFv
source               1..252
                     mol_type = protein
                     organism = synthetic construct
SEQUENCE: 26
QLVLTQSPSA SASLGASVKL TCTLSSAHKT YTIDWYQQQP EKCPRYLMQL KSDGSYTKGS    60
GIPDRFSGSS SGAERYLTIS SLQSEDEADY YCGTEGVGGY VFGGGTKLTV LGGGGGSGGG   120
GSGGGGSGGG GSQVQLVESG GGSVQPGRSL RLSCAASGFT FSNYAMNWVR QAPGKGLEWV   180
AVISYDGSNK YYADSVKGRF TISRDNSKNT LYLQMNSLRA EDTASYYCAR AVGYHHARLD   240
PWGCGTSVTV SS                                                       252
```

```
SEQ ID NO: 27              moltype = AA   length = 253
FEATURE                    Location/Qualifiers
REGION                     1..253
                           note = ScFv
source                     1..253
                           mol_type = protein
                           organism = synthetic construct
SEQUENCE: 27
MQLVLTQSPS ASASLGASVK LTCTLSSAHK TYTIDWYQQQ PEKCPRYLMQ LKSDGSYTKG    60
SGIPDRFSGS SSGAERYLTI SSLQSEDEAD YYCGTEGVGG YVFGGGTKLT VLGGGGSGG    120
GGSGGGGSGG GGSQVQLVES GGGSVQPGRS LRLSCAASGF TFSNYAMNWV RQAPGKGLEW   180
VAVISYDGSN KYYADSVKGR FTISRDNSKN TLYLQMNSLR AEDTASYYCA RAVGYHHARL   240
DPWGCGTSVT VSS                                                     253

SEQ ID NO: 28              moltype = AA   length = 251
FEATURE                    Location/Qualifiers
REGION                     1..251
                           note = ScFv
source                     1..251
                           mol_type = protein
                           organism = synthetic construct
SEQUENCE: 28
QLVLTQSPSA SASLGASVKL TCTLSSAHKT YTIDWYQQPP EKCPRYLMQL KSDGSYTKGS    60
GIPDRFSGSS SGAERYLTIS SLQSEDEADY YCGTEGVGGY VFGGGTKLTV LGGGGSGGG   120
GSGGGGSGGG GSQVQLVESG GGSVQPGRSL RLSCAASGFT FSNYAMNWVR QAPGKGLEWV   180
AIINVGGGTN YADSVKGRFT ISRDNSKNTL YLQMNSLRAE DTASYYCARA VGYHHARLDP   240
WGCGTSVTVS S                                                       251

SEQ ID NO: 29              moltype = AA   length = 252
FEATURE                    Location/Qualifiers
REGION                     1..252
                           note = ScFv
source                     1..252
                           mol_type = protein
                           organism = synthetic construct
SEQUENCE: 29
MQLVLTQSPS ASASLGASVK LTCTLSSAHK TYTIDWYQQQ PEKCPRYLMQ LKSDGSYTKG    60
SGIPDRFSGS SSGAERYLTI SSLQSEDEAD YYCGTEGVGG YVFGGGTKLT VLGGGGSGG   120
GGSGGGGSGG GGSQVQLVES GGGSVQPGRS LRLSCAASGF TFSNYAMNWV RQAPGKGLEW   180
VAIINVGGGT NYADSVKGRF TISRDNSKNT LYLQMNSLRA EDTASYYCAR AVGYHHARLD   240
PWGCGTSVTV SS                                                      252

SEQ ID NO: 30              moltype = AA   length = 251
FEATURE                    Location/Qualifiers
REGION                     1..251
                           note = ScFv
source                     1..251
                           mol_type = protein
                           organism = synthetic construct
SEQUENCE: 30
QLVLTQSPSA SASLGASVKL TCTLSSAHKT YTIDWYQQPP EKCPRYLMQL KSEGSYTKGS    60
GIPDRFSGSS SGAERYLTIS SLQSEDEADY YCGTEGVGGY VFGGGTKLTV LGGGGSGGG   120
GSGGGGSGGG GSQVQLVESG GGSVQPGRSL RLSCAASGFT FSNYAMNWVR QAPGKGLEWV   180
AIINVGGGTN YADSVKGRFT ISRDNSKNTL YLQMNSLRAE DTASYYCARA VGYHHARLDP   240
WGCGTSVTVS S                                                       251

SEQ ID NO: 31              moltype = AA   length = 252
FEATURE                    Location/Qualifiers
REGION                     1..252
                           note = ScFv
source                     1..252
                           mol_type = protein
                           organism = synthetic construct
SEQUENCE: 31
MQLVLTQSPS ASASLGASVK LTCTLSSAHK TYTIDWYQQQ PEKCPRYLMQ LKSEGSYTKG    60
SGIPDRFSGS SSGAERYLTI SSLQSEDEAD YYCGTEGVGG YVFGGGTKLT VLGGGGSGG   120
GGSGGGGSGG GGSQVQLVES GGGSVQPGRS LRLSCAASGF TFSNYAMNWV RQAPGKGLEW   180
VAIINVGGGT NYADSVKGRF TISRDNSKNT LYLQMNSLRA EDTASYYCAR AVGYHHARLD   240
PWGCGTSVTV SS                                                      252

SEQ ID NO: 32              moltype = AA   length = 250
FEATURE                    Location/Qualifiers
REGION                     1..250
                           note = scFv
source                     1..250
                           mol_type = protein
                           organism = synthetic construct
SEQUENCE: 32
QSVKESGGRL VTPGTPLTLT CTVSGFSLYN YAMNWVRQAP GKGLEWIGII NTDGNTNYAS    60
```

```
WAKGRFTIST TSSTTVDLKI TSPTTEDTAT YFCPRAVGYH HHALDPWGPG TLVTVSSGGG    120
GSGGGGSGGG GSGGGGASEL VLTQSPSVSA ALGASAKLTC TLSSAHKTYT IDWYQQQQGE    180
APRYLMQLKS DGSYTKGTGV PDRFSGSSSG ADRYLIIPSV QADDEADYYC GTDYGGGYVF    240
GGGTQLTVTG                                                          250

SEQ ID NO: 33              moltype = AA  length = 252
FEATURE                    Location/Qualifiers
REGION                     1..252
                           note = ScFv
source                     1..252
                           mol_type = protein
                           organism = synthetic construct
SEQUENCE: 33
MQLVLTQSPS ASASLGASVK LTCTLSSAHK TYTIDWYQQQ PEKGPRYLMQ LKSDGSYTKG     60
TGVPDRFSGS SSGAERYLTI SSLQSEDEAD YYCGTDYGGG YVFGGGTKLT VLGGGGGSGG    120
GGSGGGGSGG GGSQVQVVES GGGSVQPGRS LRLSCAASGF SLYNYAMNWV RQAPGKGLEW    180
IGIIINTDGNT NYASWAKGRF TISTDNSKNT LYLQMNSLRA EDTASYYCPR AVGYHHHALD    240
PWGQGTSVTV SS                                                        252

SEQ ID NO: 34              moltype = AA  length = 252
FEATURE                    Location/Qualifiers
REGION                     1..252
                           note = ScFv
source                     1..252
                           mol_type = protein
                           organism = synthetic construct
SEQUENCE: 34
MQLVLTQSPS ASASLGASVK LTCTLSSAHK TYTIDWYQQQ PEKGPRYLMQ LKSDGSYTKG     60
TGVPDRFSGS SSGAERYLTI SSLQSEDEAD YYCGTDYGGG YVFGGGTKLT VLGGGGGSGG    120
GGSGGGGSGG GGSQVQVVES GGGSVQPGRS LRLSCAASGF SLYNYAMNWV RQAPGKGLEW    180
IGIIINTDGNT NYASWAKGRF TISTDNSKNT LYLQMNSLRA EDTASYYCAR AVGYHHHALD    240
PWGQGTSVTV SS                                                        252

SEQ ID NO: 35              moltype = AA  length = 252
FEATURE                    Location/Qualifiers
REGION                     1..252
                           note = ScFv
source                     1..252
                           mol_type = protein
                           organism = synthetic construct
SEQUENCE: 35
MQLVLTQSPS ASASLGASVK LTCTLSSAHK TYTIDWYQQQ PEKGPRYLMQ LKSEGSYTKG     60
TGVPDRFSGS SSGAERYLTI SSLQSEDSAV YYCGTEGVGG YVFGCGTKLT VLGGGGGSGG    120
GGSGGGGSGG GGSQVQVVES GGGSVQPGRS LRLSCAVSGF SLYNYAMNWV RQAPGKCLEW    180
IGIINVGGGT NYASWAKGRF TISTDNSKNT VYLQMNSLRA EDTASYYCAR AVGYHHHALD    240
PWGQGTSVTV SS                                                        252

SEQ ID NO: 36              moltype = AA  length = 252
FEATURE                    Location/Qualifiers
REGION                     1..252
                           note = ScFv
source                     1..252
                           mol_type = protein
                           organism = synthetic construct
SEQUENCE: 36
MQLVLTQSPS ASASLGASVK LTCTLSSAHK TYTIDWYQQQ PEKGPRYLMQ LKSEGSYTKG     60
TGVPDRFSGS SSGAERYLTI SSLQSEDSAV YYCGTEGVGG YVFGCGTKLT VLGGGGGSGG    120
GGSGGGGSGG GGSQVQVVES GGGSVQPGRS LRLSCAVSGF SLYNYAMNWV RQAPGKCLEW    180
IGIINVGGGT NYASWAKGRF TISTDNSKNT VYLQMNSLRA EDTASYYCAR AVGYHHSRLD    240
PWGQGTSVTV SS                                                        252

SEQ ID NO: 37              moltype = AA  length = 252
FEATURE                    Location/Qualifiers
REGION                     1..252
                           note = ScFv
source                     1..252
                           mol_type = protein
                           organism = synthetic construct
SEQUENCE: 37
MQLVLTQSPS ASASLGASVK LTCTLSSAHK TYTIDWYQQQ PEKGPRYLMQ LKSEGSYTKG     60
TGVPDRFSGS SSGAERYLTI SSLQSEDSAV YYCGTDGVGG YVFGCGTKLT VLGGGGGSGG    120
GGSGGGGSGG GGSQVQVVES GGGSVQPGRS LRLSCAVSGF SLYNYAMNWV RQAPGKCLEW    180
IGIINVGGGT NYASWAKGRF TISTDNSKNT VYLQMNSLRA EDTASYYCAR AVGYHHHALD    240
PWGQGTSVTV SS                                                        252

SEQ ID NO: 38              moltype = AA  length = 252
FEATURE                    Location/Qualifiers
REGION                     1..252
                           note = ScFv
```

```
                           source                    1..252
                                                     mol_type = protein
                                                     organism = synthetic construct
                           SEQUENCE: 38
                           MQLVLTQSPS ASASLGASVK LTCTLSSAHK TYTIDWYQQQ PEKGPRYLMQ LKSDGSYTKG    60
                           TGVPDRFSGS SSGAERYLTI SSLQSEDEAD YYCGTDYGGG YVFGGGTKLT VLGGGGGSGG   120
                           GGSGGGGSGG GGSQVQVVES GGGSVQPGRS LRLSCTVSGF SLYNYAMNWV RQAPGKGLEW   180
                           IGIINTDGNT NYASWAKGRF TISTDNSKNT VYLQMNSLRA EDTASYYCAR AVGYHHHALD   240
                           PWGQGTSVTV SS                                                       252

SEQ ID NO: 39             moltype = AA   length = 252
                           FEATURE                   Location/Qualifiers
                           REGION                    1..252
                                                     note = ScFv
                           source                    1..252
                                                     mol_type = protein
                                                     organism = synthetic construct
                           SEQUENCE: 39
                           MQLVLTQSPS ASASLGASVK LTCTLSSAHK TYTIDWYQQQ PEKCPRYLMQ LKSDGSYTKG    60
                           TGVPDRFSGS SSGAERYLTI SSLQSEDEAD YYCGTDYGGG YVFGGGTKLT VLGGGGGSGG   120
                           GGSGGGGSGG GGSQVQVVES GGGSVQPGRS LRLSCTVSGF SLYNYAMNWV RQAPGKGLEW   180
                           IGIINTDGNT NYASWAKGRF TISTDNSKNT VYLQMNSLRA EDTASYYCAR AVGYHHHALD   240
                           PWGCGTSVTV SS                                                       252

SEQ ID NO: 40             moltype = AA   length = 252
                           FEATURE                   Location/Qualifiers
                           REGION                    1..252
                                                     note = ScFv
                           source                    1..252
                                                     mol_type = protein
                                                     organism = synthetic construct
                           SEQUENCE: 40
                           MQLVLTQSPS ASASLGASVK LTCTLSSAHK TYTIDWYQQQ PEKCPRYLMQ LKSEGSYTKG    60
                           TGVPDRFSGS SSGAERYLTI SSLQSEDEAD YYCGTDYGGG YVFGGGTKLT VLGGGGGSGG   120
                           GGSGGGGSGG GGSQVQVVES GGGSVQPGRS LRLSCAVSGF SLYNYAMNWV RQAPGKGLEW   180
                           IGIINVGGGT NYASWAKGRF TISTDNSKNT VYLQMNSLRA EDTASYYCAR AVGYHHARLD   240
                           PWGCGTSVTV SS                                                       252

SEQ ID NO: 41             moltype = AA   length = 252
                           FEATURE                   Location/Qualifiers
                           REGION                    1..252
                                                     note = ScFv
                           source                    1..252
                                                     mol_type = protein
                                                     organism = synthetic construct
                           SEQUENCE: 41
                           MQLVLTQSPS ASASLGASVK LTCTLSSAHK TYTIDWYQQQ PEKCPRYLMQ LKSEGSYTKG    60
                           TGVPDRFSGS SSGAERYLTI SSLQSEDEAD YYCGTEGVGG YVFGGGTKLT VLGGGGGSGG   120
                           GGSGGGGSGG GGSQVQVVES GGGSVQPGRS LRLSCAVSGF SLYNYAMNWV RQAPGKGLEW   180
                           IGIINVGGGT NYASWAKGRF TISTDNSKNT VYLQMNSLRA EDTASYYCAR AVGYHHARLD   240
                           PWGCGTSVTV SS                                                       252

SEQ ID NO: 42             moltype = AA   length = 252
                           FEATURE                   Location/Qualifiers
                           REGION                    1..252
                                                     note = ScFv
                           source                    1..252
                                                     mol_type = protein
                                                     organism = synthetic construct
                           SEQUENCE: 42
                           MQLVLTQSPS ASASLGASVK LTCTLSSAHK TYTIDWYQQQ PEKCPRYLMQ LKSEGSYTKG    60
                           TGVPDRFSGS SSGAERYLTI SSLQSEDEAD YYCGTEGVGG YVFGGGTKLT VLGGGGGSGG   120
                           GGSGGGGSGG GGSQVQVVES GGGSVQPGRS LRLSCAVSGF SLYNYAMNWV RQAPGKGLEW   180
                           IGIINVGGGT NYASWAKGRF TISTDNSKNT VYLQMNSLRA EDTASYYCAR AVGYHHSRLD   240
                           PWGCGTSVTV SS                                                       252

SEQ ID NO: 43             moltype = AA   length = 5
                           FEATURE                   Location/Qualifiers
                           REGION                    1..5
                                                     note = linkerGGGGS
                           source                    1..5
                                                     mol_type = protein
                                                     organism = synthetic construct
                           SEQUENCE: 43
                           GGGGS                                                                 5

SEQ ID NO: 44             moltype = AA   length = 10
                           FEATURE                   Location/Qualifiers
                           REGION                    1..10
```

```
                              note = Linker
           source             1..10
                              mol_type = protein
                              organism = synthetic construct
SEQUENCE: 44
GGGGSGGGGS                                                                    10

SEQ ID NO: 45             moltype = AA   length = 15
FEATURE                   Location/Qualifiers
REGION                    1..15
                          note = Linker
           source             1..15
                              mol_type = protein
                              organism = synthetic construct
SEQUENCE: 45
GGGGSGGGGS GGGGS                                                              15

SEQ ID NO: 46             moltype = AA   length = 20
FEATURE                   Location/Qualifiers
REGION                    1..20
                          note = Linker
           source             1..20
                              mol_type = protein
                              organism = synthetic construct
SEQUENCE: 46
GGGGSGGGGS GGGGSGGGGS                                                         20

SEQ ID NO: 47             moltype = AA   length = 1663
FEATURE                   Location/Qualifiers
source                    1..1663
                          mol_type = protein
                          organism = Homo sapiens
SEQUENCE: 47
MGPTSGPSLL LLLLTHLPLA LGSPMYSIIT PNILRLESEE TMVLEAHDAQ GDVPVTVTVH    60
DFPGKKLVLS SEKTVLTPAT NHMGNVTFTI PANREFKSEK GRNKFVTVQA TFGTQVVEKV   120
VLVSLQSGYL FIQTDKTIYT PGSTVLYRIF TVNHKLLPVG RTVMVNIENP EGIPVKQDSL   180
SSQNQLGVLP LSWDIPELVN MGQWKIRAYY ENSPQQVFST EFEVKEYVLP SFEVIVEPTE   240
KFYYIYNEKG LEVTITARFL YGKKVEGTAF VIFGIQDGEQ RISLPESLKR IPIEDGSGEV   300
VLSRKVLLDG VQNPRAEDLV GKSLYVSATV ILHSGSDMVQ AERSGIPIVT SPYQIHFTKT   360
PKYFKPGMPF DLMVFVTNPD GSPAYRVPVA VQGEDTVQSL TQGDGVAKLS INTHPSQKPL   420
SITVRTKKQE LSEAEQATRT MQALPYSTVG NSNNYLHLSV LRTELRPGET LNVNFLLRMD   480
RAHEAKIRYY TYLIMNKGRL LKAGRQVREP GQDLVVLPLS ITTDFIPSFR LVAYYTLIGA   540
SGQREVVADS VWVDVKDSCV GSLVVKSGQS EDRQPVPGQQ MTLKIEGDHG ARVVLVAVDK   600
GVFVLNKKNK LTQSKIWDVV EKADIGCTPG SGKDYAGVFS DAGLTFTSSS GQQTAQRAEL   660
QCPQPAARRR RSVQLTEKRM DKVGKYPKEL RKCCEDGMRE NPMRFSCQRR TRFISLGEAC   720
KKVFLDCCNY ITELRRQHAR ASHLGLARSN LDEDIIAEEN IVSRSEFPES WLWNVEDLKE   780
PPKNGISTKL MNIFLKDSIT TWEILAVSMS DKKGICVADP FEVTVMQDFF IDLRLPYSVV   840
RNEQVEIRAV LYNYRQNQEL KVRVELLHNP AFCSLATTKR RHQQTVTIPP KSSLSVPYVI   900
VPLKTGLQEV EVKAAVYHHF ISDGVRKSLK VVPEGIRMNK TVAVRTLDPE RLGREGVQKE   960
DIPPADLSDQ VPDTESETRI LLQGTPVAQM TEDAVDAERL KHLIVTPSGC GEQNMIGMTP  1020
TVIAVHYLDE TEQWEKFGLE KRQGALELIK KGYTQQLAFR QPSSAFAAFV KRAPSTWLTA  1080
YVVKVFSLAV NLIAIDSQVL CGAVKWLILE KQKPDGVFQE DAPVIHQEMI GGLRNNNEKD  1140
MALTAFVLIS LQEAKDICEE QVNSLPGSIT KAGDFLEANY MNLQRSYTVA IAGYALAQMG  1200
RLKGPLLNKF LTTAKDKNRW EDPGKQLYNV EATSYALLAL LQLKDFDFVP PVVRWLNEQR  1260
YYGGGYGSTQ ATFMVPQALA QYQKDAPDHQ ELNLDVSLQL PSRSSKITHR IHWESASLLR  1320
SEETKENEGF TVTAEGKGQG TLSVVTMYHA KAKDQLTCNK FDLKVTIKPA PETEKRPQDA  1380
KNTMILEICT RYRGDQDATM SILDISMMTG FAPDTDDLKQ LANGVDRYIS KYELDKAFSD  1440
RNTLIIYLDK VSHSEDDCLA FKVHQYFNVE LIQPGAVKVY AYYNLEESCT RFYHPEKEDG  1500
KLNKLCRDEL CRCAEENCFI QKSDDKVTLE ERLDKACEPG VDYVYKTRLV KVQLSNDFDE  1560
YIMAIEQTIK SGSDEVQVGQ QRTFISPIKC REALKLEEKK HYLMWGLSSD FWGEKPNLSY  1620
IIGKDTWVEH WPEEDECQDE ENQKQCQDLG AFTESMVVFG CPN                   1663

SEQ ID NO: 48             moltype = AA   length = 643
FEATURE                   Location/Qualifiers
REGION                    1..643
                          note = Chain D of the human Complement C3c
           source             1..643
                              mol_type = protein
                              organism = Homo sapiens
SEQUENCE: 48
SPMYSIITPN ILRLESEETM VLEAHDAQGD VPVTVTVHDF PGKKLVLSSE KTVLTPATNH    60
MGNVTFTIPA NREFKSEKGR NKFVTVQATF GTQVVEKVVL VSLQSGYLFI QTDKTIYTPG   120
STVLYRIFTV NHKLLPVGRT VMVNIENPEG IPVKQDSLSS QNQLGVLPLS WDIPELVNMG   180
QWKIRAYYEN SPQQVFSTEF EVKEYVLPSF EVIVEPTEKF YYIYNEKGLE VTITARFLYG   240
KKVEGTAFVI FGIQDGEQRI SLPESLKRIP IEDGSGEVVL SRKVLLDGVQ NLRAEDLVGK   300
SLYVSATVIL HSGSDMVQAE RSGIPIVTSP YQIHFTKTPK YFKPGMPFDL MVFVTNPDGS   360
PAYRVPVAVQ GEDTVQSLTQ GDGVAKLSIN THPSQKPLSI TVRTKKQELS EAEQATRTMQ   420
ALPYSTVGNS NNYLHLSVLR TELRPGETLN VNFLLRMDRA HEAKIRYYTY LIMNKGRLLK   480
AGRQVREPGQ DLVVLPLSIT TDFIPSFRLV AYYTLIGASG QREVVADSVW VDVKDSCVGS   540
```

```
LVVKSGQSED RQPVPGQQMT LKIEGDHGAR VVLVAVDKGV FVLNKKNKLT QSKIWDVVEK   600
ADIGCTPGSG KDYAGVFSDA GLTFTSSSGQ QTAQRAELQC PQP                    643

SEQ ID NO: 49           moltype = AA  length = 13
FEATURE                 Location/Qualifiers
REGION                  1..13
                        note = Comparative Compound C1
source                  1..13
                        mol_type = protein
                        organism = synthetic construct
SEQUENCE: 49
ICVWQDWGAH RCT                                                     13

SEQ ID NO: 50           moltype = AA  length = 14
FEATURE                 Location/Qualifiers
REGION                  1..14
                        note = Comparative Compound C2
source                  1..14
                        mol_type = protein
                        organism = synthetic construct
SEQUENCE: 50
GICVWQDWGA HRCT                                                    14

SEQ ID NO: 51           moltype = AA  length = 117
FEATURE                 Location/Qualifiers
REGION                  1..117
                        note = Compound C3 - VH
source                  1..117
                        mol_type = protein
                        organism = synthetic construct
SEQUENCE: 51
QVQLVQSGAE VKKPGASVKV SCKASGYTFT DFYMDWVRQA PGQRLEWMGY IYPHNGGTTY   60
NQQFTGRVTI TVDKSASTAY MELSSLRSED TAVYYCARRG GFDFDYWGQG TLVTVSS     117

SEQ ID NO: 52           moltype = AA  length = 108
FEATURE                 Location/Qualifiers
REGION                  1..108
                        note = Compound C3 - VL
source                  1..108
                        mol_type = protein
                        organism = synthetic construct
SEQUENCE: 52
DIQMTQSPSS LSASVGDRVT ITCKASENVD TYVSWYQQKP GKAPKLLIYG ASNRYTGVPS   60
RFSGSGSGTD FTFTISSLQP EDIATYHCGQ SHSYPLTFGQ GTKLEIKR               108

SEQ ID NO: 53           moltype = AA  length = 447
FEATURE                 Location/Qualifiers
REGION                  1..447
                        note = Compound C3 - HC
source                  1..447
                        mol_type = protein
                        organism = synthetic construct
SEQUENCE: 53
QVQLVQSGAE VKKPGASVKV SCKASGYTFT DFYMDWVRQA PGQRLEWMGY IYPHNGGTTY   60
NQQFTGRVTI TVDKSASTAY MELSSLRSED TAVYYCARRG GFDFDYWGQG TLVTVSSAST  120
KGPSVFPLAP SSKSTSGGTA ALGCLVKDYF PEPVTVSWNS GALTSGVHTF PAVLQSSGLY  180
SLSSVVTVPS SSLGTQTYIC NVNHKPSNTK VDKKVEPKSC DKTHTCPPCP APELLGGPSV  240
FLFPPKPKDT LMISRTPEVT CVVVDVSHED PEVKFNWYVD GVEVHNAKTK PREEQYNSTY  300
RVVSVLTVLH QDWLNGKEYK CKVSNKALPA PIEKTISKAK GQPREPQVYT LPPSRDELTK  360
NQVSLTCLVK GFYPSDIAVE WESNGQPENN YKTTPPVLDS DGSFFLYSKL TVDKSRWQQG  420
NVFSCSVMHE ALHNHYTQKS LSLSPGK                                     447

SEQ ID NO: 54           moltype = AA  length = 214
FEATURE                 Location/Qualifiers
REGION                  1..214
                        note = Compound C3 - LC
source                  1..214
                        mol_type = protein
                        organism = synthetic construct
SEQUENCE: 54
DIQMTQSPSS LSASVGDRVT ITCKASENVD TYVSWYQQKP GKAPKLLIYG ASNRYTGVPS   60
RFSGSGSGTD FTFTISSLQP EDIATYHCGQ SHSYPLTFGQ GTKLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                             214

SEQ ID NO: 55           moltype = AA  length = 150
FEATURE                 Location/Qualifiers
source                  1..150
                        mol_type = protein
```

```
                        organism = Homo sapiens
SEQUENCE: 55
SPYQIHFTKT PKYFKPGMPF DLMVFVTNPD GSPAYRVPVA VQGEDTVQSL TQGDGVAKLS    60
INTHPSQKPL SITVRTKKQE LSEAEQATRT MQALPYSTVG NSNNYLHLSV LRTELRPGET   120
LNVNFLLRMD RAHEAKIRYY TYLIMNKGRL                                    150

SEQ ID NO: 56           moltype = AA  length = 4
FEATURE                 Location/Qualifiers
source                  1..4
                        mol_type = protein
                        organism = synthetic construct
SEQUENCE: 56
GGGS                                                                  4

SEQ ID NO: 57           moltype = AA  length = 6
FEATURE                 Location/Qualifiers
source                  1..6
                        mol_type = protein
                        organism = synthetic construct
SEQUENCE: 57
GGSGGS                                                                6

SEQ ID NO: 58           moltype = AA  length = 7
FEATURE                 Location/Qualifiers
source                  1..7
                        mol_type = protein
                        organism = synthetic construct
SEQUENCE: 58
GGGSGGS                                                               7

SEQ ID NO: 59           moltype = AA  length = 7
FEATURE                 Location/Qualifiers
source                  1..7
                        mol_type = protein
                        organism = synthetic construct
SEQUENCE: 59
SGGSGGS                                                               7

SEQ ID NO: 60           moltype = AA  length = 9
FEATURE                 Location/Qualifiers
source                  1..9
                        mol_type = protein
                        organism = synthetic construct
SEQUENCE: 60
GGGGSGGGS                                                             9

SEQ ID NO: 61           moltype = AA  length = 18
FEATURE                 Location/Qualifiers
source                  1..18
                        mol_type = protein
                        organism = synthetic construct
SEQUENCE: 61
GGGGSGGGGS GGGGGGGS                                                  18

SEQ ID NO: 62           moltype = AA  length = 25
FEATURE                 Location/Qualifiers
source                  1..25
                        mol_type = protein
                        organism = synthetic construct
SEQUENCE: 62
GGGGSGGGGS GGGGSGGGGS GGGGS                                          25

SEQ ID NO: 63           moltype = AA  length = 30
FEATURE                 Location/Qualifiers
source                  1..30
                        mol_type = protein
                        organism = synthetic construct
SEQUENCE: 63
GGGGSGGGGS GGGGSGGGGS GGGGSGGGGS                                     30

SEQ ID NO: 64           moltype = AA  length = 35
FEATURE                 Location/Qualifiers
source                  1..35
                        mol_type = protein
                        organism = synthetic construct
SEQUENCE: 64
GGGGSGGGGS GGGGSGGGGS GGGGSGGGGS GGGGS                               35

SEQ ID NO: 65           moltype = AA  length = 15
```

```
FEATURE            Location/Qualifiers
source             1..15
                   mol_type = protein
                   organism = synthetic construct
SEQUENCE: 65
GGGSSGGGSS GGGSS                                              15
```